(12) United States Patent
Yang

(10) Patent No.: US 10,752,626 B2
(45) Date of Patent: Aug. 25, 2020

(54) ISO-CITRATE DEHYDROGENASE (IDH) INHIBITOR

(71) Applicant: SHANGHAI METON PHARMACEUTICAL CO., LTD, Shanghai (CN)

(72) Inventor: Jibin Yang, Shanghai (CN)

(73) Assignee: SHANGHAI METON PHARMACEUTICAL CO., LTD, Shanghai (CN)

( * ) Notice: Subject to any disclaimer, the term of this patent is extended or adjusted under 35 U.S.C. 154(b) by 0 days.

(21) Appl. No.: 16/315,653

(22) PCT Filed: Jul. 11, 2017

(86) PCT No.: PCT/CN2017/092506
§ 371 (c)(1),
(2) Date: Jan. 6, 2019

(87) PCT Pub. No.: WO2018/010637
PCT Pub. Date: Jan. 18, 2018

(65) Prior Publication Data
US 2019/0256511 A1 Aug. 22, 2019

(30) Foreign Application Priority Data

Jul. 14, 2016 (WO) ................ PCT/CN2016/090022

(51) Int. Cl.
C07D 471/04 (2006.01)
A61P 35/00 (2006.01)
A61K 45/06 (2006.01)

(52) U.S. Cl.
CPC ............ C07D 471/04 (2013.01); A61K 45/06 (2013.01); A61P 35/00 (2018.01)

(58) Field of Classification Search
CPC .................................................. C07D 471/04
USPC ........................................................ 514/300
See application file for complete search history.

(56) References Cited

U.S. PATENT DOCUMENTS

2013/0190249 A1    7/2013  Lemieux et al.

FOREIGN PATENT DOCUMENTS

| WO | 2009072581 A1 | * | 6/2009 |
| WO | WO 2010139953 A1 | * | 12/2010 |
| WO | WO 2015179276 A1 | * | 11/2015 |
| WO | 2016/052697 A1 | | 4/2016 |
| WO | WO 2016060702 A1 | * | 4/2016 |
| WO | 2016/065980 A1 | | 5/2016 |
| WO | WO 2016105518 A1 | * | 6/2016 |
| WO | 2016/171755 A1 | | 10/2016 |

OTHER PUBLICATIONS

Lopez-Valdez et al., Tetrahed. (2011), 67(14), pp. 2693-2701.*
King, Med. Chem., Principle and Practice (1994), pp. 206-208.*
Parsons, D.W., et al., "An integrated genomic analysis of human glioblastoma multiforme", Science, 2008. 321 (5897): p. 1807-1812.
Balss, J., et al., "Analysis of the IDH1 codon 132 mutation in brain tumors", Acta Neuropathol, 2008. 116(6): p. 597-602.
Bleeker, F.E, et al., "IDH1 mutations at residue p. R132 (IDH1(R132)) occur frequently in high-grade gliomas but not in other solid tumors", Hum Mutat, 2009. 30(1): p. 7-11.
Hartmann, C., et al., "Type and frequency of IDH1 and IDH2 mutations are related to astrocytic and oligodendroglial differentiation and age: a study of 1,010 diffuse gliomas", Acta Neuropathol, 2009. 118(4): p. 469-474.
Watanabe, T., et al., "IDH1 mutations are early events in the development of astrocytomas and oligodendrogliomas", Am J Pathol, 2009. 174(4): p. 1149-1153.
Mardis, E.R., et al., "Recurring mutations found by sequencing an acute myeloid leukemia genome", N Engl J Med, 2009. 361(11): p. 1058-1066.
Thol, F., et al., "Prognostic impact of IDH2 mutations in cytogenetically normal acute myeloid leukemia", Blood, 2010. 116(4): p. 614-616.
Abbas, S., et al., "Acquired mutations in the genes encoding IDH1 and IDH2 both are recurrent aberrations in acute myeloid leukemia: prevalence and prognostic value", Blood, 2010. 116(12): p. 2122-2126.
Green, C.L., et al., "The prognostic significance of IDH1 mutations in younger adult patients with acute myeloid leukemia is dependent on FLT3/ITD status", Blood, 2010. 116(15): p. 2779-2782.
Schnittger, S., et al., "IDH1 mutations are detected in 6.6% of 1414 AML patients and are associated with Intermediate risk karyotype and unfavorable prognosis in adults younger than 60 years and unmutated NPM1 status", Blood, 2010. 116(25): p. 5486-5496.
Marcucci, G., et al., "IDH1 and IDH2 gene mutations identify novel molecular subsets within de novo cytogenetically normal acute myeloid leukemia: a Cancer and Leukemia Group B study", J Clin Oncol, 2010. 28(14): p. 2348-2355.
Paschka, P., et al., "IDH1 and IDH2 mutations are frequent genetic alterations in acute myeloid leukemia and confer adverse prognosis in cytogenetically normal acute myeloid leukemia with NPM1 mutation without FLT3 internal tandem duplication", J Clin Oncol, 2010. 28(22): p. 3636-3643.
Ho, P.A., et al., "Molecular alterations of the IDH1 gene in AML: a Children's Oncology Group and Southwest Oncology Group study", Leukemia, 2010. 24(5): p. 909-913.
Amary, M.E, et al., "IDH1 and IDH2 mutations are frequent events in central chondrosarcoma and central and periosteal chondromas but not in other mesenchymal tumours", J Pathol, 2011. 224(3): p. 334-343.
Amary, M.E, et al., "Oilier disease and Maffucci syndrome are caused by somatic mosaic mutations of IDH1 and IDH2", Nat Genet, 2011. 43(12): p. 1262-1265.

(Continued)

Primary Examiner — Taofiq A Solola
(74) Attorney, Agent, or Firm — Jun He Law Offices P.C.; James J. Zhu

(57) ABSTRACT

Disclosed are compounds inhibiting the conversion of α-KG to D-2-HG pharmaceutically acceptable salts, hydrates, solvates or stereoisomers thereof and pharmaceutical compositions comprising the compounds. The compound and the pharmaceutical composition can effectively treat IDH associated diseases, including cancer.

13 Claims, 10 Drawing Sheets

(56) References Cited

OTHER PUBLICATIONS

Borger, D.R., et al., "Frequent mutation of isocitrate dehydrogenase (IDH)1 and IDH2 in cholangiocarcinoma identified through broad-based tumor genotyping", Oncologist, 2012. 17(1): p. 72-79.

Wang, P., et al., "Mutations in isocitrate dehydrogenase 1 and 2 occur frequently in intrahepatic cholangiocarcinomas and share hypermethylation targets with glioblastomas", Oncogene, 2012, p. 1-10.

Sjoblom, T., et al., "The consensus coding sequences of human breast and colorectal cancers", Science, 2006. 314 (5797): p. 268-274.

Dang, L., S. Jin, and S.M. Su, "IDH mutations in glioma and acute myeloid leukemia", Trends Mol Med, 2010. 16(9): p. 387-397.

Suzuki, H., et al., "Mutational landscape and clonal architecture in grade II and III gliomas", Nat Genet, 2015. 47(5): p. 458-468.

Brat, D.J., et al., "Comprehensive, Integrative Genomic Analysis of Diffuse Lower-Grade Gliomas", N Engl J Med, 2015. 372(26): p. 2481-2498.

"Genomic and epigenomic landscapes of adult de novo acute myeloid leukemia", N Engl J Med, 2013. 368(22): p. 2059-2074.

Zhao, S., et al., "Glioma-derived mutations in IDH1 dominantly inhibit IDH1 catalytic activity and induce HIF-1alpha", Science, 2009. 324(5924): p. 261-265.

Dang, L., et al., "Cancer-associated IDH1 mutations produce 2-hydroxyglutarate", Nature, 2009. 462(7274): p. 739-744.

Xu, W., et al., "Oncometabolite 2-Hydroxyglutarate Is a Competitive Inhibitor of [alpha]-Ketoglutarate-Dependent Dioxygenases", Cancer Cell, 2011. 19(1): p. 17-30.

Wang, P., et al., "Oncometabolite D-2-Hydroxyglutarate Inhibits ALKBH DNA Repair Enzymes and Sensitizes IDH Mutant Cells to Alkylating Agents", Cell Rep, 2015. 13(11): p. 2353-2361.

Ma, S., et al., "D-2-hydroxyglutarate is essential for maintaining oncogenic property of mutant IDH-containing cancer cells but dispensable for cell growth", Oncotarget, 2015. 6(11): p. 8606-8620.

Luchman, H.A., et al., "An in vivo patient-derived model of endogenous IDH1-mutant glioma", Neuro Oncol, 2012. 14(2): p. 184-191.

Lopez-Valdez, German, et al., "Convenient access to isoindolinones via carbamoyl radical cyclization. Synthesis of cichorine and 4-hydroxyisoindolin-1-one natural products", Tetrahedron, Jan. 9, 2011(Jan. 9, 2011), 67(14), p. 2693-2701.

International Search Report of PCT/CN2017/092506.

Fanrong Mu et al: "Synthesis and Investigation of Conformationally Restricted Analogues of Lavendustin A as Cytotoxic Inhibitors of Tubulin Polymerization", Journal of Medicinal Chemistry, vol. 45, No. 21, Oct. 1, 2002, pp. 4774-4785,XP055656582,US ISSN:0022-2623, DOI: 10.1021/jm0202270; Abstract, compounds 32a, 32b, 34a, 34b.

The extended European Search Report of PCT Application No. PCT/CN2017/092506, dated Jan. 24, 2020.

* cited by examiner

ISO-CITRATE DEHYDROGENASE (IDH) INHIBITOR

FIELD OF THE DISCLOSURE

The present disclosure relates to compounds that inhibiting the conversion of α-ketoglutarate (α-KG) to 2-hydroxyglutarate (2-HG) such as D-2-HG, a pharmaceutical composition comprising the compound(s) as an active ingredient, and use of the compounds in the manufacture of medicaments for treating diseases associated with the conversion of α-KG to D-2-HG.

BACKGROUND

Isocitrate dehydrogenase (IDH) is an essential enzyme for cellular respiration in the tricarboxylic acid (TCA) cycle which catalyzes the oxidative decarboxylation of isocitrate, producing alpha-ketoglutarate (α-ketoglutarate, α-KG) and $CO_2$. In humans, IDH exists in three isoforms: IDH3 catalyzes the third step of the citric acid cycle while converting $NAD^+$ to NADH in the mitochondria. The isoforms IDH1 and IDH2 catalyze the same reaction outside the context of the citric acid cycle and use NADP+ as a cofactor instead of NAD+. They localize to the cytosol as well as the mitochondrion and peroxisome.

Specific mutations in the IDH1 have been found in several brain tumors including astrocytoma, oligodendroglioma and glioblastoma multiforme, with mutations found in nearly all cases of secondary glioblastomas, which develop from lower-grade gliomas, but rarely in primary high-grade glioblastoma multiforme. Patients whose tumor had an IDH1 mutation had longer survival ["An integrated genomic analysis of human glioblastoma multiforme", Parsons, D. W., et al., Science, (2008); "Analysis of the IDH1 codon 132 mutation in brain tumors", Balss, J., et al., Acta Neuropathol, (2008); Bleeker, F. E., et al., "IDH1 mutations at residue p.R132 (IDH1(R132)) occur frequently in high-grade gliomas but not in other solid tumors", Hum Mutat, (2009)]. IDH1 and IDH2 mutations occur before p53 mutation and the loss of 1p/19q chromosomes and are believed to be the first event of gliomagenesis ["IDH1 mutations are early events in the development of astrocytomas and oligodendrogliomas", Watanabe, T., et al., Am J Pathol, (2009); "Mutational landscape and clonal architecture in grade II and III gliomas", Suzuki, H., et al., Nat Genet, (2015); "Comprehensive, Integrative Genomic Analysis of Diffuse Lower-Grade Gliomas", Brat, D. J., et al., N Engl J Med, (2015)]. Furthermore, mutations of IDH2 and IDH1 were found in up to 20% of cytogenetically normal acute myeloid leukemia (AML) ["Recurring mutations found by sequencing an acute myeloid leukemia genome", Mardis, E. R., et al., N Engl J Med, (2009)]. According to several independent follow up researches, the mutation rate of IDH1 and IDH2 in cytogenetic normal AML is around 20% ["Recurring mutations found by sequencing an acute myeloid leukemia genome", Mardis, E. R., et al., N Engl J Med, (2009); "Prognostic impact of IDH2 mutations in cytogenetically normal acute myeloid leukemia", Thol, F., et al., Blood, (2010); "Acquired mutations in the genes encoding IDH1 and IDH2 both are recurrent aberrations in acute myeloid leukemia: prevalence and prognostic value", Abbas, S., et al., Blood, (2010); "The prognostic significance of IDH1 mutations in younger adult patients with acute myeloid leukemia is dependent on FLT3/ITD status", Green, C. L., et al., Blood, (2010); "IDH1 mutations are detected in 6.6% of 1414 AML patients and are associated with intermediate risk karyotype and unfavorable prognosis in adults younger than 60 years and unmutated NPM1 status", Schnittger, S., et al., Blood, (2010); "Genomic and epigenomic landscapes of adult de novo acute myeloid leukemia", N Engl J Med, (2013)]. IDH mutation is also reported in other type of cancer, including 75% chondrosarcoma ["IDH1 and IDH2 mutations are frequent events in central chondrosarcoma and central and periosteal chondromas but not in other mesenchymal tumours", Amary, M. F., et al., J Pathol, (2011); "Ollier disease and Maffucci syndrome are caused by somatic mosaic mutations of IDH1 and IDH2", Amary, M. F., et al., Nat Genet, (2011)], 10-23% intrahepatic cholangiocarcinoma ["Frequent mutation of isocitrate dehydrogenase IDH1 and IDH2 in cholangiocarcinoma identified through broad-based tumor genotyping", Borger, D. R., et al., Oncologist, (2012); "Mutations in isocitrate dehydrogenase 1 and 2 occur frequently in intrahepatic cholangiocarcinomas and share hypermethylation targets with glioblastomas", Wang, P., et al., Oncogene, (2012)], and some patients of angioimmunoblastic T-Cell Lymphoma and melanoma ["The consensus coding sequences of human breast and colorectal cancers", Sjoblom, T., et al., Science, (2006)]. So far, IDH1 and IDH2 are the most frequently mutated metabolic enzyme genes in human cancer.

These mutations are known to further convert α-KG to 2-HG (e.g. D-2-HG). D-2-HG accumulates to very high concentrations which inhibits the function of enzymes that are dependent on alpha-ketoglutarate. This leads to a hypermethylated state of DNA and histones, which results in different gene expression that can activate oncogenes and inactivate tumor-suppressor genes. Ultimately, this may lead to the types of cancer disclosed above ["The consensus coding sequences of human breast and colorectal cancers", Sjoblom, T., et al., Science, (2006)].

It is therefore desired to develop an inhibitor which inhibiting the process of converting α-KG to D-2-HG.

SUMMARY

In one aspect, the present disclosure provides a compound represented by Formula (I):

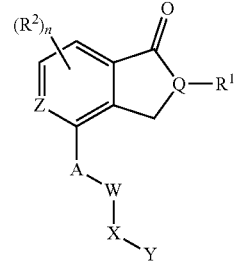

Formula (I)

or a pharmaceutically acceptable salt, ester, hydrate, solvates or stereoisomers thereof.

In another aspect, the present disclosure provides a method for manufacturing the compounds of Formula (I).

In another aspect, the present disclosure further provides a pharmaceutical composition comprising one or more compounds of Formula (I), pharmaceutically acceptable salts, hydrates, solvates or stereoisomers thereof.

In yet another aspect, the present disclosure provides use of the compounds of Formula (I), pharmaceutically acceptable salts, hydrates, solvates or stereoisomers thereof, or pharmaceutical composition of the present disclosure in the manufacture of medicaments for treating diseases associated with the conversion of α-KG to D-2-HG, for example cancers.

In a further aspect, the present disclosure provides a method for inhibiting conversion of α-KG to D-2-HG.

In another aspect, the present disclosure provides a method for treating diseases associated with conversion of α-KG to D-2-HG by using the compounds of Formula (I), pharmaceutically acceptable salts, hydrates, solvates or stereoisomers thereof or the pharmaceutical composition of the present disclosure.

In another aspect, the present disclosure provides a method of inhibiting mutant IDH, wild-type IDH or both by using the compounds of Formula (I), pharmaceutically acceptable salts, hydrates, solvates or stereoisomers thereof or the pharmaceutical composition of the present disclosure.

DETAILED DESCRIPTION

Compounds

Figure 1:
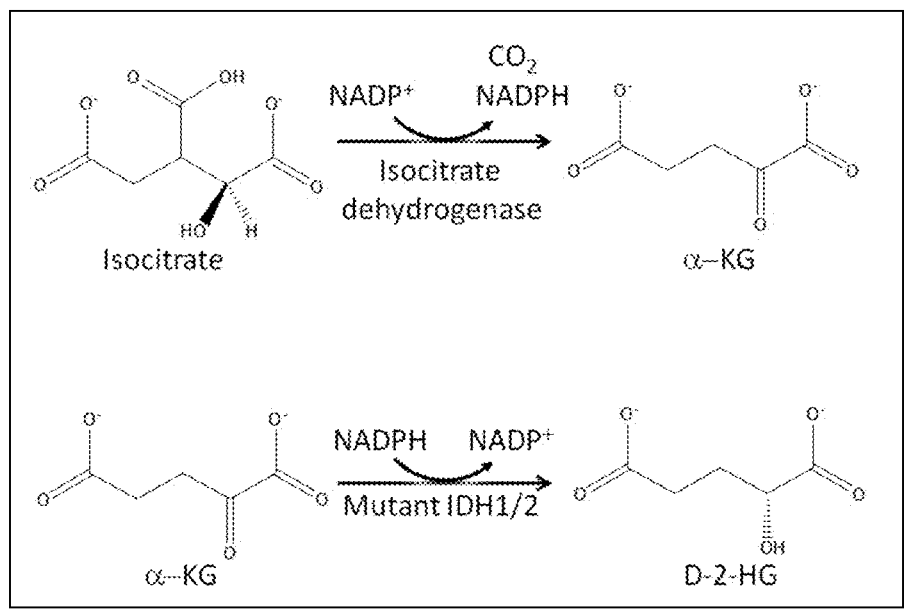
FIG. 1 shows representative reactions catalyzed by wild-type and mutant IDH1/2.

In one aspect, the present disclosure provides compounds of Formula (I):

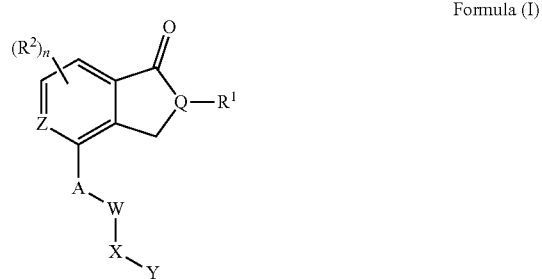

Formula (I)

and a pharmaceutically acceptable salt, ester, hydrate, or solvates or stereoisomers thereof, wherein:

Z and Q are independently selected from C and N;

A is O, S, or $NR^a$;

W is linear or branched $C_{1-6}$ alkylene;

X is $C_{6-12}$ aryl, $C_{6-12}$ heteroaryl, 3-10 membered saturated or unsaturated cycloalkyl, 3-10 membered saturated or unsaturated heterocycloalkyl;

Y is halo, cyano, $C_{1-12}$ alkyl, $C_{6-12}$ aryl, $C_{1-12}$ alkoxyl, $C_{6-12}$ aryloxyl, 3-10 membered saturated or unsaturated cycloalkyl, 3-10 membered saturated or unsaturated heterocycloalkyl, cycloalkylalkyl, heterocycloalkylalkyl, —C(O)OR$^b$, —C(O)NR$^c$R$^d$, which can be optionally mono- or independently multi-substituted by one or more of halogen, hydroxyl, cyano, $C_{1-12}$ alkyl, $C_{2-12}$ alkenyl, $C_{2-12}$ alkynyl, $C_{5-10}$ aryl, $C_{1-12}$ alkoxy, 3-10 membered saturated or unsaturated cycloalkyl, 3-10 membered heterocycloalkyl, or 3-10 membered heteroaryl, $C_{5-10}$ aryloxyl;

R$^1$ is $C_{1-12}$ alkyl, 3-10 membered saturated or unsaturated cycloalkyl, $C_{6-12}$ aralkyl, alkoxyalkyl, hydroxyalkyl, alkoxyaralkyl, or —NR$^e$R$^f$;

R$^2$ is hydrogen, —NR$^g$R$^h$, —C(O)OR$^b$, or —C(O)NR$^c$R$^d$;

R$^a$, R$^b$, R$^c$, R$^d$, R$^e$, R$^f$, R$^g$ and R$^h$ are independently selected from hydrogen, $C_{1-12}$ alkyl, 3-10 membered saturated or unsaturated cycloalkyl, $C_{6-12}$ aryl, which can be optionally mono- or independently multi-substituted by halogen, hydroxyl, cyano, $C_{1-12}$ alkyl, $C_{2-12}$ alkenyl, $C_{2-12}$ alkynyl, $C_{5-10}$ aryl, $C_{1-12}$ alkoxy, 3-10 membered saturated or unsaturated cycloalkyl, 3-10 membered heterocycloalkyl, or 3-10 membered heteroaryl, $C_{5-10}$ aryloxyl;

optionally R$^c$ and R$^d$ are taken together with the nitrogen atom to which they are bound to form a 4- to 8-membered heterocyclyl optionally comprising one or more additional heteroatoms selected from N, S, and O, optionally R$^g$ and R$^h$ are taken together with the nitrogen atom to which they are bound to form a 4- to 8-membered heterocyclyl optionally comprising one or more additional heteroatoms selected from N, S, and O;

n is 0, 1 or 2.

In some embodiments, Z is N.

In some embodiments, Q is N.

In some embodiments, A is NR$^a$. In some embodiments, A is NH.

In some embodiments, the compounds of the present disclosure are represented by Formula (Ia):

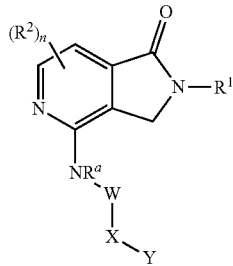

Formula (Ia)

and a pharmaceutically acceptable salt, ester, hydrate, solvates or stereoisomers thereof, wherein, W is linear or branched $C_{1-6}$ alkylene;

X is $C_{6-12}$ aryl, $C_{6-12}$ heteroaryl, 3-10 membered saturated or unsaturated cycloalkyl, 3-10 membered saturated or unsaturated heterocycloalkyl;

Y is halo, cyano, $C_{1-12}$ alkyl, $C_{6-12}$ aryl, $C_{1-12}$ alkoxyl, $C_{6-12}$ aryloxyl, 3-10 membered saturated or unsaturated cycloalkyl, 3-10 membered saturated or unsaturated heterocycloalkyl, cycloalkylalkyl, heterocycloalkylalkyl, —C(O)OR$^b$, —C(O)NR$^c$R$^d$, which can be optionally mono- or independently multi-substituted by one or more of halogen, hydroxyl, cyano, $C_{1-12}$ alkyl, $C_{2-12}$ alkenyl, $C_{2-12}$ alkynyl, $C_{5-10}$ aryl, $C_{1-12}$ alkoxy, 3-10 membered saturated or unsaturated cycloalkyl, 3-10 membered heterocycloalkyl, or 3-10 membered heteroaryl, $C_{5-10}$ aryloxyl;

R$^1$ is $C_{1-12}$ alkyl, 3-10 membered saturated or unsaturated cycloalkyl, $C_{6-12}$ aralkyl, alkoxyalkyl, hydroxyalkyl, alkoxyaralkyl, or —NR$^e$R$^f$;

R$^2$ is hydrogen, —NR$^g$R$^h$, —C(O)OR$^b$, or —C(O)NR$^c$R$^d$;

R$^a$, R$^b$, R$^c$, R$^d$, R$^e$, R$^f$, R$^g$ and R$^h$ are independently selected from hydrogen, $C_{1-12}$ alkyl, 3-10 membered saturated or unsaturated cycloalkyl, $C_{6-12}$ aryl, which can be optionally mono- or independently multi-substituted by halogen, hydroxyl, cyano, $C_{1-12}$ alkyl, $C_{2-12}$ alkenyl, $C_{2-12}$ alkynyl, $C_{5-10}$ aryl, $C_{1-12}$ alkoxy, 3-10 membered saturated or unsaturated cycloalkyl, 3-10 membered heterocycloalkyl, or 3-10 membered heteroaryl, $C_{5-10}$ aryloxyl;

optionally R$^c$ and R$^d$ are taken together with the nitrogen atom to which they are bound to form a 4- to 8-membered heterocyclyl optionally comprising one or more additional heteroatoms selected from N, S, and O, optionally R$^g$ and R$^h$ are taken together with the nitrogen atom to which they are bound to form a 4- to 8-membered heterocyclyl optionally comprising one or more additional heteroatoms selected from N, S, and O;

n is 0, 1 or 2.

In some embodiments, A in Formula (I) is NR$^a$. In some embodiments, R$^a$ in Formula (I) or Formula (Ia) is hydrogen.

In some embodiments, W in Formula (I) or Formula (Ia) is branched $C_{1-3}$ alkylene. In some embodiments, W in Formula (I) or Formula (Ia) is methylene, ethylene, or propylene. In some embodiments, W is 1,1-ethylene, 1,2-ethylene, 1,1-propylene, 1,2-propylene, 1,3-propylene, or 2,2-propylene. In some embodiments, W is 1,1-ethylene.

In some embodiments, X in Formula (I) or Formula (Ia) is $C_{6-12}$ aryl or $C_{6-12}$ heteroaryl. In some embodiments, X is phenyl, pyridinyl or pyrazolyl.

In some embodiments, Y in Formula (I) or Formula (Ia) is selected from the group consisting of:

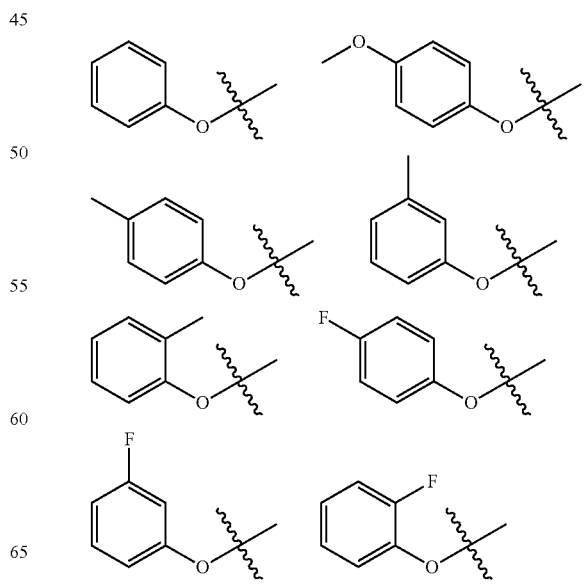

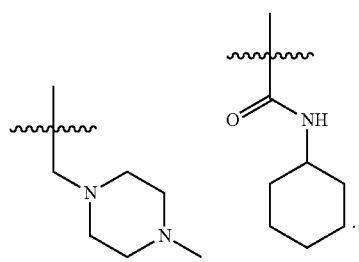

In some embodiments, the compounds of the present disclosure can have a (R)-configuration, a (S)-configuration or a mixture thereof.

In particular, the compounds of Formula (I) or Formula (Ia) of the present disclosure can be the following compounds 1-37:

| Compound No. | Structure and Nomenclature |
| --- | --- |
| 1 | 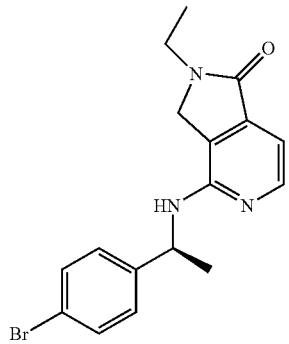 [SMILES: CCN1Cc2c(ccnc2N[C@@H](C)c2ccc(Br)cc2)C1=O]<br>(S)-4-(1-(4-bromophenyl)ethylamino)-2-ethyl-2,3-dihydro-1H-pyrrolo[3,4-c]pyridin-1-one |
| 2 | 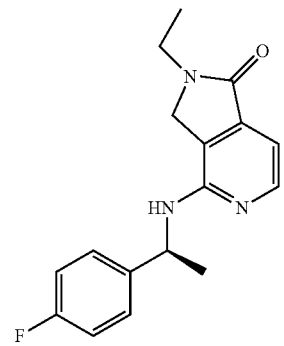 [SMILES: CCN1Cc2c(ccnc2N[C@@H](C)c2ccc(F)cc2)C1=O]<br>(S)-2-ethyl-4-(1-(4-fluorophenyl)ethylamino)-2,3-dihydro-1H-pyrrolo[3,4-c]pyridin-1-one |
| 3 | 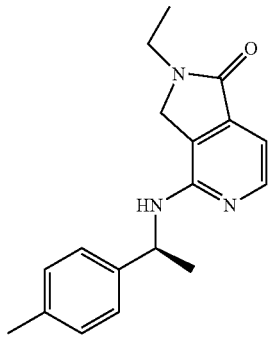 [SMILES: CCN1Cc2c(ccnc2N[C@@H](C)c2ccc(C)cc2)C1=O]<br>(S)-2-ethyl-4-(1-p-tolylethylamino)-2,3-dihydro-1H-pyrrolo[3,4-c]pyridin-1-one |
| 4 | 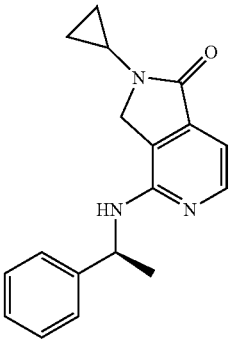 [SMILES: C[C@H](Nc1nccc2c1CN(C1CC1)C2=O)c1ccccc1]<br>(S)-2-cyclopropyl-4-(1-phenylethylamino)-2,3-dihydro-1H-pyrrolo[3,4-c]pyridin-1-one |
| 5 | 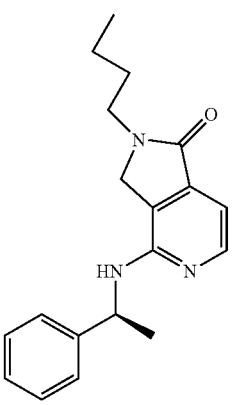 [SMILES: CCCCN1Cc2c(ccnc2N[C@@H](C)c2ccccc2)C1=O]<br>(S)-2-butyl-4-(1-phenylethylamino)-2,3-dihydro-1H-pyrrolo[3,4-c]pyridin-1-one |

| Compound No. | Structure and Nomenclature |
|---|---|
| 6 | 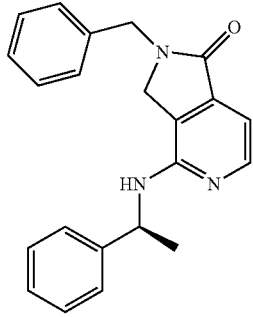 [SMILES: C[C@H](Nc1nccc2c1CN(Cc1ccccc1)C2=O)c1ccccc1]<br>(S)-2-benzyl-4-(1-phenylethylamino)-2,3-dihydro-1H-pyrrolo[3,4-c]pyridin-1-one |
| 7 | 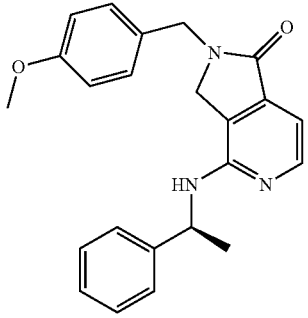 [SMILES: COc1ccc(CN2Cc3c(ccnc3N[C@@H](C)c3ccccc3)C2=O)cc1]<br>(S)-2-(4-methoxybenzyl)-4-(1-phenylethylamino)-2,3-dihydro-1H-pyrrolo[3,4-c]pyridin-1-one |
| 8 | 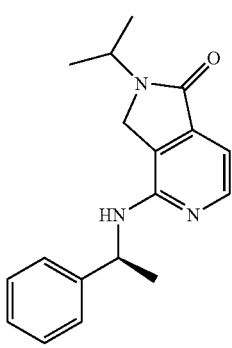 [SMILES: CC(C)N1Cc2c(ccnc2N[C@@H](C)c2ccccc2)C1=O]<br>(S)-2-isopropyl-4-(1-phenylethylamino)-2,3-dihydro-1H-pyrrolo[3,4-c]pyridin-1-one |
| 9 | 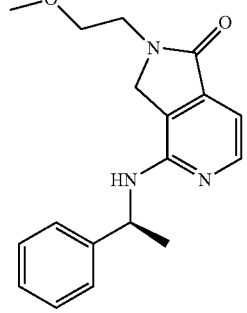<br>(S)-2-(2-methoxyethyl)-4-(1-phenylethylamino)-2,3-dihydro-1H-pyrrolo[3,4-c]pyridin-1-one |
| 10 | 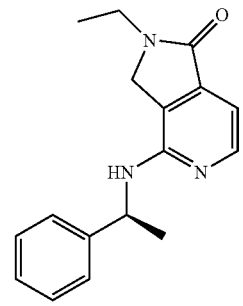 [SMILES: CCN1Cc2c(ccnc2N[C@@H](C)c2ccccc2)C1=O]<br>(S)-2-ethyl-4-(1-phenylethylamino)-2,3-dihydro-1H-pyrrolo[3,4-c]pyridin-1-one |
| 11 | 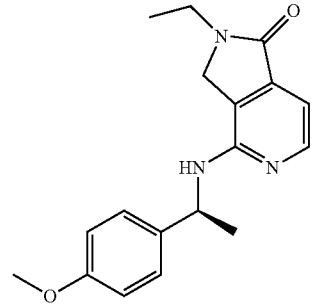 [SMILES: CCN1Cc2c(ccnc2N[C@@H](C)c2ccc(OC)cc2)C1=O]<br>(S)-2-ethyl-4-(1-(4-methoxyphenyl)ethylamino)-2,3-dihydro-1H-pyrrolo[3,4-c]pyridin-1-one |
| 12 | 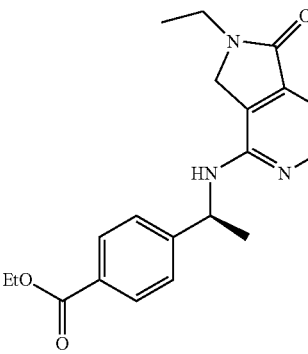<br>(S)-ethyl 4-(1-(2-ethyl-1-oxo-2,3-dihydro-1H-pyrrolo[3,4-c]pyridin-4-yl amino) ethyl) benzoate |

| Compound No. | Structure and Nomenclature |
|---|---|
| 13 | 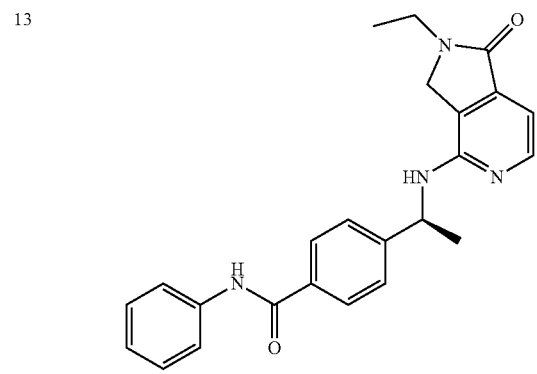<br>(S)-4-(1-(2-ethyl-1-oxo-2,3-dihydro-1H-pyrrolo[3,4-c]pyridin-4-ylamino)ethyl)-N-phenylbenzamide |
| 14 | 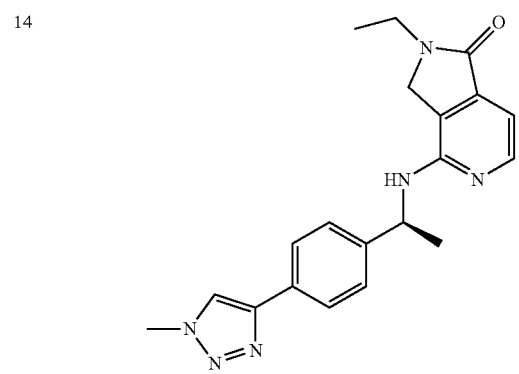<br>(S)-2-ethyl-4-(1-(4-(1-methyl-1H-1,2,3-triazol-4-yl)phenyl)ethylamino)-2,3-dihydro-1H-pyrrolo[3,4-c]pyridin-1-one |
| 15 | 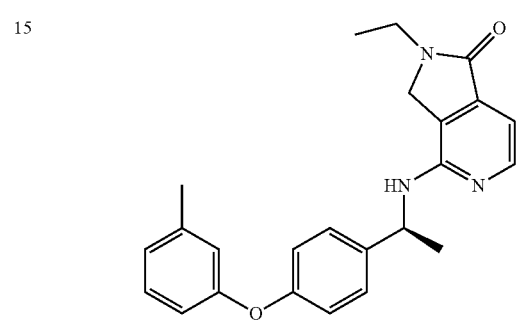<br>(S)-2-ethyl-4-(1-(4-(m-tolyloxy)phenyl)ethylamino)-2,3-dihydro-1H-pyrrolo[3,4-c]pyridin-1-one |
| 16 | <br>(S)-2-ethyl-4-(1-(4-(p-tolyloxy)phenyl)ethylamino)-2,3-dihydro-1H-pyrrolo[3,4-c]pyridin-1-one |
| 17 | 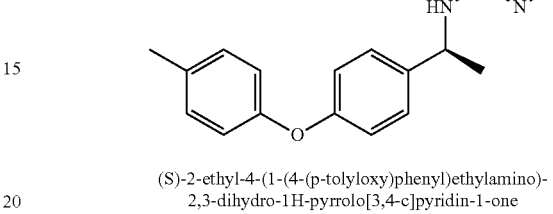<br>(S)-2-ethyl-4-(1-(4-(o-tolyloxy)phenyl)ethylamino)-2,3-dihydro-1H-pyrrolo[3,4-c]pyridin-1-one |
| 18 | 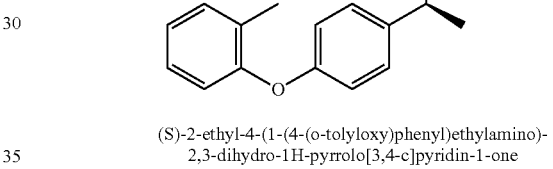<br>(S)-2-ethyl-4-(1-(4-phenoxyphenyl)ethylamino)-2,3-dihydro-1H-pyrrolo[3,4-c]pyridin-1-one |
| 19 | 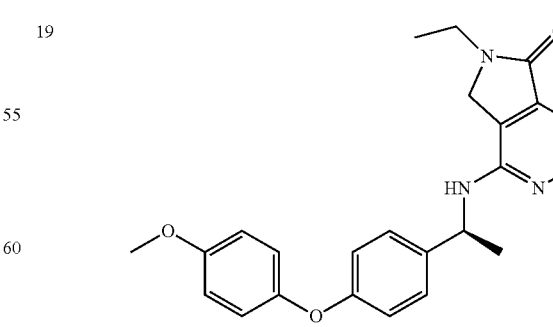<br>(S)-2-ethyl-4-(1-(4-(4-methoxyphenoxy)phenyl)ethylamino)-2,3-dihydro-1H-pyrrolo[3,4-c]pyridin-1-one |

| Compound No. | Structure and Nomenclature |
|---|---|
| 20 | 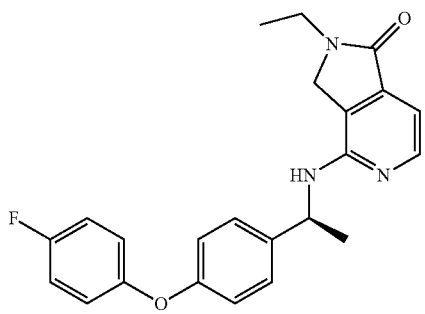 [SMILES: CCN1Cc2c(ccnc2N[C@@H](C)c2ccc(Oc3ccc(F)cc3)cc2)C1=O]
(S)-2-ethyl-4-(1-(4-(4-fluorophenoxy)phenyl)ethylamino)-2,3-dihydro-1H-pyrrolo[3,4-c]pyridin-1-one |
| 21 | 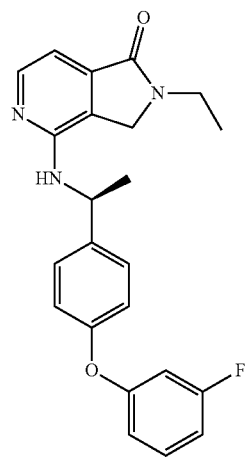 [SMILES: CCN1Cc2c(ccnc2N[C@@H](C)c2ccc(Oc3cccc(F)c3)cc2)C1=O]
(S)-2-ethyl-4-((1-(4-(3-fluorophenoxy)phenyl)ethyl)amino)-2,3-dihydro-1H-pyrrolo[3,4-c]pyridin-1-one |
| 22 | 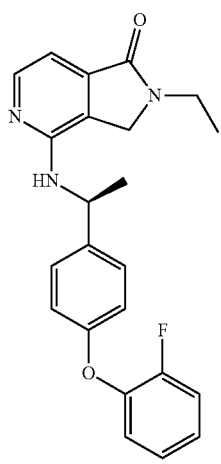 [SMILES: CCN1Cc2c(ccnc2N[C@@H](C)c2ccc(Oc3ccccc3F)cc2)C1=O]
(S)-2-ethyl-4-((1-(4-(2-fluorophenoxy)phenyl)ethyl)amino)-2,3-dihydro-1H-pyrrolo[3,4-c]pyridin-1-one |
| 23 | 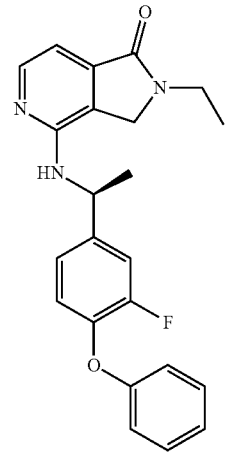 [SMILES: CCN1Cc2c(ccnc2N[C@@H](C)c2ccc(Oc3ccccc3)c(F)c2)C1=O]
(S)-2-ethyl-4-((1-(3-fluoro-4-phenoxyphenyl)ethyl)amino)-2,3-dihydro-1H-pyrrolo[3,4-c]pyridin-1-one |
| 24 | 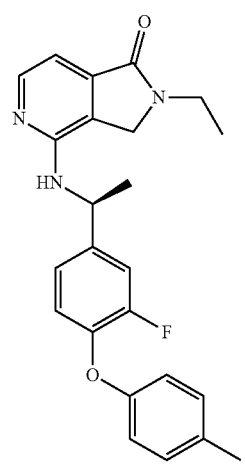 [SMILES: CCN1Cc2c(ccnc2N[C@@H](C)c2ccc(Oc3ccc(C)cc3)c(F)c2)C1=O]
(S)-2-ethyl-4-((1-(3-fluoro-4-(p-tolyloxy)phenyl)ethyl)amino)-2,3-dihydro-1H-pyrrolo[3,4-c]pyridin-1-one |

| Compound No. | Structure and Nomenclature |
|---|---|
| 25 | 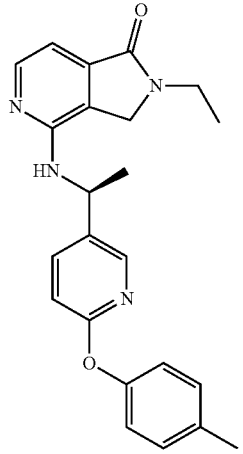 [SMILES: CCN1Cc2c(ccnc2N[C@@H](C)c2ccc(Oc3ccc(C)cc3)nc2)C1=O]<br>(S)-2-ethyl-4-((1-(6-(p-tolyloxy)pyridin-3-yl)ethyl)amino)-2,3-dihydro-1H-pyrrolo[3,4-c]pyridin-1-one |
| 26 | 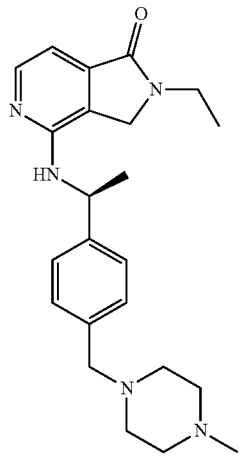 [SMILES: CCN1Cc2c(ccnc2N[C@@H](C)c2ccc(CN3CCN(C)CC3)cc2)C1=O]<br>(S)-2-ethyl-4-((1-(4-((4-methylpiperazin-1-yl)methyl)phenyl)ethyl)amino)-2,3-dihydro-1H-pyrrolo[3,4-c]pyridin-1-one |

| Compound No. | Structure and Nomenclature |
|---|---|
| 27 | 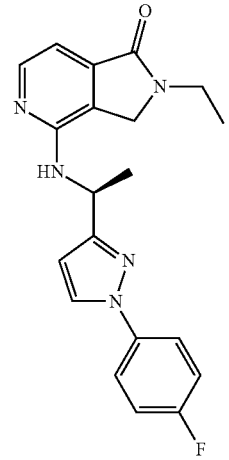 [SMILES: CCN1Cc2c(ccnc2N[C@@H](C)c2ccn(-c3ccc(F)cc3)n2)C1=O]<br>(S)-2-ethyl-4-((1-(1-(4-fluorophenyl)-1H-pyrazol-3-yl)ethyl)amino)-2,3-dihydro-1H-pyrrolo[3,4-c]pyridin-1-one |
| 28 | 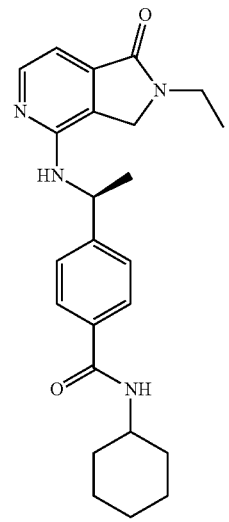 [SMILES: CCN1Cc2c(ccnc2N[C@@H](C)c2ccc(C(=O)NC3CCCCC3)cc2)C1=O]<br>(S)-N-cyclohexyl-4-(1-((2-ethyl-1-oxo-2,3-dihydro-1H-pyrrolo[3,4-c]pyridin-4-yl)amino)ethyl)benzamide |

| Compound No. | Structure and Nomenclature |
|---|---|
| 29 | 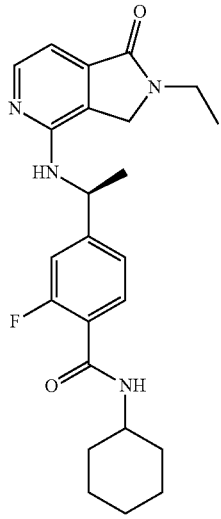 [SMILES: CCN1Cc2c(ccnc2N[C@@H](C)c2ccc(C(=O)NC3CCCCC3)c(F)c2)C1=O]<br>(S)-N-cyclohexyl-4-(1-((2-ethyl-1-oxo-2,3-dihydro-1H-pyrrolo[3,4-c]pyridin-4-yl)amino)ethyl)-2-fluorobenzamide |
| 30 | 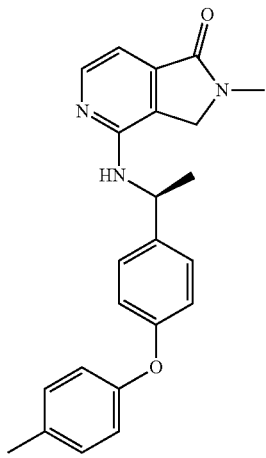<br>(S)-2-methyl-4-((1-(4-(p-tolyloxy)phenyl)ethyl)amino)-2,3-dihydro-1H-pyrrolo[3,4-c]pyridin-1-one |
| 31 | 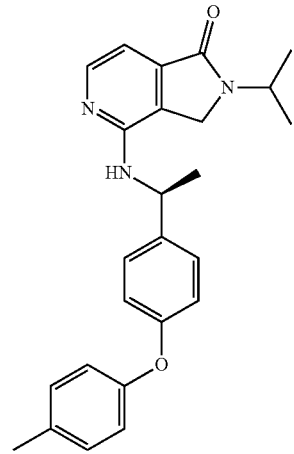 [SMILES: Cc1ccc(Oc2ccc([C@H](C)Nc3nccc4c3CN(C(C)C)C4=O)cc2)cc1]<br>(S)-2-isopropyl-4-((1-(4-(p-tolyloxy)phenyl)ethyl)amino)-2,3-dihydro-1H-pyrrolo[3,4-c]pyridin-1-one |
| 32 | 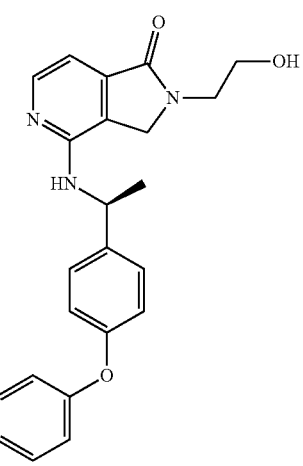<br>(S)-2-(2-hydroxyethyl)-4-((1-(4-(p-tolyloxy)phenyl)ethyl)amino)-2,3-dihydro-1H-pyrrolo[3,4-c]pyridin-1-one |

| Compound No. | Structure and Nomenclature |
|---|---|
| 33 | 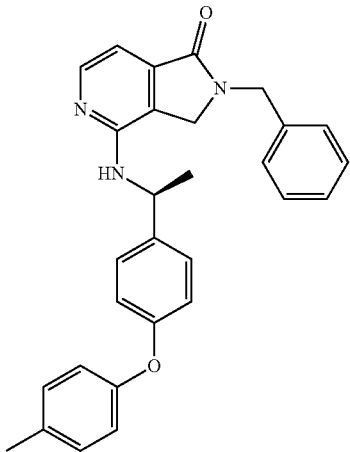 [SMILES: Cc1ccc(Oc2ccc([C@H](C)Nc3nccc4c3CN(Cc3ccccc3)C4=O)cc2)cc1]<br>(S)-2-benzyl-4-((1-(4-(p-tolyloxy)phenyl)ethyl)amino)-2,3-dihydro-1H-pyrrolo[3,4-c]pyridin-1-one |
| 34 | 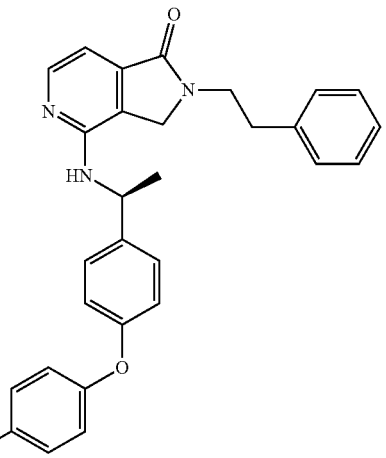<br>(S)-2-phenethyl-4-((1-(4-(p-tolyloxy)phenyl)ethyl)amino)-2,3-dihydro-1H-pyrrolo[3,4-c]pyridin-1-one |

| Compound No. | Structure and Nomenclature |
|---|---|
| 35 | 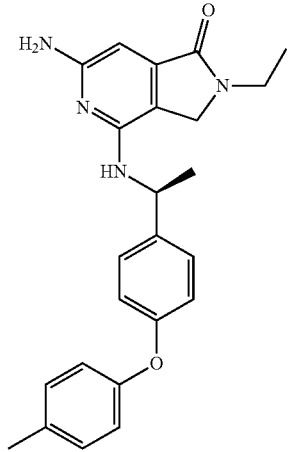 [SMILES: CCN1Cc2c(cc(N)nc2N[C@@H](C)c2ccc(Oc3ccc(C)cc3)cc2)C1=O]<br>(S)-6-amino-2-ethyl-4-((1-(4-(p-tolyloxy)phenyl)ethyl)amino)-2,3-dihydro-1H-pyrrolo[3,4-c]pyridin-1-one |
| 36 | 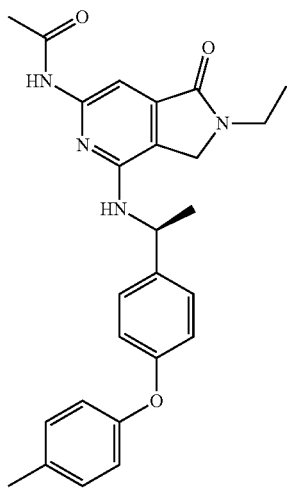 [SMILES: CCN1Cc2c(cc(NC(C)=O)nc2N[C@@H](C)c2ccc(Oc3ccc(C)cc3)cc2)C1=O]<br>(S)-N-(2-ethyl-1-oxo-4-((1-(4-(p-tolyloxy)phenyl)ethyl)amino)-2,3-dihydro-1H-pyrrolo[3,4-c]pyridin-6-yl)acetamide |

-continued

| Compound No. | Structure and Nomenclature |
|---|---|
| 37 | 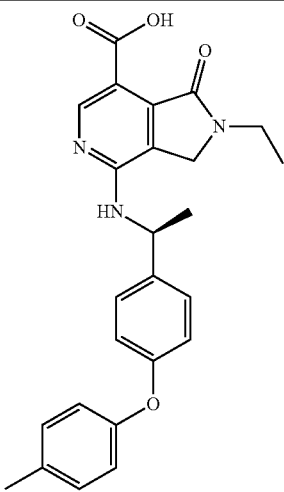<br>(S)-2-ethyl-1-oxo-4-((1-(4-(p-tolyloxy)phenyl)ethyl)amino)-2,3-dihydro-1H-pyrrolo[3,4-c]pyridine-7-carboxylic acid |

Various features of the present disclosure that are, for brevity, disclosed in the context of a single embodiment, can also be provided separately or in any suitable subcombination.

As used herein, the term "substituted", when refers to a chemical group, means the chemical group has one or more hydrogen atoms that is/are removed and replaced by substituents. As used herein, the term "substituent" has the ordinary meaning known in the art and refers to a chemical moiety that is covalently attached to, or if appropriate fused to, a parent group. As used herein, the term "optionally substituted" means that the chemical group may have no substituents (i.e. unsubstituted) or may have one or more substituents (i.e. substituted). It is to be understood that substitution at a given atom is limited by valency.

As used herein, the term "$C_{i\text{-}j}$" indicates a range of the carbon atoms numbers, wherein i and j are integers and the range of the carbon atoms numbers includes the endpoints (i.e. i and j) and each integer point in between, and wherein i ∈ {1, 2, 3, 4, 5, 6, 7, 8, 9, or 10}, j is greater than i, j ∈ {2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40}. For examples, $C_{1\text{-}6}$ indicates a range of one to six carbon atoms, including one carbon atom, two carbon atoms, three carbon atoms, four carbon atoms, five carbon atoms and six carbon atoms.

As used herein, the term "alkyl", whether as part of another term or used independently, refers to a saturated or unsaturated hydrocarbon group that may be straight-chain or branched-chain. The term "$C_{i\text{-}j}$ alkyl" refers to an alkyl having i to j carbon atoms. In some embodiments, the alkyl group contains 1 to 12, 1 to 8, 1 to 6, 1 to 4, 1 to 3, or 1 to 2 carbon atoms. Examples of saturated alkyl group include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. Examples of unsaturated alkyl groups include, but are not limited to, chemical groups such as ethenyl, n-propenyl, isopropenyl, n-butenyl, sec-butenyl, ethynyl, propyn-1-yl, propyn-2-yl, and the like.

As used herein, the term "alkylene", whether as part of another term or used independently, refers to a divalent alkyl. Examples of alkylene groups include, but are not limited to, methylene, 1,1-ethylene, 1,2-ethylene, 1,1-propylene, 1,2-propylene, 1,3-propylene, 2,2-propylene, and the like.

As used herein, the term "aryl" or "aromatic", whether as part of another term or used independently, refers to a mono- or polycyclic carbocyclic ring system radicals with alternating double and single bonds between carbon atoms forming the rings. In some embodiments, the aryl ring systems have 5 to 12, 5 to 10, or 5 to 8, 6 to 12, 6 to 10, or 6 to 8 carbon atoms in one or more rings. Examples of aryl groups include, but are not limited to, chemical groups such as phenyl, naphthyl, tetrahydronaphthyl, indanyl, idenyl and the like.

As used herein, the term "aralkyl" or "arylalkyl", whether as part of another term or used independently, refers to a group of formula -alkyl-aryl. The term "$C_{i\text{-}j}$ aralkyl" refers to aralkyl with a total carbon number between i to j. In some embodiments, the alkyl moiety has 1 to 6, 1 to 4, 1 to 3, or 1 to 2 carbon atoms. In some embodiments, the aralkyl group has 6-12, 6-11, 6-10, 6-9, 6-8, or 6-7 carbon atoms. Examples of aralkyl groups include, but are not limited to, various -alkyl-benzenes and -alkyl-naphthalenes.

As used herein, the term "alkenyl" refers to a straight or branched hydrocarbon chain having one or more double bonds. The term "$C_{i\text{-}j}$ alkenyl" refers to alkenyl with a total carbon number between i to j. In some embodiments, the alkenyl group has 2-12, 2-11, 2-10, 2-9, 2-8, 2-7, 2-6, 2-5, 2-4 or 2-3 carbon atoms. Examples of alkenyl groups include, but are not limited to, allyl, propenyl, 2-butenyl, 3-hexenyl, 3-octenyl and the like. One of the double bond carbons may optionally be the point of attachment of the alkenyl substituent.

As used herein, the term "alkynyl" refers to a straight or branched hydrocarbon chain having one or more triple bonds. The term "$C_{i\text{-}j}$ alkynyl" refers to alkynyl with a total carbon number between i to j. In some embodiments, the alkynyl group has 2-12, 2-11, 2-10, 2-9, 2-8, 2-7, 2-6, 2-5, 2-4 or 2-3 carbon atoms. Examples of alkynyl groups include, but are not limited to, ethynyl, propargyl, 3-hexynyl and the like. One of the triple bond carbons may optionally be the point of attachment of the alkynyl substituent.

As used herein, the term "cycloalkyl", whether as part of another term or used independently, refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. In some embodiments, the cycloalkyl is saturated cycloalkyl. The term "i-j membered cycloalkyl" refers to cycloalkyl having i to j ring-forming members. Cycloalkyl groups can have 3, 4, 5, 6, 7, 8 ring-forming carbons ($C_3$-8). Examples of cycloalkyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, and the like. In some embodiments, a cycloalkyl used herein may be fused (i.e., having a bond in common with) with one or more aromatic rings, for example, benzo or thienyl derivatives of cyclopentane, cyclohexane, and the like. In some embodiments, a cycloalkyl group containing a fused aromatic ring can be attached through any ring-forming atom including a ring-forming atom of the fused aromatic ring.

As used herein, the term "heterocycloalkyl" refers to cycloalkyl group wherein at least one ring atom in the ring systems is a heteroatom, and the remainder of the ring atoms being carbon atoms. The term "i-j membered heterocycloalkyl" refers to heterocycloalkyl having i to j ring-forming members. In addition, the ring may also have one or more double bonds, but not have a completely conjugated system. In some embodiments, the heterocycloalkyl is saturated heterocycloalkyl. Examples of heteroatoms include, but are not limited to, oxygen, sulfur, nitrogen, phosphorus, and the like. In some embodiments, heterocycloalkyl has 3 to 8, 3 to 6, or 4 to 6 ring-forming carbons. Examples of heterocycloalkyl include, but are not limited to, azetidine, aziridine, pyrrolidyl, piperidyl, piperazinyl, morpholinyl, thiomorpholinyl, homopiperazinyl, and the like.

As used herein, the term "carbocyclyl" refers to any ring system in which all the ring atoms are carbon and which contains between three and twelve ring carbon atoms, between three and ten carbon atoms, between three and eight carbon atoms and between four to eight carbon atoms. Carbocyclyl groups may be saturated or partially unsaturated, but do not include aromatic rings. Examples of carbocyclyl groups include monocyclic, bicyclic, and tricyclic ring systems. Other carbocylcyl groups include bridged ring systems (e.g. bicyclo[2,2,1]heptenyl). A specific example of a carbocyclyl group is a cycloalkyl.

As used herein, the term "heterocyclyl" refers to a carbocyclyl group wherein one or more (e.g. 1, 2 or 3) ring atoms are replaced by heteroatoms which include, but are not limited to, oxygen, sulfur, nitrogen, phosphorus, and the like. A specific example of a heterocyclyl group is a cycloalkyl group wherein one or more ring atoms are replaced by heteroatoms. Exemplary heterocyclyl groups containing one hetero atom include pyrrolidine, tetrahydrofuran and piperidine, and exemplary heterocyclyl groups containing two hetero atoms include morpholine and piperazine. A further specific example of a heterocyclyl group is a cycloalkenyl group wherein one or more ring atoms are replaced by heteroatoms.

As used herein, the term "alkoxy", whether as part of another term or used independently, refers to a group of formula —O-alkyl. The term "$C_{i-j}$ alkoxy" means that the alkyl moiety of the alkoxy group has i to j carbon atoms. In some embodiments, the alkyl moiety has 1 to 6, 1 to 5, 1 to 4, 1 to 3 or 1 to 2 carbon atoms. Examples of alkoxy groups include, but are not limted to, methoxy, ethoxy, propoxy (e.g., n-propoxy and isopropoxy), t-butoxy, and the like.

As used herein, the term "aryloxyl" refers to a group of formula —O-aryl, wherein the aryl group is as previously disclosed. "$C_{i-j}$ aryloxyl" means that the aryl moiety of the aryloxyl group has i to j carbon atoms. In some embodiments, the aryl moiety has 5 to 10, 5 to 8, or 5 to 6 carbon atoms.

As used herein, the term "n membered", wherein n is an integer typically employed in combination with a ring system to describe the number of ring-forming atoms in the ring system. For example, piperidinyl is an example of a 6 membered heterocycloalkyl ring, pyrazolyl is an example of a 5 membered heteroaryl ring, pyridyl is an example of a 6 membered heteroaryl ring, and 1,2,3,4-tetrahydro-naphthalene is an example of a 10 membered cycloalkyl group.

As used herein, the term "heteroaryl" refers to an aryl group wherein at least one ring atom in the aromatic ring is a heteroatom, and the remainder of the ring atoms being carbon atoms. The term "i-j membered heteroaryl" refers to heteroaryl having i to j ring-forming members. Examples of heteroatoms include, but are not limited to, oxygen, sulfur, nitrogen, phosphorus, and the like. In some embodiments, heteroaryl can have 5 to 10, 5 to 8, or 5 to 6 ring-forming members. In some embodiments, heteroaryl is 5 membered or 6 membered heteroaryl. Examples of heteroaryl include, but are not limited to, furanyl, thienyl, pyridyl, pyrrolyl, N-lower alkyl pyrrolyl, pyridyl-N-oxide, pyrimidyl, pyrazinyl, imidazolyl, indolyl and the like.

In some embodiments, a 5 membered heteroaryl can be a heteroaryl with a ring having five ring atoms, wherein one or more (e.g., 1, 2, or 3) ring atoms can be independently selected from N, O, P, and S. Exemplary 5 membered heteroaryl are thienyl, furyl, pyrrolyl, imidazolyl, thiazolyl, oxazolyl, pyrazolyl, isothiazolyl, isoxazolyl, 1,2,3-triazolyl, 1,2,4-triazolyl, 1,3,4-triazolyl, tetrazolyl, 1,2,3-thiadiazolyl, 1,2,4-thiadiazolyl, 1,3,4-thiadiazolyl, 1,2,3-oxadiazolyl, 1,2,4-oxadiazolyl, 1,3,4-oxadiazolyl and the like.

In some embodiments, a 6 membered heteroaryl is can be a heteroaryl with a ring having six ring atoms, wherein one or more (e.g., 1, 2, or 3) ring atoms can be independently selected from N, O, P, and S. Exemplary 6 membered heteroaryl are pyridyl, pyrazinyl, pyrimidinyl, triazinyl and pyridazinyl.

As used herein the terms "halo" and "halogen" refer to an atom selected from fluorine, chlorine, bromine and iodine.

As used herein the terms "cyano" refer to a group of formula —CN.

As used herein, the term "hydroxyl" refers to a group of formula —OH.

As used herein, the term "compound" is meant to include all stereoisomers (e.g., enantiomers and diastereomers), geometric iosomers, tautomers, and isotopes of the structures depicted. Compounds herein identified by name or structure as one particular tautomeric form are intended to include other tautomeric forms unless otherwise specified.

The compounds disclosed herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, carbon-carbon double bonds, and the like can also be present in the compounds disclosed herein, and all such stable isomers are contemplated in the present disclosure. Cis and trans geometric isomers of the compounds of the present application are disclosed and may be isolated as a mixture of isomers or as separated isomeric forms.

In some embodiments, the compounds disclosed herein have the (R)-configuration. In some embodiments, the compounds disclosed herein have the (S)-configuration.

Compounds disclosed herein also include tautomeric forms. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds disclosed herein can also include all isotopes of atoms occurring in the intermediates or final compounds.

Isotopes include those atoms having the same atomic number but different mass numbers. For example, isotopes of hydrogen include protium, deuterium and tritium. In some embodiments, the isotope of hydrogen is protium and deuterium.

The compounds of the present disclosure may also be used as forms of pharmaceutically acceptable salts, hydrates, solvates or metabolites. The pharmaceutically acceptable salts comprise alkali salts of inorganic and organic acids, the acids comprise but not limit to hydrochloric acid, hydrobromic acid, sulfuric acid, phosphoric acid, methanesulfonic acid, ethylsulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid. When the compounds of the present disclosure comprise acidic functional groups such as carboxyl, the suitable pharmaceutically acceptable carboxylic cations are well-known for a person skilled in the art, including alkali, alkaline earth, ammonium, quaternary ammonium cations.

Unless otherwise specified, "IDH" or "wild-type IDH" refers to normal IDH enzymes which catalyze the conversion of isocitrate to α-KG Exemplary normal IDH enzymes include:

```
Human IDH1 protein
    (NCBI accession number: O75874.2, SEQ ID NO: 1)
  1    mskkisggsv vemqgdemtr iiwelikekl ifpyveldlh
       sydlgienrd atndqvtkda 61    aeaikkhnvg vkcatitpde krveefklkq mwkspngtir
       nilggtvfre aiickniprl 121    vsgwvkpiii grhaygdqyr atdfvvpgpg kveitytpsd
       gtqkvtylvh nfeegggvam 181    gmynqdksie dfahssfqma lskgwplyls tkntilkkyd
       grfkdifqei ydkqyksqfe 241    aqkiwyehrl iddmvaqamk seggfiwack nydgdvqsds
       vaqgygslgm mtsvlvcpdg 301    ktveaeaahg tvtrhyrmyq kgqetstnpi asifawtrgl
       ahrakldnnk elaffanale 361    evsietieag fmtkdlaaci kglpnvqrsd ylntfefmdk
       lgenlkikla qakl Human IDH2 protein
    (NCBI accession number: P48735.2, SEQ ID NO: 2)
  1    magylrvvrs lcrasgsrpa wapaaltapt sqeqprrhya
       dkrikvakpv vemdgdemtr 61    iiwqfikekl ilphvdiqlk yfdlglpnrd qtddqvtids
       alatqkysva vkcatitpde 121    arveefklkk mwkspngtir nilggtvfre piickniprl
       vpgwtkpiti grhahgdqyk 181    atdfvadrag tfkmvftpkd gsgvkewevy nfpaggvgmg
       myntdesisg fahscfqyai 241    qkkwplymst kntilkaydg rfkdifqeif dkhyktdfdk
       nkiwyehrli ddmvaqvlks 301    sggfvwackn ydgdvqsdil aqgfgslglm tsvlvcpdgk
       tieaeaahgt vtrhyrehqk 361    grptstnpia sifawtrgle hrgkldgnqd lirfaqmlek
       vcvetvesga mtkdlagcih 421    glsnvklneh flnttdfldt iksnldralg rq
```

As used herein, the term "IDH mutations" refers to the any mutations to the IDH enzymes which enable the "IDH mutants", "mutant IDH" or "mutated IDH" to catalyze the conversion of α-KG to D-2-HG In some embodiments, "mutant IDH" catalyses both the conversion of α-KG to D-2-HG and the conversion of isocitrate to α-KG Such mutations include but are not limited to, R132H, R132C, R132QG R132L, R132S in IDH1; or R172K, R172M, R172W in IDH2.

In some embodiments, compounds of the present disclosure inhibit the conversion of α-KG to D-2-HG In some embodiments, compounds of present disclosure inhibit the conversion of isocitrate to α-KG. In some embodiments, compounds of present disclosure inhibit both the conversion of α-KG to D-2-HG and the conversion of isocitrate to α-KG In some embodiments, compounds of the present disclosure can selectively inhibit conversion of α-KG to D-2-HG but not conversion of isocitrate to α-KG In some embodiments, compounds of the present disclosure inhibit mutant IDH. In some embodiments, compounds of present disclosure inhibit wild-type IDH. In some embodiments, compounds of present disclosure inhibit both mutant IDH and wild-type IDH. In some embodiments, compounds of the present disclosure can selectively inhibit mutant IDH but not wild-type IDH.

In some embodiments, compounds of the present disclosure inhibit wild-type IDH and/or mutant IDH with an $IC_{50}$ value of 0.01-1000 μM, preferably 0.01-500 μM, 0.01-100 μM, 0.01-80 μM, 0.01-50 μM, 0.01-40 μM, 0.01-30 μM, or 0.01-20 μM, more preferably 0.01-10 μM, 0.01-5 μM, or 0.01-1 μM.

As used herein, the term "selectively inhibit" means that the $IC_{50}$ of the compounds to wild-type IDH is at least 2 times, 3 times, 4 times, 5 times, preferably 10 times, 20 times, 30 times or 50 times higher than the $IC_{50}$ of the compounds to IDH mutant.

Synthetic Method

Synthesis of the compounds provided herein, including salts, esters, hydrates, or solvates or stereoisomers thereof, are illustrated in the below general synthetic schemes. The compounds provided herein can be prepared using any known organic synthesis techniques and can be synthesized according to any of numerous possible synthetic routes, and thus these schemes are illustrative only and are not meant to limit other possible methods that can be used to prepare the compounds provided herein. Additionally, the steps in the Schemes are for better illustration and can be changed as appropriate. The embodiments of the compounds in examples were synthesized in China for the purposes of research and potentially submission to regulatory agencies.

The reactions for preparing compounds of the disclosure can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by a skilled artisan.

Preparation of compounds of the disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G M. Wuts, Protective Groups in Organic Synthesis, 3rd Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs J. Combi. Chem. 2004, 6(6), 874-883, which is incorporated herein by reference in its entirety) and normal phase silica chromatography.

The intermediate compounds of Formula (Ia) can be synthesized as shown in Schemes 1 to 5, the compounds of Formula (Ia) can be synthesized as shown in Scheme 6 to 11.

Scheme 1: Synthesis of the intermediate of formula (Ia)

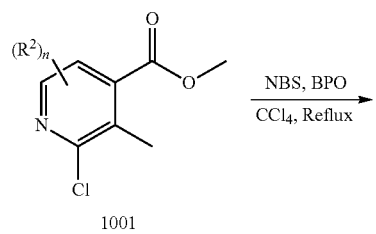

1001

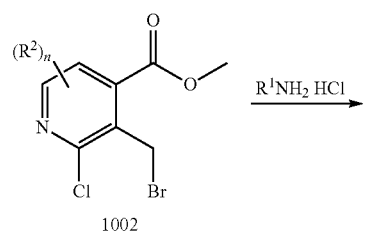

1002

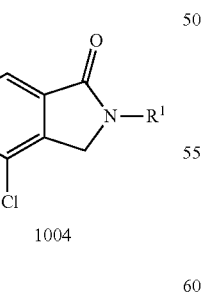

1003 → 1004

Step 1: Compound 1001 was reacted with NBS and BPO in CCl$_4$ to afford Compound 1002, wherein the definition of R$^2$ is as disclosed above.

Step 2: Compound 1002 was reacted with R$^1$NH$_2$ HCl in the presence of Cs$_2$CO$_3$ to give Compound 1004, wherein the definition of R$^1$ is as disclosed above.

Scheme 2: Synthesis of the intermediate of formula (Ia)

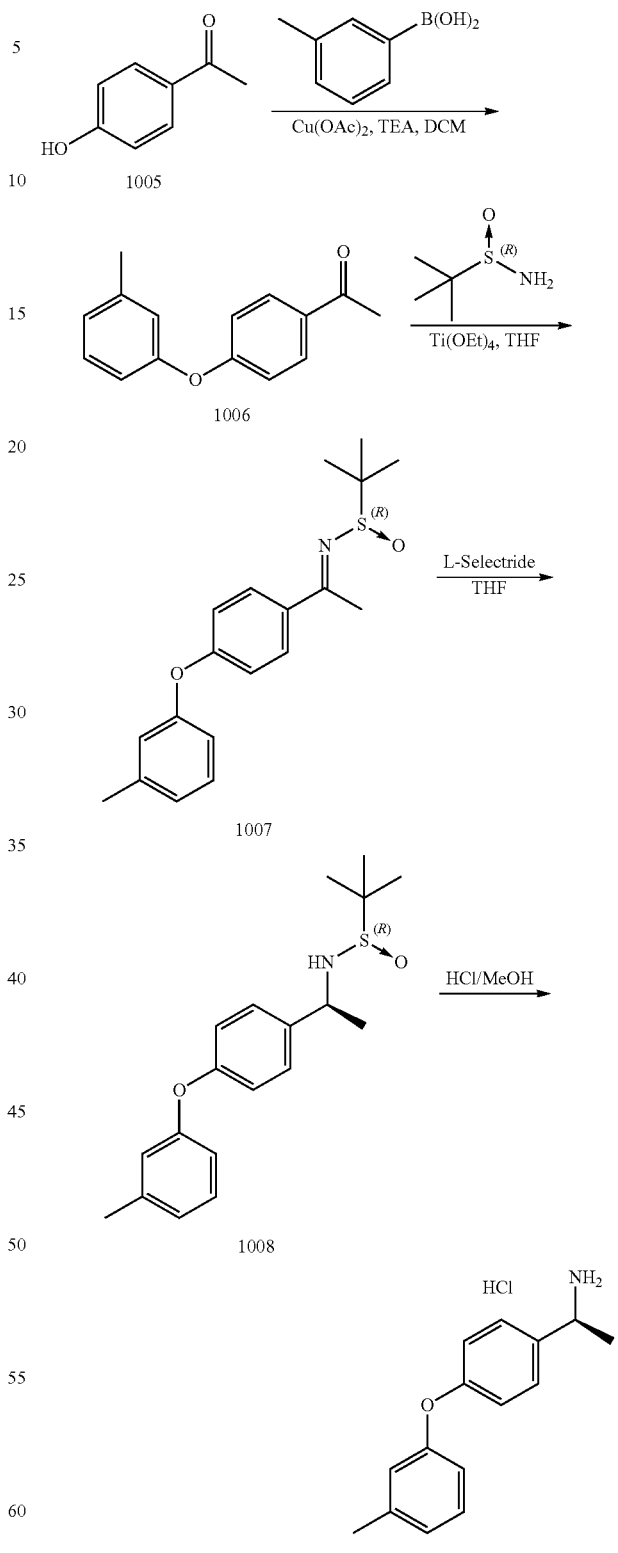

Step 1: Compound 1005 in DCM was reacted with m-tolylboronic acid, Cu(OAc)$_2$ and TEA to give Compound 1006.

Step 2: Compound 1006 in THF was reacted with (R)-(+)-2-methyl-2-propanesulfinamide in the presence of Ti(OEt)$_4$ to give Compound 1007.

Step 3: Compound 1007 in anhydrous THF was reacted with L-selectride to give Compound 1008.

Step 4: Compound 1008 in MeOH was reacted with HCl/MeOH to give Compound 1009.

Scheme 3: Synthesis of the intermediate of formula (Ia)

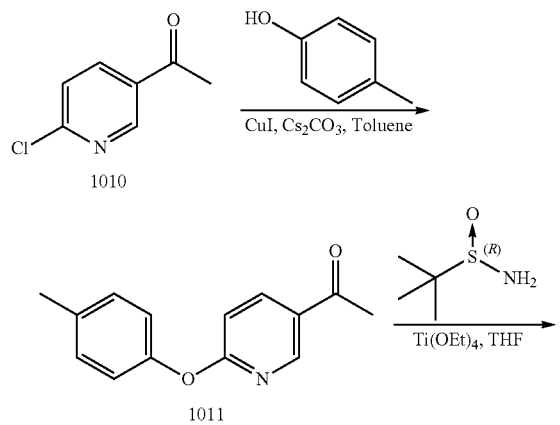

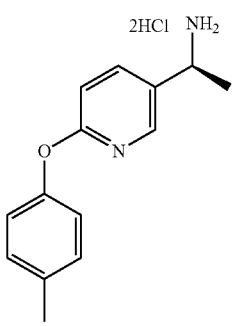

1014

Step 1: Compound 1010 in toluene was reacted with p-cresol, CuI and Cs$_2$CO$_3$ to give Compound 1011.

Step 2: Compound 1011 in THF was reacted with (R)-(+)-2-methyl-2-propanesulfinamide in the presence of Ti(OEt)$_4$ to give Compound 1012.

Step 3: Compound 1012 in anhydrous THF was reacted with L-selectride to give Compound 1013.

Step 4: Compound 1013 in MeOH was reacted with HCl/MeOH to give Compound 1014.

Scheme 4: Synthesis of the intermediate of formula (Ia)

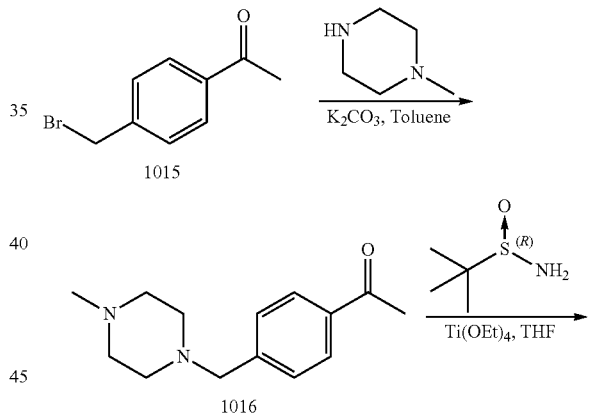

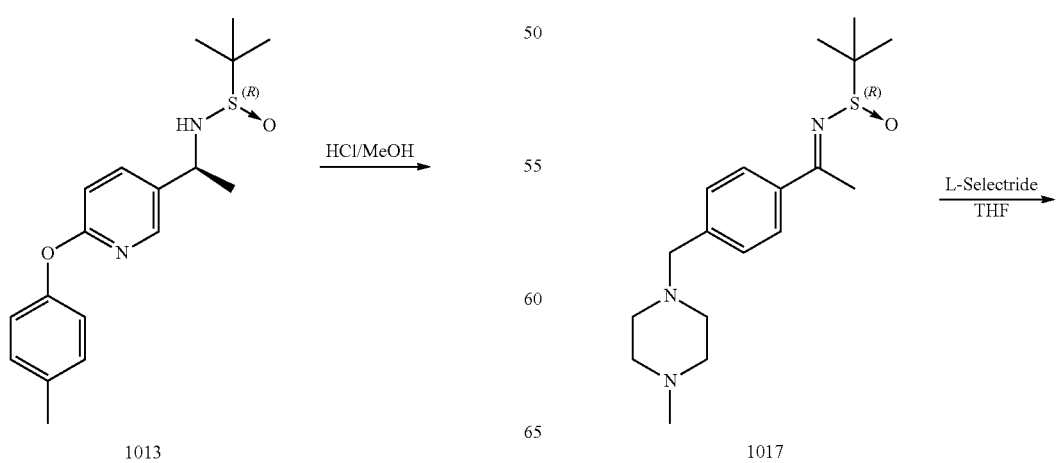

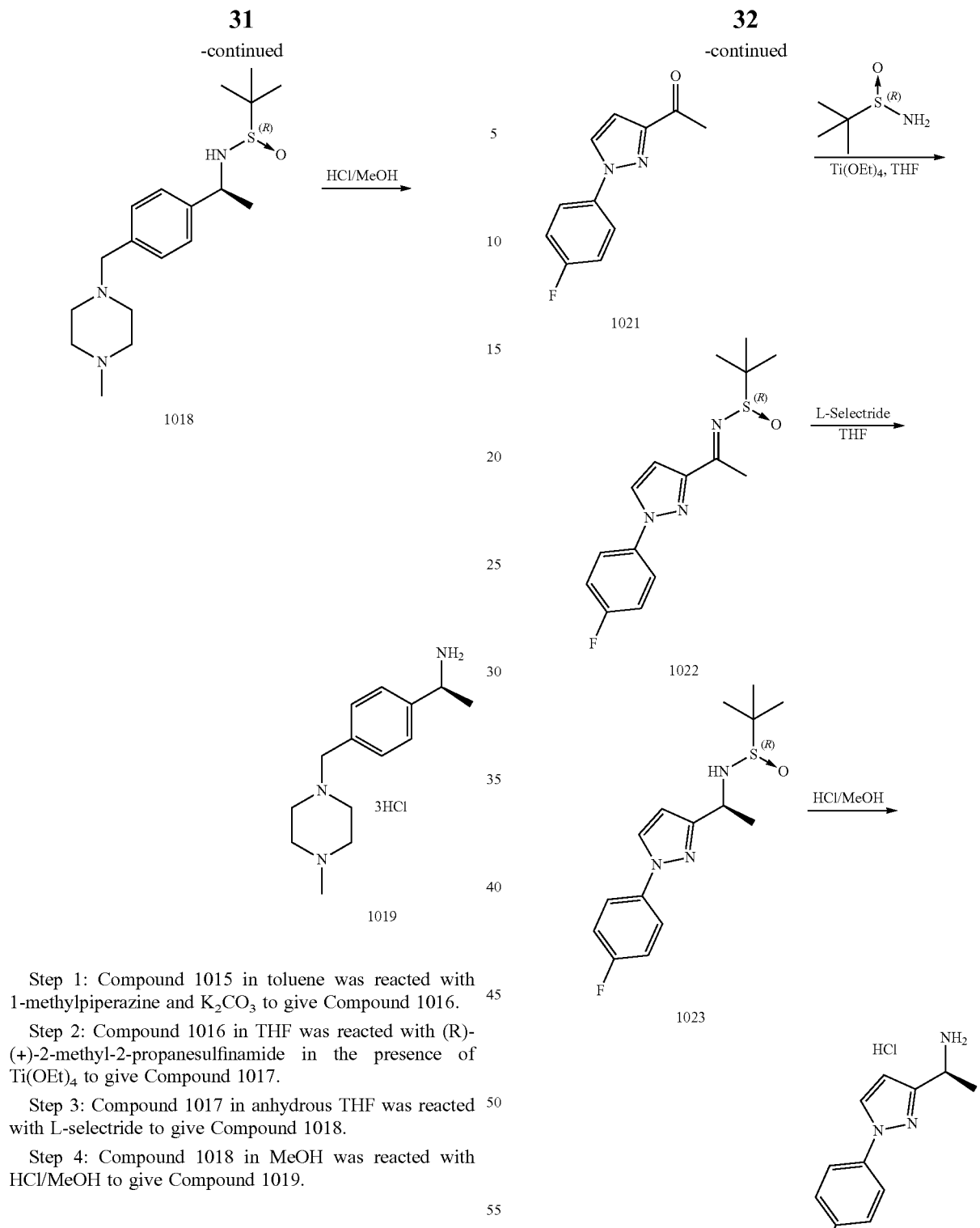

Step 1: Compound 1015 in toluene was reacted with 1-methylpiperazine and K₂CO₃ to give Compound 1016.

Step 2: Compound 1016 in THF was reacted with (R)-(+)-2-methyl-2-propanesulfinamide in the presence of Ti(OEt)₄ to give Compound 1017.

Step 3: Compound 1017 in anhydrous THF was reacted with L-selectride to give Compound 1018.

Step 4: Compound 1018 in MeOH was reacted with HCl/MeOH to give Compound 1019.

Scheme 5: Synthesis of the intermediate of formula (Ia)

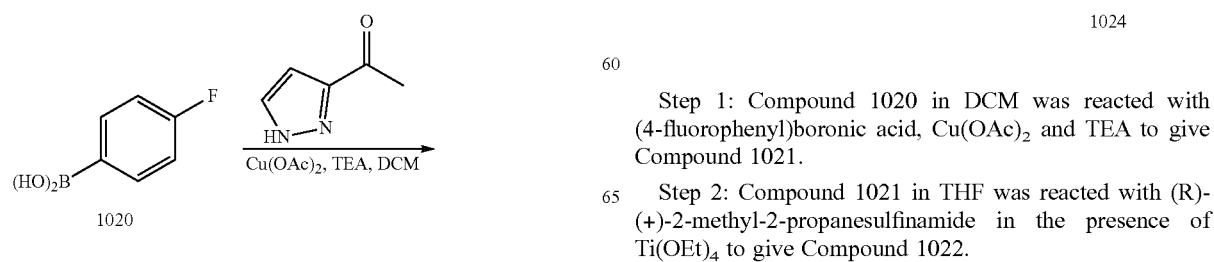

Step 1: Compound 1020 in DCM was reacted with (4-fluorophenyl)boronic acid, Cu(OAc)₂ and TEA to give Compound 1021.

Step 2: Compound 1021 in THF was reacted with (R)-(+)-2-methyl-2-propanesulfinamide in the presence of Ti(OEt)₄ to give Compound 1022.

Step 3: Compound 1022 in anhydrous THF was reacted with L-selectride to give Compound 1023.

Step 4: Compound 1023 in MeOH was reacted with HCl/MeOH to give Compound 1024.

Scheme 6: Synthesis of the compounds of Formula (Ia)

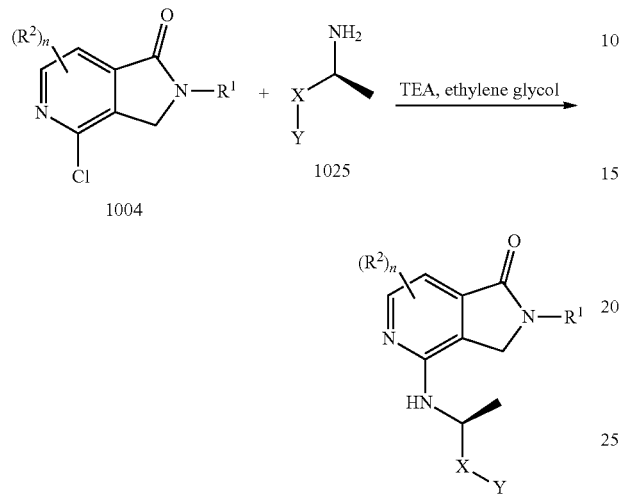

Compound 1004 in ethylene glycol was reacted with Compound 1025 and TEA to give the target compound, wherein the definitions of R¹, R², X and Y are as disclosed above.

Scheme 7: Synthesis of the compounds of Formula (Ia)

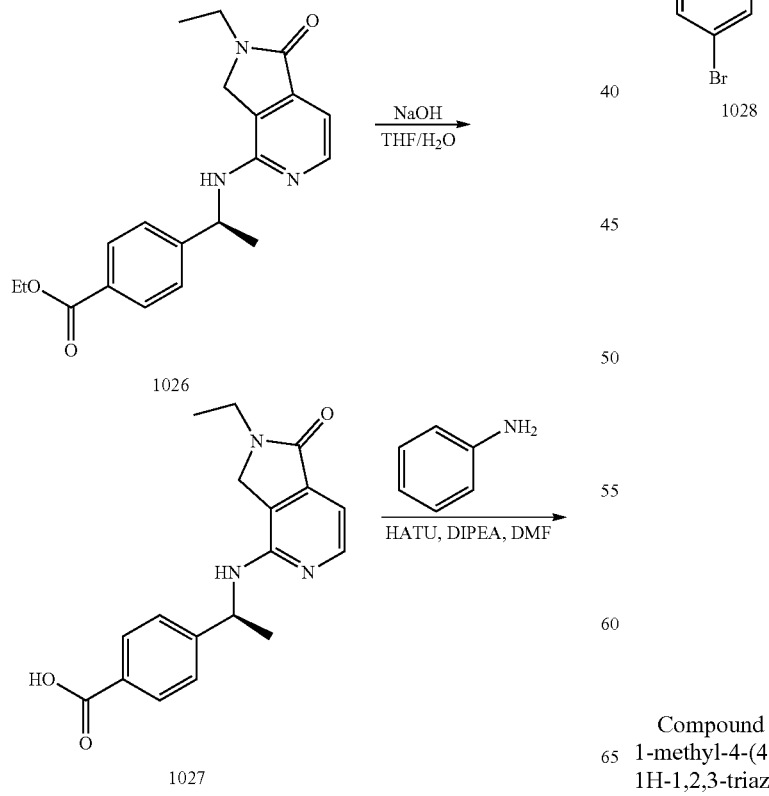

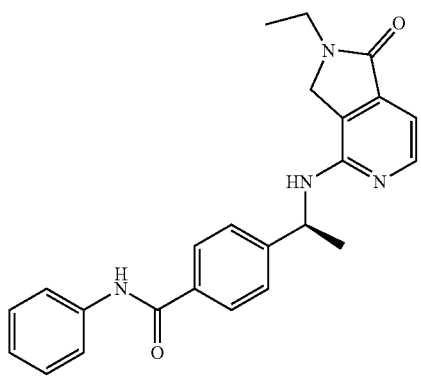

Step 1: Compound 1026 in THF was reacted with NaOH in water to give Compound 1027.

Step 2: Compound 1027 in DMF was reacted with aniline, DIPEA and HATU to give the target compound.

Scheme 8: Synthesis of the compounds of Formula (Ia)

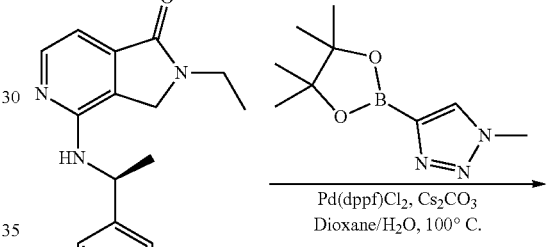

Compound 1028 in dioxane/H$_2$O was reacted with 1-methyl-4-(4,4,5,5-tetramethyl-1,3,2-dioxaborolan-2-yl)-1H-1,2,3-triazole, Cs$_2$CO$_3$ and Pd(dppf)Cl$_2$ in water to give the target compound.

Scheme 9: Synthesis of the compounds of Formula (Ia)

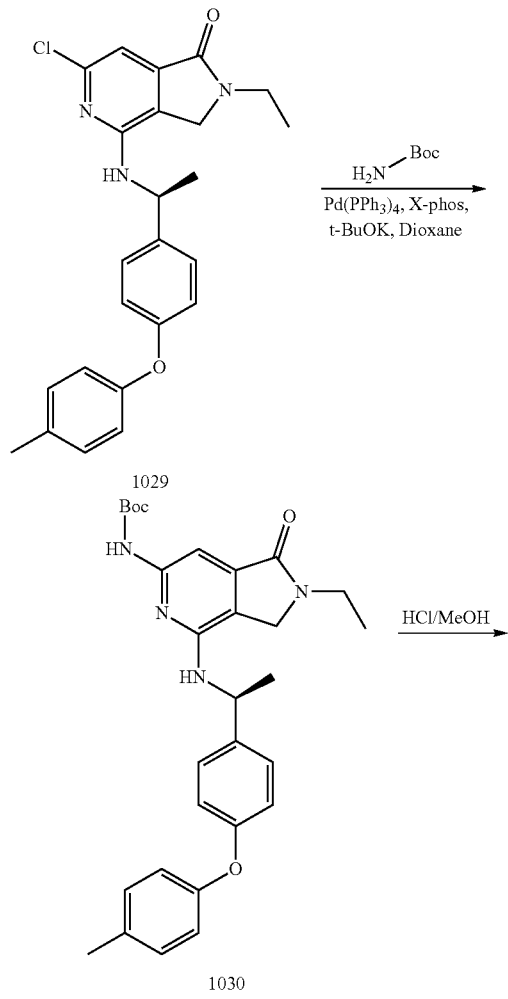

Scheme 10: Synthesis of the compounds of Formula (Ia)

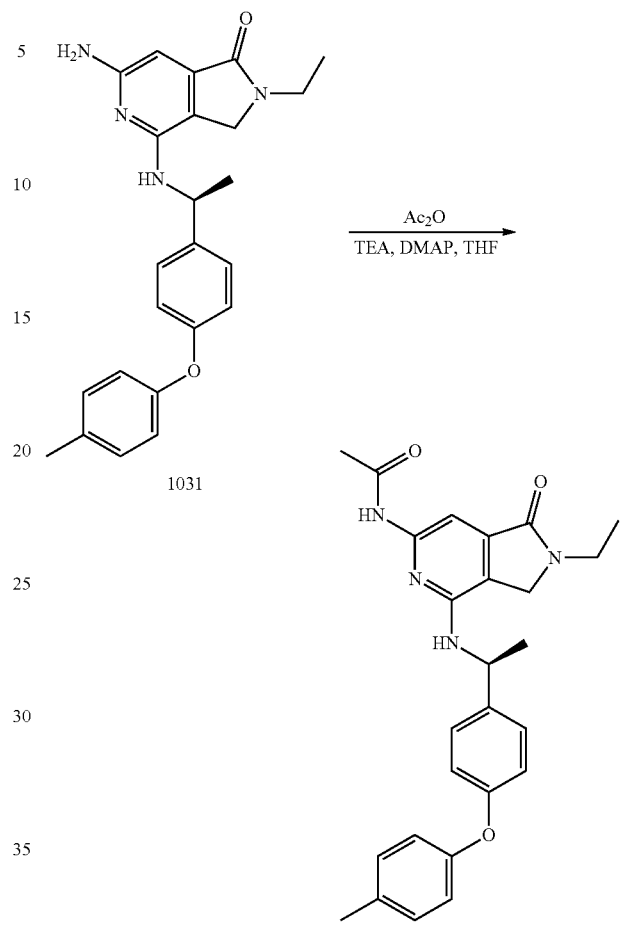

Compound 1031 in THF was reacted with Ac₂O, TEA and DMAP to give the target compound.

Scheme 11: Synthesis of the compounds of Formula (Ia)

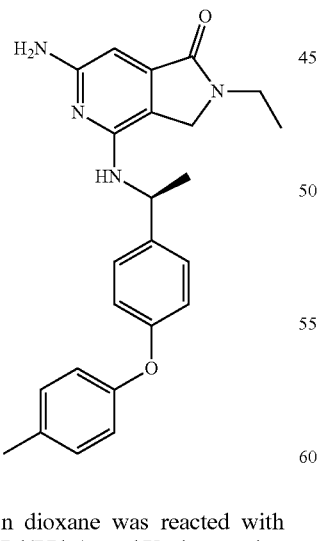

Step 1: Compound 1029 in dioxane was reacted with tert-butyl carbamate, t-BuOK, Pd(PPh₃)₄ and X-phos to give Compound 1030.

Step 2: Compound 1030 in MeOH was reacted with HCl/MeOH to give the target compound -continued

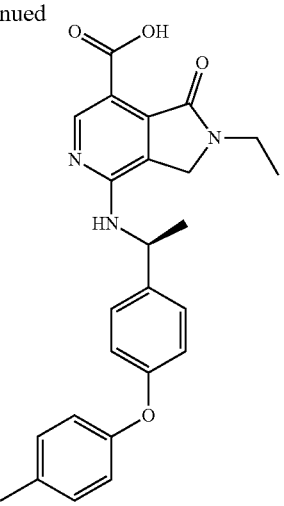

Compound 1032 in THF was reacted with NaOH in water to give the target compound.

Pharmaceutical Composition

The present disclosure provides pharmaceutical compositions comprising at least one compound disclosed herein. In some embodiments, the pharmaceutical composition comprises more than one compounds disclosed herein. In some embodiments, the pharmaceutical composition comprises one or more compounds disclosed herein, and a pharmaceutical acceptable carrier.

The pharmaceutically acceptable carriers are conventional medicinal carriers in the art which can be prepared in a manner well known in the pharmaceutical art. In some embodiments, the compounds disclosed herein may be admixed with pharmaceutically acceptable carrier for the preparation of pharmaceutical composition.

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments, compounds, materials, compositions, and/or dosage forms that are pharmaceutically acceptable refer to those approved by a regulatory agency (such as U.S. Food and Drug Administration, China Food and Drug Administration or European Medicines Agency) or listed in generally recognized pharmacopoeia (such as U.S. Pharmacopoeia, China Pharmacopoeia or European Pharmacopoeia) for use in animals, and more particularly in humans.

The term "pharmaceutically acceptable carrier" as used herein refers to a pharmaceutically-acceptable material, composition or vehicle, such as a liquid or solid filler, diluent, excipient, solvent or encapsulating material, involved in carrying or transporting a compound provided herein from one location, body fluid, tissue, organ (interior or exterior), or portion of the body, to another location, body fluid, tissue, organ, or portion of the body. Pharmaceutically acceptable carriers can be vehicles, diluents, excipients, or other materials that can be used to contact the tissues of an animal without excessive toxicity or adverse effects. Exemplary pharmaceutically acceptable carriers include, sugars, starch, celluloses, malt, tragacanth, gelatin, Ringer's solution, alginic acid, isotonic saline, buffering agents, and the like. Pharmaceutically acceptable carrier that can be employed in present disclosure includes those generally known in the art, such as those disclosed in "Remington Pharmaceutical Sciences" Mack Pub. Co., New Jersey (1991), which is incorporated herein by reference.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The form of pharmaceutical compositions depends on a number of criteria, including, but not limited to, route of administration, extent of disease, or dose to be administered.

The pharmaceutical compositions can be formulated for oral, nasal, rectal, percutaneous, intravenous, or intramuscular administration. In accordance to the desired route of administration, the pharmaceutical compositions can be formulated in the form of tablets, capsule, pill, dragee, powder, granule, sachets, cachets, lozenges, suspensions, emulsions, solutions, syrups, aerosols (as a solid or in a liquid medium), spray, omintment, paste, cream, lotion, gel, patche, inhalant, or suppository.

The pharmaceutical compositions can be formulated so as to provide quick, sustained or delayed release of the active ingredient after administration to the patient by employing procedures known in the art. In some embodiments, the pharmaceutical composition is formulated in a sustained released form. As used herein, the term "sustained released form" refers to release of the active agent from the pharmaceutical composition so that it becomes available for bio-absorption in the subject, primarily in the gastrointestinal tract of the subject, over a prolonged period of time (extended release), or at a certain location (controlled release). In some embodiments, the prolonged period of time can be about 1 hour to 24 hours, 2 hours to 12 hours, 3 hours to 8 hours, 4 hours to 6 hours, 1 to 2 days or more. In certain embodiments, the prolonged period of time is at least about 4 hours, at least about 8 hours, at least about 12 hours, or at least about 24 hours. The pharmaceutical composition can be formulated in the form of tablet. For example, release rate of the active agent can not only be controlled by dissolution of the active agent in gastrointestinal fluid and subsequent diffusion out of the tablet or pills independent of pH, but can also be influenced by physical processes of disintegration and erosion of the tablet. In some embodiments, polymeric materials as disclosed in "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Ranger and Peppas, 1983, J Macromol. Sci. Rev. Macromol Chem. 23:61; see also Levy et al., 1985, Science 228:190; During et al., 1989, Ann. Neurol. 25:351; Howard et al., 1989, J. Neurosurg. 71:105 can be used for sustained release. The above references are incorporated herein by reference in its entirety.

In certain embodiments, the pharmaceutical compositions comprise about 0.01 mg to about 1000 mg of the compounds provided herein (e.g. about 0.01 mg to about 10 mg, about 0.1 mg to about 10 mg, about 1 mg to about 10 mg, about 5 mg to about 10 mg, about 5 mg to about 20 mg, about 5 mg to about 30 mg, about 5 mg to about 40 mg, about 5 mg to about 50 mg, about 10 mg to about 100 mg, about 20 mg to about 100 mg, about 30 mg to about 100 mg, about 40 mg to about 100 mg, about 50 mg to about 100 mg, about 50 mg to about 200 mg, about 50 mg to about 300 mg, about 50 mg to about 400 mg, about 50 mg to about 500 mg, about 100 mg to about 200 mg, about 100 mg to about 300 mg, about 100 mg to about 400 mg, about 100 mg to about 500 mg, about 200 mg to about 500 mg, about 300 mg to about 500 mg, about 400 mg to about 500 mg, about 500 mg to about 1000 mg, about 600 mg to about 1000 mg, about 700 mg to about 1000 mg, about 800 mg to about 1000 mg, or about 900 mg to about 1000 mg). Suitable dosages per subject per day can be from about 5 mg to about 500 mg, preferably about 5 mg to about 50 mg, about 50 mg to about 100 mg, or about 50 mg to about 500 mg.

In certain embodiments, the pharmaceutical compositions can be formulated in a unit dosage form, each dosage containing from about 0.01 mg to about 10 mg, about 0.1 mg to about 10 mg, about 1 mg to about 10 mg, about 5 mg to about 10 mg, about 5 mg to about 20 mg, about 5 mg to about 30 mg, about 5 mg to about 40 mg, about 5 mg to about 50 mg, about 10 mg to about 100 mg, about 20 mg to about 100 mg, about 30 mg to about 100 mg, about 40 mg to about 100 mg, about 50 mg to about 100 mg, about 50 mg to about 200 mg, about 50 mg to about 300 mg, about 50 mg to about 400 mg, about 50 mg to about 500 mg, about 100 mg to about 200 mg, about 100 mg to about 300 mg, about 100 mg to about 400 mg, about 100 mg to about 500 mg, about 200 mg to about 500 mg, about 300 mg to about 500 mg, about 400 mg to about 500 mg, about 500 mg to about 1000 mg, about 600 mg to about 1000 mg, about 700 mg to about 1000 mg, about 800 mg to about 1000 mg, or about 900 mg to about 1000 mg of the compounds disclosed herein. The term "unit dosage forms" refers to physically discrete units suitable as unitary dosages for human subjects and other mammals, each unit containing a predetermined quantity of active material calculated to produce the desired therapeutic effect, in association with a suitable pharmaceutical carrier.

In some embodiments, the pharmaceutical compositions comprising one or more compounds disclosed herein as a first active ingredient, and further comprises a second active ingredient. The second active ingredient can be any anticancer agent known in the art. Representative examples of the anticancer agent for treating cancers or tumors may include, but are not limited to, cell signal transduction inhibitors (e.g., imatinib, gefitinib, bortezomib, erlotinib, sorafenib, sunitinib, dasatinib, vorinostat, lapatinib, temsirolimus, nilotinib, everolimus, pazopanib, trastuzumab, bevacizumab, cetuximab, ranibizumab, pegaptanib, panitumumab and the like), mitosis inhibitors (e.g., paclitaxel, vincristine, vinblastine and the like), alkylating agents (e.g., cisplatin, cyclophosphamide, chromabucil, carmustine and the like), anti-metabolites (e.g., methotrexate, 5-FU and the like), intercalating anticancer agents, (e.g., actinomycin, anthracycline, bleomycin, mitomycin-C and the like), topoisomerase inhibitors (e.g., irinotecan, topotecan, teniposide and the like), immunotherapic agents (e.g., interleukin, interferon and the like) and antihormonal agents (e.g., tamoxifen, raloxifene and the like). In some embodiments, the second active agent is one or more of Ibrutinib, Venetoclax, Imatinib Mesylate, Nilotinib Hydrochloride, Bosutinib, Dasatinib, Etoposide, Fludarabine Phosphate, Ponatinib, Vincristine Sulfate, Methotrexate, Cyclophosphamide, Lomustine, Teniposide, Temozolomide, Fotemustine, Carmustine, Bevacizumab, Picibanil, Fluorouracil, Melphalan, Emcitabine Hydrochloride.

Method for Treatment

The present disclosure provides a method of treating a disease associated with IDH, comprising administering to a subject an effective amount of one or more compounds, pharmaceutically acceptable salts, hydrates, solvates or stereoisomers thereof or the pharmaceutical composition disclosed herein.

In some embodiments, the one or more compounds pharmaceutically acceptable salts, hydrates, solvates or stereoisomers thereof or the pharmaceutical composition provided herein is administered via a parenteral route or a non-parenteral route. In some embodiments, the one or more compounds pharmaceutically acceptable salts, hydrates, solvates or stereoisomers thereof or the pharmaceutical composition is administered orally, enterally, buccally, nasally, intranasally, transmucosally, epidermally, transdermally, dermally, ophthalmically, pulmonary, sublingually, rectally, vaginally, topically, subcutaneously, intravenously, intramuscularly, intraarterially, intrathecally, intracapsularly, intraorbitally, intracardiacally, intradermally, intraperitoneally, transtracheally, subcuticularly, intra-articularly, subcapsularly, subarachnoidly, intraspinally, or intrasternally.

The compounds provided herein can be administered in pure form, in a combination with other active ingredients or in the form of pharmaceutically composition of the present disclosure. In some embodiments, the compounds provided herein can be administered to a subject in need concurrently or sequentially in a combination with one or more anticancer agent(s) known in the art. In some embodiments, the administration is conducted once a day, twice a day, three times a day, or once every two days, once every three days, once every four days, once every five days, once every six days, once a week.

In certain embodiments, the present disclosure provides use of the compounds, pharmaceutically acceptable salts, hydrates, solvates or stereoisomers thereof, or pharmaceutical composition of the present disclosure in the manufacture of medicaments for treating diseases associated with the conversion of α-KG to D-2-HG In certain embodiments, the present disclosure provides use of the compounds, pharmaceutically acceptable salts, hydrates, solvates or stereoisomers thereof, or pharmaceutical composition of the present disclosure in the manufacture of medicaments for treating diseases associated with the mutant IDH.

In certain embodiments, the diseases associated with the conversion of α-KG to D-2-HG are diseases associated with mutant IDH, including cancers.

In particular, the cancers include but are not limited to, leukemia, glioblastoma, melanoma, chondrosarcoma, cholangiocarcinoma, osteosarcoma, lymphoma, lung cancer, adenoma, myeloma, hepatocellular carcinoma, adrenocortical carcinoma, pancreatic cancer, breast cancer, prostate cancer, liver cancer, gastric cancer, colon cancer, colorectal cancer, ovarian cancer, cervical cancer, brain cancer, esophageal cancer, bone cancer, testicular cancer, skin cancer, kidney cancers, mesothelioma, neuroblastoma, thyroid cancer, head and neck cancers, esophageal cancers, eye cancers, prostate cancer, nasopharyngeal cancer, or oral cancer. In some embodiments, the cancers are leukemia, glioblastoma, or cholangiocarcinoma.

The compounds and pharmaceutical compositions thereof in the present disclosure can be used in the prevention or treatment of the onset or development of any of the diseases or conditions associated with the conversion of α-KG to D-2-HG in mammals especially in human. In some embodiments, the compounds and pharmaceutical compositions thereof in the present disclosure can be used in the prevention or treatment of the onset or development of any of the diseases or conditions associated with mutant IDH in mammals especially in human.

In such situation, the present disclosure also provides a method of screening patient suitable for treating with the compounds or pharmaceutical composition of the present disclosure alone or combined with other ingredients (e.g. an second active ingredient, e.g. anticancer agent). The method includes sequencing the tumor samples from patients and detecting the accumulation of D-2-HG in the patient or detecting the mutations status of IDH in the patient.

EXAMPLES

The followings further explain the general methods of the present disclosure. The compounds of the present disclosure may be prepared by the methods known in the art. The following illustrate the detailed preparation methods of the preferred compounds of the present disclosure. However, they are by no means limiting the preparation methods of the compounds of the present disclosure.

Synthetic Examples

The structures of the compounds in the following examples were characterized by nuclear magnetic resonance (NMR) or/and mass spectrometry (ESI). NMR shift (δ) was given in the unit of $10^{-6}$ (ppm). $^1$H-NMR spectra was recorded in dimethyl sulfoxide-$d_6$ (DMSO-$d_6$) or CDCl$_3$ on a Varian Mercury VX 400 spectrometer with tetramethylsilane (TMS) as an internal standard.

ESI-HRMS measurement was carried out using Agilent 1260-6230 TOF LC-MS mass spectrometer.

High Performance Liquid Chromatography (HPLC) measurement was carried out on Agilent 1200 LC using the Phenomen C18 column (4.6 mm*150 mm, 0.4 μm).

Thin layer chromatography was carried out using Yantai Huanghai HSGF254 silica gel plates. The silica gel plates used for thin layer chromatography (TLC) were 0.15 mm-0.2 mm. The silica gel plates used for separating and purifying products by TLC were 0.4 mm-0.5 mm.

Purified chromatographic column uses the silica gel as the carrier (200-300 mesh, producted by Yantai Huanghai co.).

The known starting materials of the present disclosure can be synthesized by using or according to the known methods in the art, or can be purchased from Alfa Aesar, Langcaster, TCI, Aldrich, Bepharm, and Scochem.

Unless otherwise specified, the reactions in the examples were all carried out under argon or nitrogen atmosphere. Argon or nitrogen atmosphere refers to that the reaction flask is connected to an argon or nitrogen ballon with a volume of about 1 L. Hydrogenation was usually carried out under vacuum, filled with hydrogen, and repeated for three times.

Unless otherwise specified, the reaction temperature in the examples was ambient temperature, which was 20° C.-30° C.

The reaction progress in the examples was monitored by TLC. The eluent systems used for the reactions include dichloromethane-methanol system and petroleum ether-ethyl acetate system. The volume ratios of the solvents were adjusted according to the different polarities of compounds.

The elution system of column chromatography used for purifying compounds and eluent system of TLC include dichloromethane-methanol system and petroleum ether-ethyl acetate system. The volume ratios of the solvents were adjusted according to the different polarities of compounds. A small amount of alkaline or acidic agents such as triethylamine and acetic acid can be added for adjustment.

Synthetic Example 1

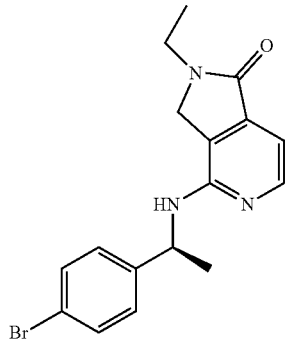 [SMILES: CCN1Cc2c(ccnc2N[C@@H](C)c2ccc(Br)cc2)C1=O]

(S)-4-(1-(4-bromophenyl)ethylamino)-2-ethyl-2,3-dihydro-1H-pyrrolo[3,4-c]pyridin-1-one Compound 1 of the present disclosure was prepared according to Schemes 1 and 6.

Step 1

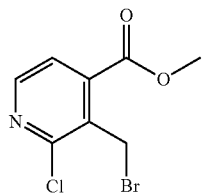

Methyl 3-(bromomethyl)-2-chloroisonicotinate

To a solution of methyl 2-chloro-3-methylisonicotinate (6.00 g, 32.32 mmol) in CCl$_4$ (30 mL) was added NBS (6.06 g, 33.94 mmol) and BPO (780 mg, 3.23 mmol). After addition, the reaction mixture was heated to reflux for 3 h. TLC indicated that starting material was consumed. Then, it was cooled to ambient temperature and the resulting precipitate was removed by filtration, washed by CCl$_4$ (5 mL). The filtrate was concentrated in vacuo to give the crude product methyl 3-(bromomethyl)-2-chloroisonicotinate as a yellow oil, which was used in next step without further purification.

Step 2

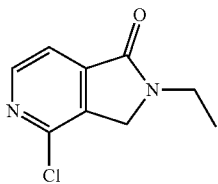

4-chloro-2-ethyl-2,3-dihydro-1H-pyrrolo[3,4-c]pyridin-1-one

The above crude product was dissolved in THF (50 mL). Ethanamine hydrochloride (2.64 g, 32.32 mmol) and $Cs_2CO_3$ (42.12 g, 129.28 mmol) were added into the reaction mixture. It was stirred at ambient temperature for 12 h. TLC indicated that starting material was consumed. The solid was removed by filtration, washed by ethyl acetate (10 mL) and the filtrate was concentrated in vacuo. The crude product was purified by silica gel column chromatography (eluted by Petroleum ether:Ethyl acetate=2:1) to give desired product as light yellow solid (2.31 g, yield 36.2% in two steps). $^1$H NMR (400 MHz, $CDCl_3$) δ 8.51 (d, J=4.8 Hz, 1H), 7.64 (d, J=4.8 Hz, 1H), 4.40 (s, 2H), 3.67 (q, J=7.2 Hz, 2H), 1.28 (t, J=7.2 Hz, 3H).

Step 3

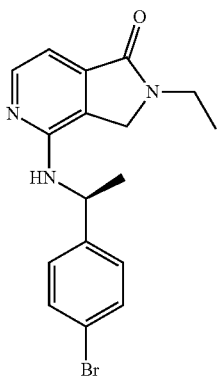 [SMILES: CCN1Cc2c(ccnc2N[C@@H](C)c2ccc(Br)cc2)C1=O]

(S)-4-((1-(4-bromophenyl)ethyl)amino)-2-ethyl-2,3-dihydro-1H-pyrrolo[3,4-c]pyridin-1-one To a solution of 4-chloro-2-ethyl-2,3-dihydro-1H-pyrrolo[3,4-c]pyridin-1-one (150 mg, 0.76 mmol) in ethylene glycol (15 mL) was added (S)-1-(4-bromophenyl)ethanamine (229 mg, 1.14 mmol) and TEA (232 mg, 2.29 mmol). The reaction mixture was heated to 150 C and stirred for 5 h. It was cooled to ambient temperature and diluted with 30 mL water, extracted with ethyl acetate (25 mL×2). The combined organic layers were dried over sodium sulfate, filtered and concentrated. The crude product was purified by preparative TLC (DCM:MeOH=20:1) to give desired product as a white solid (80 mg, yield 29.1%).
$^1$H NMR (400 MHz, $CDCl_3$) δ 8.13 (d, J=5.1 Hz, 1H), 7.30 (d, J=7.5 Hz, 2H), 7.04 (d, J=7.5 Hz, 2H), 6.84 (d, J=5.1 Hz, 1H), 5.24 (br, 1H), 4.72-4.52 (m, 1H), 4.21 (s, 2H), 3.40 (q, J=7.1 Hz, 2H), 2.05 (s, 3H), 1.54 (d, J=6.6 Hz, 3H), 1.14 (t, J=7.1 Hz, 3H). ESI-MS m/z 360.1 [M+H].

Synthetic Example 2

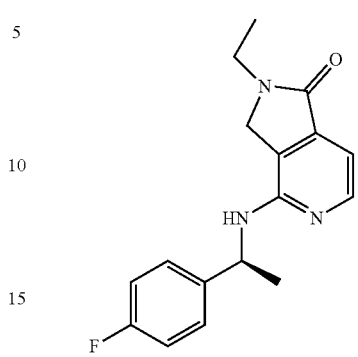

(S)-2-ethyl-4-(1-(4-fluorophenyl)ethylamino)-2,3-dihydro-1H-pyrrolo[3,4-c]pyridin-1-one Compound 1 of the present disclosure was prepared according to Schemes 1 and 6. The synthetic method was similar with Synthetic Example 1, except that the (S)-1-(4-bromophenyl)ethanamine was replaced by (S)-1-(4-fluorophenyl)ethanamine.
$^1$H NMR (400 MHz, $CDCl_3$) δ 8.14 (d, J=5.4 Hz, 1H), 7.42-7.31 (m, 2H), 7.27-7.09 (m, 2H), 6.99 (d, J=5.4 Hz, 1H), 5.28 (br, 1H), 4.61-4.41 (m, 1H), 4.15 (s, 2H), 3.51 (q, J=7.2 Hz, 2H), 2.35 (s, 3H), 1.58 (d, J=6.7 Hz, 3H), 1.12 (t, J=7.2 Hz, 3H). ESI-MS m/z 300.1 [M+H].

Synthetic Example 3

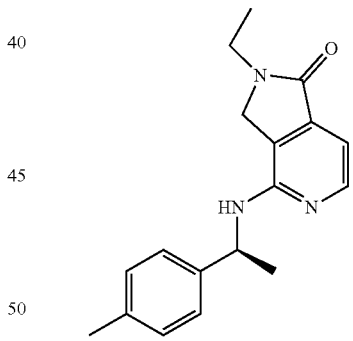

(S)-2-ethyl-4-(1-p-tolylethylamino)-2,3-dihydro-1H-pyrrolo[3,4-c]pyridin-1-one

Compound 3 of the present disclosure was prepared according to Schemes 1 and 6. The synthetic method was similar with Synthetic Example 1, except that the (S)-1-(4-bromophenyl)ethanamine was replaced by (S)-1-(4-methylphenyl)ethanamine.
$^1$H NMR (400 MHz, $CDCl_3$) δ 8.14 (d, J=5.2 Hz, 1H), 7.22 (d, J=7.8 Hz, 2H), 7.07 (d, J=7.8 Hz, 2H), 6.94 (d, J=5.2 Hz, 1H), 5.27 (br, 1H), 4.69-4.42 (m, 1H), 4.12 (s, 2H), 3.56 (q, J=7.4 Hz, 2H), 2.25 (s, 3H), 1.52 (d, J=6.7 Hz, 3H), 1.16 (t, J=7.4 Hz, 3H). ESI-MS m/z 296.2 [M+H].

Synthetic Example 4

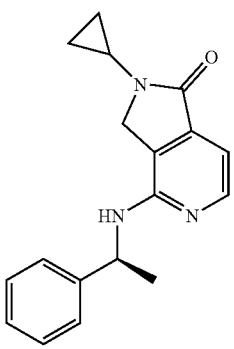 [SMILES: C[C@H](Nc1nccc2c1CN(C1CC1)C2=O)c1ccccc1]

(S)-2-cyclopropyl-4-(1-phenylethylamino)-2,3-di-hydro-1H-pyrrolo[3,4-c]pyridin-1-one Compound 4 of the present disclosure was prepared according to Schemes 1 and 6. The synthetic method was similar with Synthetic Example 1, except that ethanamine hydrochloride was replaced by cyclopropanamine hydrochloride, and the (S)-1-(4-bromophenyl)ethanamine was replaced by (S)-1-phenylethanamine.

$^1$H NMR (400 MHz, CDCl$_3$) δ 8.12 (d, J=5.2 Hz, 1H), 7.31 (d, J=7.5 Hz, 2H), 7.24 (t, J=7.5 Hz, 2H), 7.20-7.13 (m, 1H), 6.91 (d, J=5.1 Hz, 1H), 5.30 (p, J=7.0 Hz, 1H), 4.54 (d, J=7.5 Hz, 1H), 4.07 (s, 2H), 2.81 (h, J=4.7, 3.6 Hz, 1H), 1.52 (d, J=6.7 Hz, 3H), 0.88-0.69 (m, 4H). ESI-MS m/z 294.2 [M+H].

Synthetic Example 5

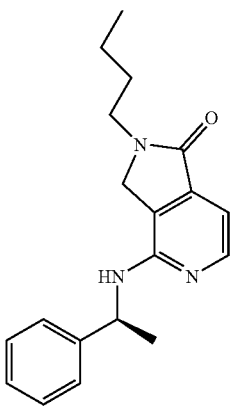 [SMILES: CCCCN1Cc2c(ccnc2N[C@@H](C)c2ccccc2)C1=O]

(S)-2-butyl-4-(1-phenylethylamino)-2,3-dihydro-1H-pyrrolo[3,4-c]pyridin-1-one

Compound 5 of the present disclosure was prepared according to Schemes 1 and 6. The synthetic method was similar with Synthetic Example 1, except that ethanamine hydrochloride was replaced by n-butylamine hydrochloride, and the (S)-1-(4-bromophenyl)ethanamine was replaced by (S)-1-phenylethanamine.

$^1$H NMR (400 MHz, CDCl$_3$) δ 8.14 (d, J=5.2 Hz, 1H), 7.37 (d, J=7.6 Hz, 2H), 7.22 (t, J=7.5 Hz, 2H), 7.12 (d, J=7.0 Hz, 1H), 6.95 (d, J=5.2 Hz, 1H), 5.41-5.22 (m, 1H), 4.07 (s, 2H), 3.62 (t, J=7.4 Hz, 2H), 1.61-1.68 (m, 2H), 1.35-1.42 (m, 2H), 0.95 (t, J=7.4 Hz, 3H). ESI-MS m/z 310.2 [M+H].

Synthetic Example 6

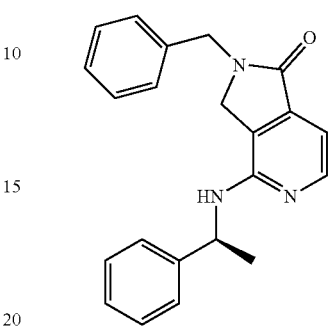

(S)-2-benzyl-4-(1-phenyl ethylamino)-2,3-dihydro-1H-pyrrolo[3,4-c]pyridin-1-one

Compound 6 of the present disclosure was prepared according to Schemes 1 and 6. The synthetic method was similar with Synthetic Example 1, except that ethanamine hydrochloride was replaced by benzyl amine, and the (S)-1-(4-bromophenyl)ethanamine was replaced by (S)-1-phenylethanamine.

$^1$H NMR (400 MHz, CDCl$_3$) δ 8.14 (d, J=5.2 Hz, 1H), 7.37-7.11 (m, 10H), 7.09-6.94 (m, 1H), 5.23 (q, J=7.1 Hz, 1H), 4.69 (d, J=2.7 Hz, 2H), 4.09 (s, 2H), 1.53 (s, 3H). ESI-MS m/z 344.2 [M+H].

Synthetic Example 7

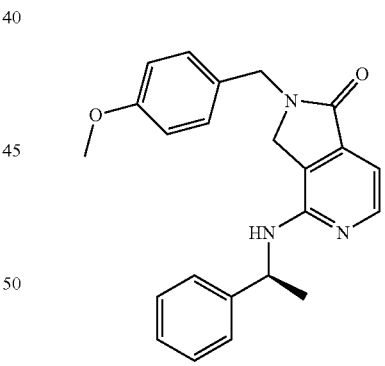

(S)-2-(4-methoxybenzyl)-4-(1-phenylethylamino)-2,3-dihydro-1H-pyrrolo[3,4-c]pyridin-1-one Compound 7 of the present disclosure was prepared according to Schemes 1 and 6. The synthetic method was similar with Synthetic Example 1, except that ethanamine hydrochloride was replaced by 4-methoxybenzyl amine, and the (S)-1-(4-bromophenyl)ethanamine was replaced by (S)-1-phenylethanamine.

$^1$H NMR (400 MHz, CDCl$_3$) δ 8.14 (d, J=5.1 Hz, 1H), 7.31-7.15 (m, 5H), 7.14-7.08 (m, 2H), 7.01-6.95 (m, 1H), 6.82-6.74 (m, 2H), 5.26 (p, J=6.9 Hz, 1H), 4.61 (d, J=2.5 Hz,

2H), 4.17 (s, 2H), 3.95 (s, 2H), 3.71 (d, J=1.9 Hz, 3H), 1.49 (d, J=6.6 Hz, 3H). ESI-MS m/z 374.2 [M+H].

Synthetic Example 8

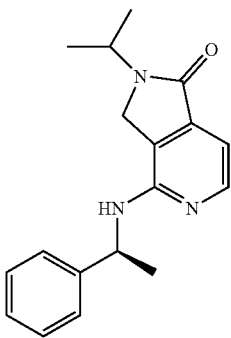 [SMILES: CC(C)N1Cc2c(ccnc2N[C@@H](C)c2ccccc2)C1=O]

(S)-2-isopropyl-4-(1-phenylethylamino)-2,3-dihydro-1H-pyrrolo[3,4-c]pyridin-1-one Compound 8 of the present disclosure was prepared according to Schemes 1 and 6. The synthetic method was similar with Synthetic Example 1, except that ethanamine hydrochloride was replaced by isopropylamine, and the (S)-1-(4-bromophenyl)ethanamine was replaced by (S)-1-phenylethanamine.

$^1$H NMR (400 MHz, CDCl$_3$) δ 8.13 (d, J=5.7 Hz, 1H), 7.34 (d, J=7.6 Hz, 2H), 7.26 (t, J=7.5 Hz, 2H), 7.18 (d, J=7.0 Hz, 1H), 6.94 (d, J=5.1 Hz, 1H), 5.32 (p, J=7.2 Hz, 1H), 4.68-4.49 (m, 2H), 4.07 (s, 2H), 1.54 (d, J=6.8 Hz, 3H), 1.18 (d, J=6.7 Hz, 6H). ESI-MS m/z 296.2 [M+H].

Synthetic Example 9

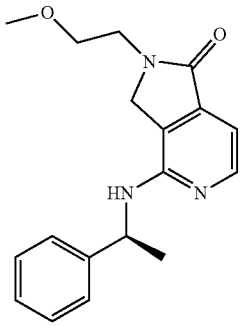 [SMILES: COCCN1Cc2c(ccnc2N[C@@H](C)c2ccccc2)C1=O]

(S)-2-(2-methoxyethyl)-4-(1-phenylethylamino)-2,3-dihydro-1H-pyrrolo[3,4-c]pyridin-1-one Compound 9 of the present disclosure was prepared according to Schemes 1 and 6. The synthetic method was similar with Synthetic Example 1, except that ethanamine hydrochloride was replaced by 2-methoxyethylamine, and the (S)-1-(4-bromophenyl)ethanamine was replaced by (S)-1-phenylethanamine.

$^1$H NMR (400 MHz, CDCl$_3$) δ 8.15 (d, J=5.2 Hz, 1H), 7.33 (d, J=7.7 Hz, 2H), 7.26 (d, J=6.8 Hz, 2H), 7.23-7.13 (m, 1H), 6.96 (d, J=5.2 Hz, 1H), 5.32 (p, J=7.1 Hz, 1H), 4.38 (d, J=7.4 Hz, 1H), 4.27 (s, 2H), 3.70 (t, J=5.1 Hz, 2H), 3.53 (t, J=5.0 Hz, 2H), 3.27 (s, 3H), 1.54 (d, J=6.7 Hz, 3H). ESI-MS m/z 312.2 [M+H].

Synthetic Example 10

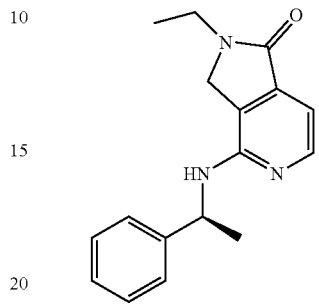

(S)-2-ethyl-4-(1-phenylethylamino)-2,3-dihydro-1H-pyrrolo[3,4-c]pyridin-1-one

Compound 10 of the present disclosure was prepared according to Schemes 1 and 6. The synthetic method was similar with Synthetic Example 1, except that the (S)-1-(4-bromophenyl)ethanamine was replaced by (S)-1-phenylethanamine.

$^1$H NMR (400 MHz, CDCl$_3$) δ 8.15 (d, J=5.1 Hz, 1H), 7.32 (t, J=8.8 Hz, 2H), 7.30 (s, 2H), 7.19 (t, J=6.9 Hz, 2H), 6.96 (d, J=5.1 Hz, 1H), 5.32 (p, J=6.6 Hz, 1H), 4.46 (s, 1H), 4.13 (d, J=3.0 Hz, 2H), 3.57 (q, J=7.1 Hz, 2H), 1.54 (d, J=6.7 Hz, 3H), 1.17 (t, J=7.1 Hz, 3H). ESI-MS m/z 282.2 [M+H].

Synthetic Example 11

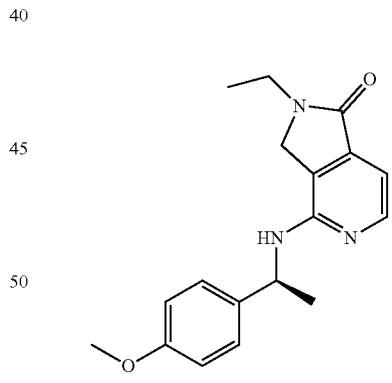

(S)-2-ethyl-4-(1-(4-methoxyphenyl)ethylamino)-2,3-dihydro-1H-pyrrolo[3,4-c]pyridin-1-one Compound 11 of the present disclosure was prepared according to Schemes 1 and 6. The synthetic method was similar with Synthetic Example 1, except that the (S)-1-(4-bromophenyl)ethanamine was replaced by (S)-1-(4-methoxyphenyl)ethanamine.

$^1$H NMR (400 MHz, CDCl$_3$) δ 8.22 (d, J=5.1 Hz, 1H), 7.32 (d, J=8.6 Hz, 2H), 7.02 (d, J=5.2 Hz, 1H), 6.87 (d, J=8.6 Hz, 2H), 5.33 (p, J=6.9 Hz, 1H), 4.49 (s, 1H), 4.18 (s, 2H), 3.79 (s, 3H), 3.64 (q, J=7.3 Hz, 2H), 1.59 (d, J=6.8 Hz, 3H), 1.29-1.23 (m, 3H). ESI-MS m/z 312.2 [M+H].

Synthetic Example 12

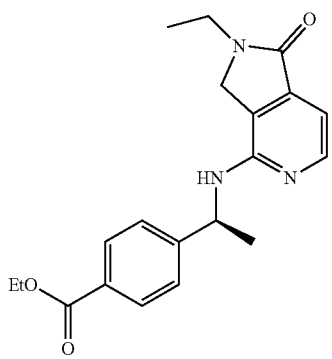 [SMILES: CCOC(=O)c1ccc([C@H](C)Nc2nccc3c2CN(CC)C3=O)cc1]

(S)-ethyl-4-(1-(2-ethyl-1-oxo-2,3-dihydro-1H-pyrrolo[3,4-c]pyridin-4-ylamino)ethyl)benzoate Compound 12 of the present disclosure was prepared according to Schemes 1 and 6. The synthetic method was similar with Synthetic Example 1, except that the (S)-1-(4-bromophenyl)ethanamine was replaced by (S)-ethyl-4-((1-amino)ethyl)benzoate.

¹H NMR (400 MHz, CDCl₃) δ 8.16 (d, J=5.1 Hz, 1H), 8.00 (dd, J=16.5, 8.2 Hz, 2H), 7.43 (t, J=9.1 Hz, 2H), 7.01 (d, J=5.1 Hz, 1H), 5.41 (p, J=6.6 Hz, 1H), 4.70 (d, J=5.7 Hz, 1H), 4.34 (q, J=7.1 Hz, 2H), 4.24 (d, J=5.2 Hz, 2H), 3.63 (q, J=7.2 Hz, 2H), 1.58 (t, J=7.6 Hz, 3H), 1.36 (t, J=7.1 Hz, 3H), 1.24 (t, J=7.2 Hz, 3H). ESI-MS m/z 354.2 [M+H].

Synthetic Example 13

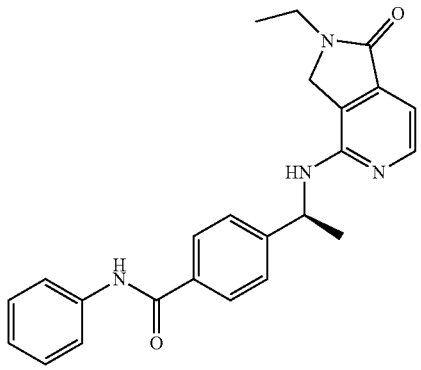 [SMILES: CCN1Cc2c(ccnc2N[C@@H](C)c2ccc(C(=O)Nc3ccccc3)cc2)C1=O]

(S)-4-(1-(2-ethyl-1-oxo-2,3-dihydro-1H-pyrrolo[3,4-c]pyridin-4-ylamino)ethyl)-N-phenylbenzamide Starting with Compound 12, Compound 13 of the present disclosure was prepared according to Scheme 7.

Step 1

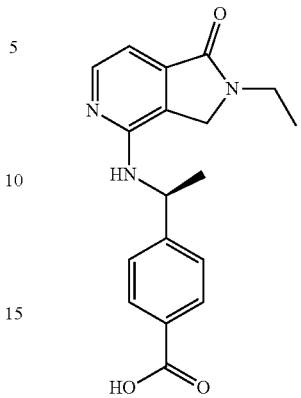

(S)-4-(1-((2-ethyl-1-oxo-2,3-dihydro-1H-pyrrolo[3,4-c]pyridin-4-yl)amino)ethyl)benzoic acid To a solution of Compound 12 (500 mg, 1.41 mmol) in THF (10 mL) was added a solution of NaOH (141 mg, 3.54 mmol) in water (5 mL). The reaction mixture was stirred at ambient temperature for 5 h. TLC indicated the reaction was completed. The mixture was concentrated to remove most of THF, diluted with water (10 mL), and acidified by addition of 2 N HCl solution to pH 7. The resulting precipitate was collected by filtration, washed by water (5 mL) and dried at 75 C in vacuo to give desired product as a white solid (330 mg, yield 71.7%).

Step 2

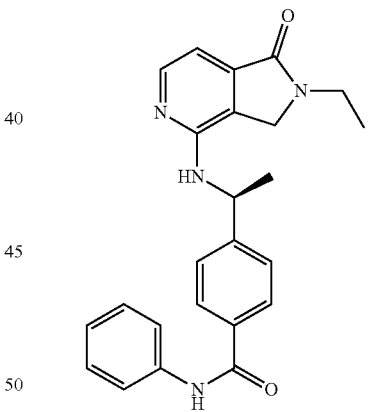

(S)-4-(1-((2-ethyl-1-oxo-2,3-dihydro-1H-pyrrolo[3,4-c]pyridin-4-yl)amino)ethyl)-N-phenylbenzamide To a solution of (S)-4-(1-((2-ethyl-1-oxo-2,3-dihydro-1H-pyrrolo[3,4-c]pyridin-4-yl)amino)ethyl)benzoic acid (320 mg, 0.98 mmol) in DMF (10 mL) was added aniline (110 mg, 1.18 mmol), DIPEA (254 mg, 1.97 mmol) and HATU (559 mg, 1.47 mmol). After addition, it was stirred at ambient temperature for 10 h. TLC indicated that the reaction was completed. The solvent was removed by concentration in vacuo and residue was dissolved in ethyl acetate (20 mL), washed by water (15 mL×2) and brine (15 mL). The separated organic layer was concentrated and the crude product was purified by silica gel column chromatography (eluted by DCM:MeOH=30:1) to give desired product as a white solid (120 mg, yield 30.5%).

1H NMR (400 MHz, CDCl3) δ 8.18 (d, J=5.1 Hz, 1H), 7.92 (s, 1H), 7.81 (d, J=8.2 Hz, 2H), 7.63 (d, J=7.8 Hz, 2H), 7.48 (d, J=8.2 Hz, 2H), 7.36 (t, J=7.9 Hz, 2H), 7.14 (t, J=7.4 Hz, 1H), 7.03 (d, J=5.2 Hz, 1H), 5.49-5.37 (m, 1H), 4.63 (d, J=6.3 Hz, 1H), 4.25 (d, J=2.6 Hz, 2H), 3.64 (q, J=7.2 Hz, 2H), 3.31-3.23 (m, 1H), 1.61 (d, J=6.9 Hz, 3H), 1.25 (t, J=7.3 Hz, 3H). ESI-MS m/z 401.2 [M+H].

Synthetic Example 14

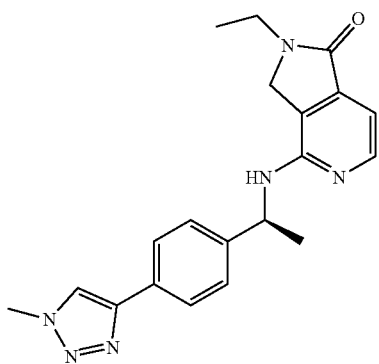 [SMILES: CCN1Cc2c(ccnc2N[C@@H](C)c2ccc(-c3cn(C)nn3)cc2)C1=O]

(S)-2-ethyl-4-(1-(4-(1-methyl-1H-1,2,3-triazol-4-yl)phenyl)ethylamino)-2,3-dihydro-1H-pyrrolo[3,4-c]pyridin-1-one Starting with Compound 1, Compound 14 of the present disclosure was prepared according to Scheme 8.

To a solution of Compound 1 (400 mg, 1.11 mmol) in dioxane/H2O (15 mL+5 mL) was added 1-methyl-4-(4,4,5,5-tetramethyl-1,3,2-dioxaborolan-2-yl)-1H-1,2,3-triazole (348 mg, 1.67 mmol), Cs2CO3 (724 mg, 2.22 mmol) and Pd(dppf)Cl2 (162 mg, 0.22 mmol). The reaction mixture was heated at 100 C for 4 h. TLC indicated that the reaction was completed. The solvent was removed by concentration in vacuo and the residue was dissolved in ethyl acetate (20 mL), washed by water (15 mL) and brine (15 mL). The separated organic layer was concentrated and the crude product was purified by preparative TLC (DCM:MeOH=20:1) to give desired product as a white solid (150 mg, yield 37.3%).

1H NMR (400 MHz, CDCl3) δ 8.20 (d, J=5.2 Hz, 1H), 7.77 (d, J=8.1 Hz, 2H), 7.71 (s, 1H), 7.45 (d, J=8.1 Hz, 2H), 7.03 (d, J=5.2 Hz, 1H), 5.40 (p, J=6.8 Hz, 1H), 4.66 (s, 1H), 4.23 (d, J=5.7 Hz, 2H), 4.12 (d, J=10.2 Hz, 3H), 3.68-3.59 (m, 2H), 1.62 (d, J=6.8 Hz, 3H), 1.24 (t, J=7.2 Hz, 3H). ESI-MS m/z 363.2 [M+H].

Synthetic Example 15

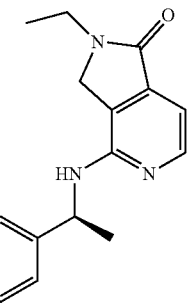

(S)-2-ethyl-4-(1-(4-(m-tolyloxy)phenyl)ethylamino)-2,3-dihydro-1H-pyrrolo[3,4-c]pyridin-1-one Compound 15 of the present disclosure was prepared according to Schemes 1, 2 and 6.

Step 1

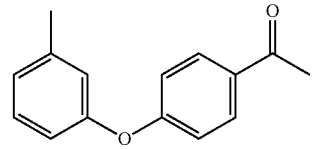 [SMILES: CC(=O)c1ccc(Oc2cccc(C)c2)cc1]

1-(4-(m-tolyloxy)phenyl)ethanone

To a solution of 1-(4-hydroxyphenyl)ethanone (3.00 g, 22.03 mmol) in DCM (30 mL) were added m-tolylboronic acid (4.50 g, 33.10 mmol), Cu(OAc)2 (8.00 g, 44.07 mmol) and TEA (11.15 g, 110.17 mmol). After addition, the mixture was stirred at ambient temperature for 12 h. TLC indicated that 1-(4-hydroxyphenyl)ethanone was consumed. Solid was removed by filtration, washed by DCM (10 mL) and filtrate was washed by water (30 mL). The separated organic layer was concentrated in vacuo and the crude product was purified by silica gel column chromatography (eluted by Petroleum ether:Ethyl acetate=20:1) to give desired product as a light yellow solid (2.00 g, yield 40.1%).

Step 2

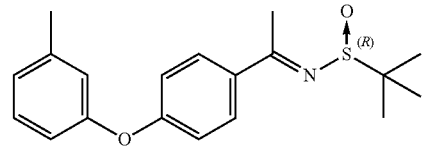

(RS)-2-methyl-N-(1-(4-(m-tolyloxy)phenyl)ethylidene)propane-2-sulfinamide

To a solution of 1-(4-(m-tolyloxy)phenyl)ethanone (1.50 g, 6.63 mmol) in THF (20 mL) were added (R)-(+)-2-methyl-2-propanesulfinamide (1.21 g, 9.94 mmol) and Ti(OEt)4 (4.54 g, 19.89 mmol). The reaction mixture was heated to reflux for 16 h. TLC indicated that starting material was consumed. It was cooled to ambient temperature, and then poured into aqueous saturated NaCl solution (50 mL). The resulting solid was removed by filtration, washed by ethyl acetate (10 mL). And filtrate was extracted with ethyl acetate (40 mL). The separated organic layer was dried over sodium sulfate, filtrated and concentrated to give the crude product (1.60 g, yield 73.3%), which was used in next step without further purification.

Step 3

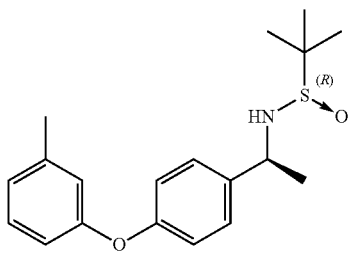

($R_s$)-2-methyl-N—((S)-1-(4-(m-tolyloxy)phenyl) ethyl)propane-2-sulfinamide

A mixture of ($R_S$)-2-methyl-N-(1-(4-(m-tolyloxy)phenyl) ethylidene)propane-2-sulfinamide (800 mg 2.30 mmol) and anhydrous THF (10 mL) was cooled to −50 C, L-selectride (1 M, 4.6 ml, 4.60 mmol) was dropped into the mixture at −50 C with stirring under $N_2$. The mixture was stirred for 1 h and then warmed to ambient temperature. On completion the reaction was quenched with water (50 mL), extracted with ethyl acetate (60 mL). The separated organic layer was concentrated in vacuo. The crude product was purified by silica gel column chromatography (eluted by Petroleum ether:Ethyl acetate=1:10) to give desired product (500 mg, yield 62.1%) as a yellow solid.

Step 4

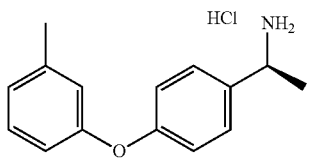 [SMILES: Cl ; Cc1cccc(Oc2ccc([C@H](C)N)cc2)c1]

(S)-1-(4-(m-tolyloxy)phenyl)ethanamine hydrochloride

To a solution of ($R_s$)-2-methyl-N—((S)-1-(4-(m-tolyloxy) phenyl)ethyl)propane-2-sulfinamide (450 mg, 1.28 mmol) in MeOH (5 mL) was added HCl/MeOH (4 M, 3.2 mL, 12.80 mmol). After addition, it was stirred for 16 h at ambient temperature. MeOH was removed under vacuum. Ethyl acetate (10 mL) was added into the residue and stirred for 30 min. Ethyl acetate was removed under vacuum, then MTBE (10 mL) was added into the residue and stirred for 1 h. The product was collected by filtration and washed by MTBE (5 mL), dried in vacuo to give desired product as a off-white solid (310 mg, yield 86.6%).

Step 5

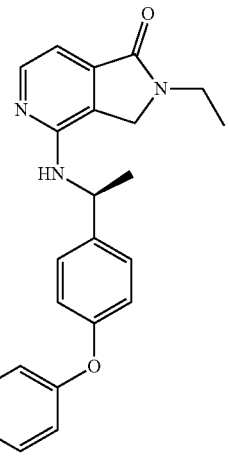

(S)-2-ethyl-4-((1-(4-(m-tolyloxy)phenyl)ethyl) amino)-2,3-dihydro-1H-pyrrolo[3,4-c]pyridin-1-one To a solution of 4-chloro-2-ethyl-2,3-dihydro-1H-pyrrolo [3,4-c]pyridin-1-one (120 mg, 0.61 mmol) in ethylene glycol (10 mL) which was obtained as in Synthesis Example 1 was added (S)-1-(4-(m-tolyloxy)phenyl)ethanamine hydrochloride (208 mg, 0.92 mmol) and TEA (185 mg, 1.83 mmol). The reaction mixture was heated to 150 C and stirred for 5 h. It was cooled to ambient temperature and diluted with 30 mL water, extracted with ethyl acetate (20 mL×2). The combined organic layers were dried over sodium sulfate, filtered and concentrated. The crude product was purified by preparative TLC (DCM:MeOH=20:1) to give desired product as a white solid (78 mg, yield 26.4%).

$^1$H NMR (400 MHz, CDCl$_3$) δ 8.23 (d, J=5.1 Hz, 1H), 7.36 (d, J=8.5 Hz, 2H), 7.20 (t, J=7.8 Hz, 1H), 7.04 (d, J=5.2 Hz, 1H), 6.96 (d, J=8.6 Hz, 2H), 6.91 (d, J=7.6 Hz, 1H), 6.86-6.75 (m, 2H), 5.46-5.31 (m, 1H), 4.49 (s, 1H), 4.21 (d, J=2.4 Hz, 2H), 3.65 (q, J=7.3 Hz, 2H), 2.32 (s, 3H), 1.61 (d, J=6.8 Hz, 3H), 1.25 (t, J=7.3 Hz, 3H). ESI-MS m/z 388.2 [M+H].

Synthetic Example 16

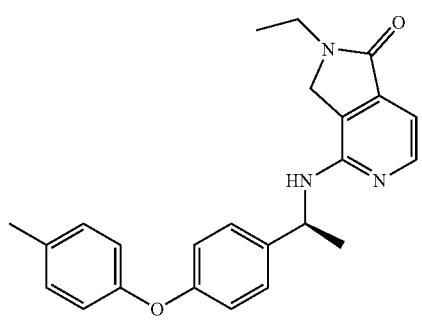 [SMILES: CCN1Cc2c(ccnc2N[C@@H](C)c2ccc(Oc3ccc(C)cc3)cc2)C1=O]

(S)-2-ethyl-4-(1-(4-(p-tolyloxy)phenyl)ethylamino)-2,3-dihydro-1H-pyrrolo [3,4-c]pyridin-1-one Compound 16 of the present disclosure was prepared according to Schemes 1, 2 and 6. The synthetic method was similar with Synthetic Example 15, except that the m-tolylboronic acid was replaced by p-tolylboronic acid.

$^1$H NMR (400 MHz, CDCl$_3$) δ 8.23 (d, J=5.1 Hz, 1H), 7.34 (d, J=8.5 Hz, 2H), 7.13 (d, J=8.2 Hz, 2H), 7.04 (d, J=5.2 Hz, 1H), 6.92 (dd, J=13.5, 8.5 Hz, 4H), 5.37 (p, J=6.6 Hz, 1H), 4.50 (s, 1H), 4.20 (d, J=1.6 Hz, 2H), 3.65 (q, J=7.3 Hz, 2H), 2.33 (s, 3H), 1.60 (d, J=6.8 Hz, 3H), 1.25 (t, J=7.3 Hz, 3H). ESI-MS m/z 388.2 [M+H].

Synthetic Example 17

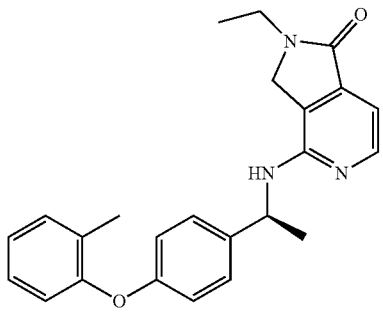 [SMILES: CCN1Cc2c(ccnc2N[C@@H](C)c2ccc(Oc3ccccc3C)cc2)C1=O]

(S)-2-ethyl-4-(1-(4-(o-tolyloxy)phenyl)ethylamino)-2,3-dihydro-1H-pyrrolo [3,4-c]pyridin-1-one Compound 17 of the present disclosure was prepared according to Schemes 1, 2 and 6. The synthetic method was similar with Synthetic Example 15, except that the m-tolylboronic acid was replaced by o-tolylboronic acid.

$^1$H NMR (400 MHz, CDCl$_3$) δ 8.23 (d, J=5.2 Hz, 1H), 7.33 (d, J=8.6 Hz, 2H), 7.26 (dd, J=8.7, 6.1 Hz, 1H), 7.20-7.11 (m, 2H), 7.06 (dd, J=12.4, 6.1 Hz, 2H), 6.88 (t, J=9.2 Hz, 2H), 5.37 (p, J=6.7 Hz, 1H), 4.48 (s, 1H), 4.20 (d, J=1.5 Hz, 2H), 3.65 (q, J=7.3 Hz, 2H), 2.36 (d, J=6.0 Hz, 2H), 2.23 (s, 3H), 1.59 (t, J=9.8 Hz, 3H), 1.25 (t, J=7.3 Hz, 3H). ESI-MS m/z 388.2 [M+H].

Synthetic Example 18

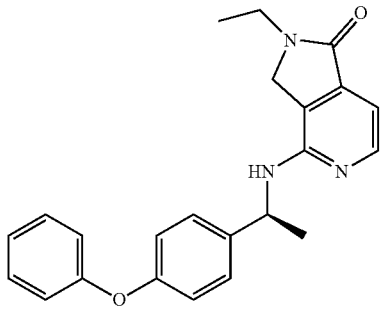 [SMILES: CCN1Cc2c(ccnc2N[C@@H](C)c2ccc(Oc3ccccc3)cc2)C1=O]

(S)-2-ethyl-4-(1-(4-phenoxyphenyl)ethylamino)-2,3-dihydro-1H-pyrrolo[3,4-c]pyridin-1-one Compound 18 of the present disclosure was prepared according to Schemes 1, 2 and 6. The synthetic method was similar with Synthetic Example 15, except that the m-tolylboronic acid was replaced by phenylboronic acid.

$^1$H NMR (400 MHz, CDCl$_3$) δ 8.23 (d, J=5.1 Hz, 1H), 7.41-7.28 (m, 4H), 7.10 (t, J=7.4 Hz, 1H), 7.04 (d, J=5.2 Hz, 1H), 6.98 (dd, J=11.8, 8.3 Hz, 4H), 5.39 (p, J=7.0 Hz, 1H), 4.48 (s, 1H), 4.21 (s, 2H), 3.65 (q, J=7.3 Hz, 2H), 1.61 (d, J=6.8 Hz, 3H), 1.25 (t, J=7.2 Hz, 3H). ESI-MS m/z 374.2 [M+H].

Synthetic Example 19

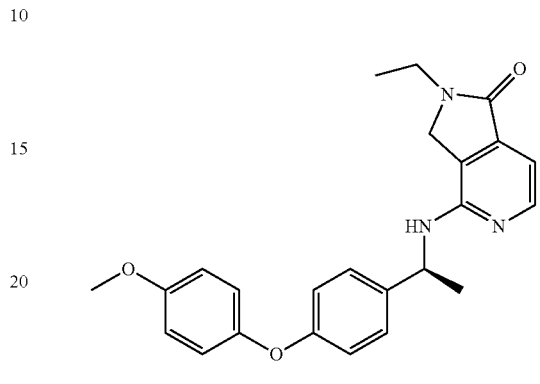

(S)-2-ethyl-4-(1-(4-(4-methoxyphenoxy)phenyl)ethylamino)-2,3-dihydro-1H-pyrrolo[3,4-c]pyridin-1-one Compound 19 of the present disclosure was prepared according to Schemes 1, 2 and 6. The synthetic method was similar with Synthetic Example 15, except that the m-tolylboronic acid was replaced by 4-methoxyphenylboronic acid.

$^1$H NMR (400 MHz, CDCl$_3$) δ 8.22 (d, J=5.1 Hz, 1H), 7.32 (d, J=8.6 Hz, 2H), 7.04 (d, J=5.2 Hz, 1H), 6.96 (d, J=9.0 Hz, 2H), 6.88 (dd, J=11.4, 8.8 Hz, 4H), 5.36 (p, J=6.9 Hz, 1H), 4.49 (s, 1H), 4.19 (s, 2H), 3.80 (s, 3H), 3.65 (q, J=7.2 Hz, 2H), 1.60 (d, J=6.8 Hz, 3H), 1.25 (t, J=7.2 Hz, 3H). ESI-MS m/z 404.2 [M+H].

Synthetic Example 20

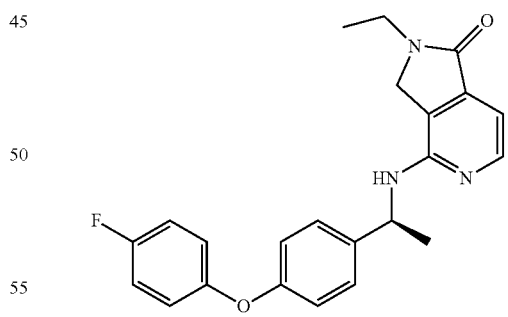

(S)-2-ethyl-4-(1-(4-(4-fluorophenoxy)phenyl)ethylamino)-2,3-dihydro-1H-pyrrolo[3,4-c]pyridin-1-one Compound 20 of the present disclosure was prepared according to Schemes 1, 2 and 6. The synthetic method was similar with Synthetic Example 15, except that the m-tolylboronic acid was replaced by 4-fluorophenylboronic acid.

$^1$H NMR (400 MHz, CDCl$_3$) δ 8.23 (d, J=5.1 Hz, 1H), 7.35 (d, J=8.5 Hz, 2H), 7.08-6.89 (m, 7H), 5.43-5.33 (m,

1H), 4.41 (s, 1H), 4.20 (s, 2H), 3.66 (q, J=7.2 Hz, 2H), 1.60 (d, J=6.8 Hz, 3H), 1.26 (t, J=7.3 Hz, 3H). ESI-MS m/z 392.2 [M+H].

Synthetic Example 21

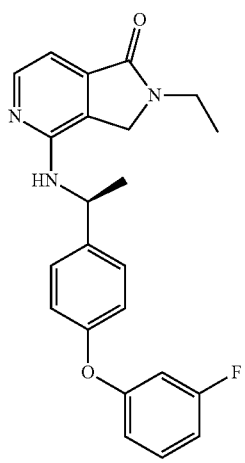 [SMILES: CCN1Cc2c(ccnc2N[C@@H](C)c2ccc(Oc3cccc(F)c3)cc2)C1=O]

(S)-2-ethyl-4-((1-(4-(3-fluorophenoxy)phenyl)ethyl)amino)-2,3-dihydro-1H-pyrrolo[3,4-c]pyridin-1-one Compound 21 of the present disclosure was prepared according to Schemes 1, 2 and 6. The synthesis and characterization methods for Compound 21 were similar with Synthetic Example 15, except that the m-tolylboronic acid was replaced by 3-fluorophenylboronic acid.

Synthetic Example 22

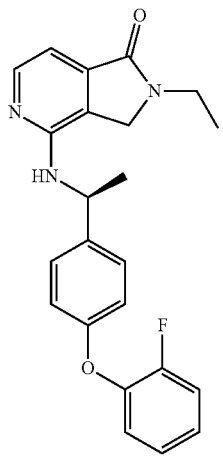 [SMILES: CCN1Cc2c(ccnc2N[C@@H](C)c2ccc(Oc3ccccc3F)cc2)C1=O]

(S)-2-ethyl-4-((1-(4-(2-fluorophenoxy)phenyl)ethyl)amino)-2,3-dihydro-1H-pyrrolo[3,4-c]pyridin-1-one Compound 22 of the present disclosure was prepared according to Schemes 1, 2 and 6. The synthesis and characterization methods for Compound 22 were similar with Synthetic Example 15, except that the m-tolylboronic acid was replaced by 2-fluorophenylboronic acid.

Synthetic Example 23

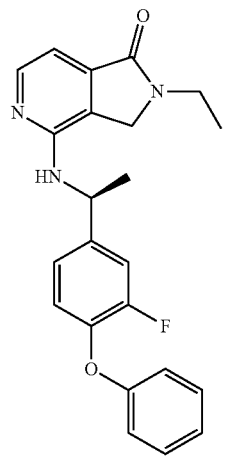 [SMILES: CCN1Cc2c(ccnc2N[C@@H](C)c2ccc(Oc3ccccc3)c(F)c2)C1=O]

(S)-2-ethyl-4-((1-(3-fluoro-4-phenoxyphenyl)ethyl)amino)-2,3-dihydro-1H-pyrrolo[3,4-c]pyridin-1-one Compound 23 of the present disclosure was prepared according to Schemes 1, 2 and 6. The synthesis and characterization methods for Compound 23 were similar with Synthetic Example 15, except that the 1-(4-hydroxyphenyl)ethanone was replaced by 1-(3-fluoro-4-hydroxyphenyl)ethanone, and the m-tolylboronic acid was replaced by phenylboronic acid.

Synthetic Example 24

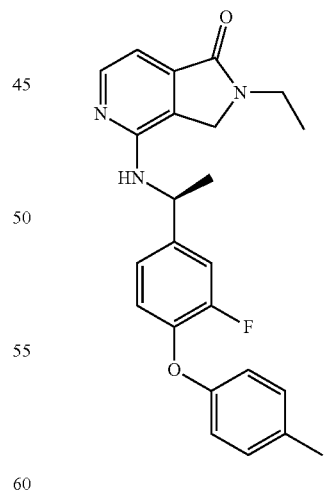

(S)-2-ethyl-4-((1-(3-fluoro-4-(p-tolyloxy)phenyl)ethyl)amino)-2,3-dihydro-1H-pyrrolo[3,4-c]pyridin-1-one Compound 24 of the present disclosure was prepared according to Schemes 1, 2 and 6. The synthesis and characterization methods for Compound 24 were similar with Synthetic Example 15, except that the 1-(4-hydroxyphenyl)ethanone was replaced by 1-(3-fluoro-4-hydroxyphenyl)ethanone, and the m-tolylboronic acid was replaced by p-tolylboronic acid.

Synthetic Example 25

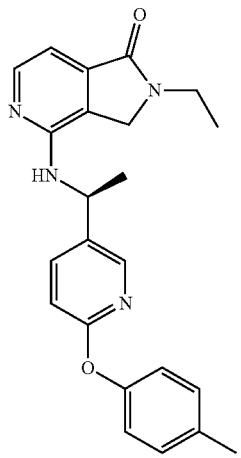 [SMILES: CCN1Cc2c(ccnc2N[C@@H](C)c2ccc(Oc3ccc(C)cc3)nc2)C1=O]

(S)-2-ethyl-4-((1-(6-(p-tolyloxy)pyridin-3-yl)ethyl)amino)-2,3-dihydro-1H-pyrrolo[3,4-c]pyridin-1-one Compound 25 of the present disclosure was prepared according to Schemes 1, 3 and 6.

Step 1

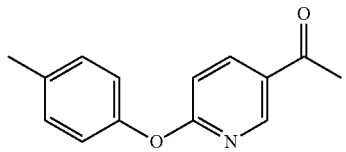 [SMILES: CC(=O)c1ccc(Oc2ccc(C)cc2)nc1]

1-(6-(p-tolyloxy)pyridin-3-yl)ethanone

To a solution of 1-(6-chloropyridin-3-yl)ethanone (2.00 g, 12.85 mmol) in toluene (20 mL) were added p-cresol (2.09 g, 19.28 mmol), CuI (450 mg, 2.57 mmol) and $Cs_2CO_3$ (8.38 g, 25.71 mmol). The reaction mixture was heated to reflux for 5 h. TLC indicated that the reaction was completed. The solid was removed by filtration, washed by toluene (5 mL). The filtrate was washed by sat. $NaHCO_3$ aqueous solution (15 mL) and brine (15 mL). The separated organic layer was concentrated and the crude product was purified by silica gel column chromatography (eluted by Petroleum ether:Ethyl acetate=6:1) to give desired product as a white solid (1.80 g, yield 61.6%).

Step 2

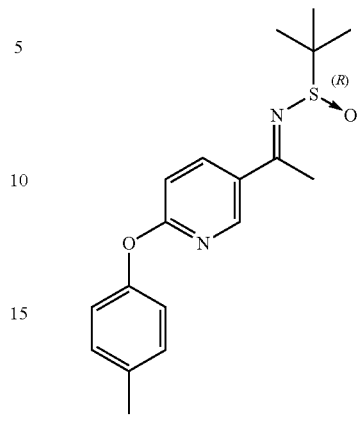

($R_S$)-2-methyl-N-(1-(6-(p-tolyloxy)pyridin-3-yl)ethylidene)propane-2-sulfinamide To a solution of 1-(6-(p-tolyloxy)pyridin-3-yl)ethanone (1.50 g, 6.60 mmol) in THF (20 mL) were added (R)-(+)-2-methyl-2-propanesulfinamide (1.20 g, 9.90 mmol) and Ti(OEt)$_4$ (4.52 g, 19.80 mmol). The reaction mixture was heated to reflux for 16 h. TLC indicated that starting material was consumed. It was cooled to ambient temperature, and then poured into aqueous saturated NaCl solution (50 mL). The resulting solid was removed by filtration, washed by ethyl acetate (10 mL). And filtrate was extracted with ethyl acetate (40 mL). The separated organic layer was dried over sodium sulfate, filtrated and concentrated to give the crude product (1.70 g, yield 77.9%), which was used in next step without further purification.

Step 3

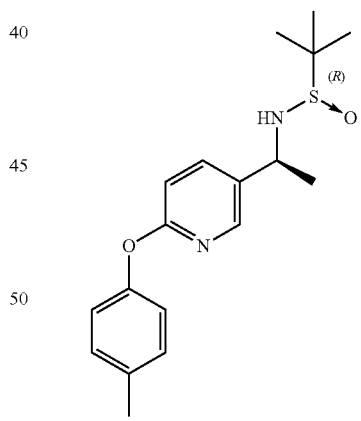

($R_S$)-2-methyl-N—((S)-1-(6-(p-tolyloxy)pyridin-3-yl)ethyl)propane-2-sulfinamide A mixture of ($R_S$)-2-methyl-N-(1-(6-(p-tolyloxy)pyridin-3-yl)ethylidene)propane-2-sulfinamide (800 mg 2.42 mmol) and anhydrous THF (10 mL) was cooled to −50° C., L-selectride (1 M, 4.6 ml, 4.60 mmol) was dropped into the mixture at −50° C. with stirring under $N_2$. The mixture was stirred for 1 h and then warmed to ambient temperature. On completion the reaction was quenched with water (50 mL), extracted with ethyl acetate (60 mL). The separated organic layer was concentrated in vacuo. The crude product was purified by silica gel column chromatography (eluted by Petroleum ether:Ethyl acetate=1:10) to give desired product (500 mg, yield 62.1%) as a yellow solid.

Step 4

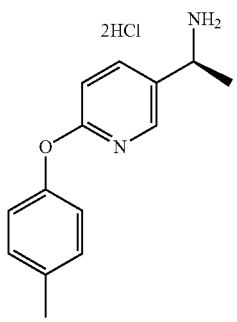 [SMILES: Cc1ccc(Oc2ccc([C@H](C)N)cn2)cc1]

(S)-1-(6-(p-tolyloxy)pyridin-3-yl)ethanamine dihydrochloride

To a solution of (R$_S$)-2-methyl-N—((S)-1-(6-(p-tolyloxy) pyridin-3-yl)ethyl)propane-2-sulfinamide (450 mg, 1.35 mmol) in MeOH (5 mL) was added HCl/MeOH (4 M, 3.4 mL, 13.50 mmol). After addition, it was stirred for 16 h at ambient temperature. MeOH was removed under vacuum. Ethyl acetate (10 mL) was added into the residue and stirred for 30 min. Ethyl acetate was removed under vacuum, then MTBE (10 mL) was added into the residue and stirred for 1 h. The product was collected by filtration and washed by MTBE (5 mL), dried in vacuo to give desired product as an off-white solid (310 mg, yield 76.0%).

Step 5

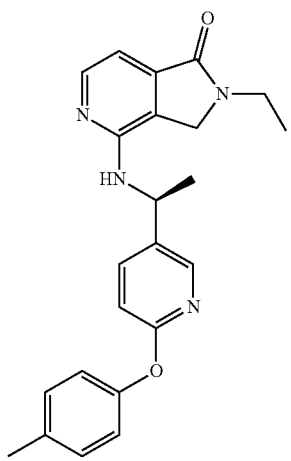 [SMILES: CCN1Cc2c(ccnc2N[C@@H](C)c2ccc(Oc3ccc(C)cc3)nc2)C1=O]

(S)-2-ethyl-4-((1-(6-(p-tolyloxy)pyridin-3-yl)ethyl) amino)-2,3-dihydro-1H-pyrrolo[3,4-c]pyridin-1-one To a solution of 4-chloro-2-ethyl-2,3-dihydro-1H-pyrrolo [3,4-c]pyridin-1-one (120 mg, 0.61 mmol) in ethylene glycol (10 mL) was added (S)-1-(4-(p-tolyloxy)phenyl)ethanamine hydrochloride (276 mg, 0.92 mmol) and TEA (247 mg, 2.44 mmol). The reaction mixture was heated to 150° C. and stirred for 5 h. It was cooled to ambient temperature and diluted with 30 mL water, extracted with ethyl acetate (20 mL×2). The combined organic layers were dried over sodium sulfate, filtered and concentrated. The crude product was purified by preparative TLC (DCM:MeOH=20:1) to give Compound 25 as a white solid (60 mg, 25.3%), which was further characterized by NMR and MS.

Synthetic Example 26

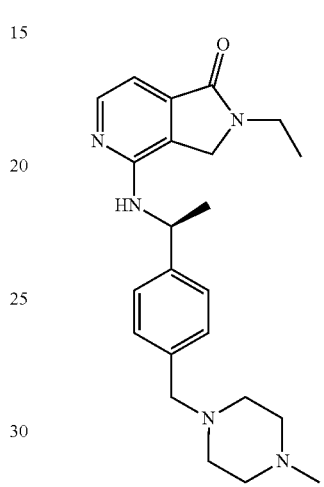

(S)-2-ethyl-4-((1-(4-((4-methylpiperazin-1-yl) methyl)phenyl)ethyl)amino)-2,3-dihydro-1H-pyrrolo [3,4-c]pyridin-1-one Compound 26 of the present disclosure was prepared according to Schemes 1, 4 and 6.

Step 1

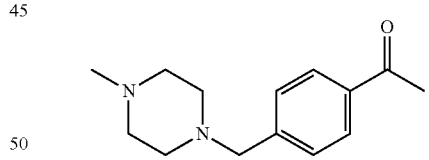

1-(4-((4-methylpiperazin-1-yl)methyl)phenyl)ethanone

To a solution of 1-(4-(bromomethyl)phenyl)ethanone (5.00 g, 23.47 mmol) in Toluene (50 mL) were added 1-methylpiperazine (2.35 g, 23.47 mmol) and K$_2$CO$_3$ (3.89 g, 28.16 mmol). After addition, it was heated at 70° C. for 3 h. TLC indicated that the reaction was completed. The solid was removed by filtration and washed by Toluene (5 mL). The filtrate was concentrated in vacuo and the crude product was purified by silica gel column chromatography (eluted by Petroleum ether:Ethyl acetate=3:1) to give desired product (2.80 g, yield 51.4%) as a light yellow oil.

Step 2

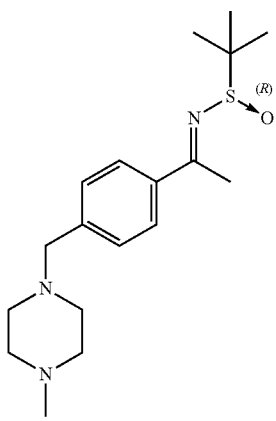

($R_S$)-2-methyl-N-(1-(4-((4-methylpiperazin-1-yl)methyl)phenyl)ethylidene)propane-2-sulfinamide To a solution of 1-(4-((4-methylpiperazin-1-yl)methyl)phenyl)ethanone (1.50 g, 6.46 mmol) in THF (20 mL) were added (R)-(+)-2-methyl-2-propanesulfinamide (1.17 g, 9.68 mmol) and Ti(OEt)₄ (4.42 g, 19.37 mmol). The reaction mixture was heated to reflux for 16 h. TLC indicated that starting material was consumed. It was cooled to ambient temperature, and then poured into aqueous saturated NaCl solution (50 mL). The resulting solid was removed by filtration, washed by ethyl acetate (10 mL). And filtrate was extracted with ethyl acetate (40 mL). The separated organic layer was dried over sodium sulfate, filtrated and concentrated to give the crude product (1.70 g, yield 78.5%), which was used in next step without further purification.

Step 3

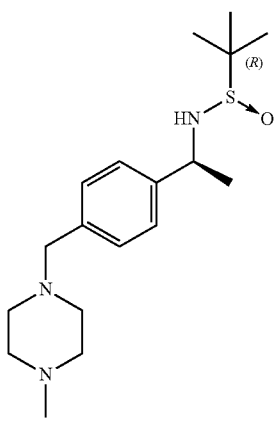

($R_S$)-2-methyl-N—((S)-1-(4-((4-methylpiperazin-1-yl)methyl)phenyl)ethyl)propane-2-sulfinamide A mixture of ($R_S$)-2-methyl-N-(1-(4-((4-methylpiperazin-1-yl)methyl)phenyl)ethylidene)propane-2-sulfinamide (800 mg 2.38 mmol) and anhydrous THF (10 mL) was cooled to −50 C, L-selectride (1 M, 4.8 ml, 4.76 mmol) was dropped into the mixture at −50 C with stirring under N₂. The mixture was stirred for 1 h and then warmed to ambient temperature. On completion the reaction was quenched with water (50 mL), extracted with ethyl acetate (60 mL). The separated organic layer was concentrated in vacuo. The crude product was purified by silica gel column chromatography (eluted by DCM:MeOH=20:1) to give desired product (550 mg, yield 68.3%) as a yellow solid.

Step 4

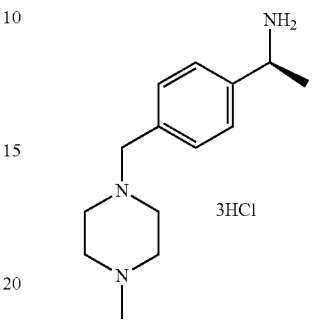

(S)-1-(4-((4-methylpiperazin-1-yl)methyl)phenyl)ethanamine trihydrochloride

To a solution of ($R_S$)-2-methyl-N—((S)-1-(4-((4-methylpiperazin-1-yl)methyl)phenyl)ethyl)propane-2-sulfinamide (450 mg, 1.33 mmol) in MeOH (5 mL) was added HCl/MeOH (4 M, 3.3 mL, 13.30 mmol). After addition, it was stirred for 16 h at ambient temperature. MeOH was removed under vacuum. Ethyl acetate (10 mL) was added into the residue and stirred for 30 min. Ethyl acetate was removed under vacuum, then MTBE (10 mL) was added into the residue and stirred for 1 h. The product was collected by filtration and washed by MTBE (5 mL), dried in vacuo to give desired product as a off-white solid (350 mg, yield 76.6%).

Step 5

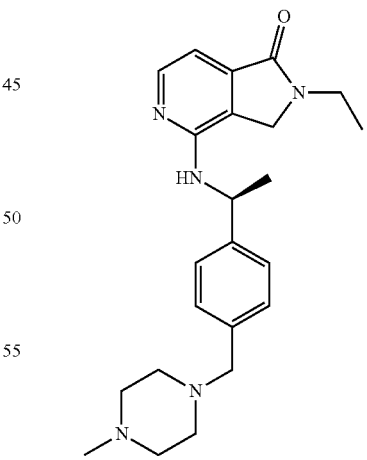

(S)-2-ethyl-4-((1-(4-((4-methylpiperazin-1-yl)methyl)phenyl)ethyl)amino)-2,3-dihydro-1H-pyrrolo[3,4-c]pyridin-1-one To a solution of 4-chloro-2-ethyl-2,3-dihydro-1H-pyrrolo[3,4-c]pyridin-1-one (120 mg, 0.61 mmol) in ethylene glycol (10 mL) was added (S)-1-(4-((4-methylpiperazin-1-yl) methyl) phenyl)ethanamine trihydrochloride (314 mg, 0.92 mmol) and TEA (247 mg, 2.44 mmol). The reaction mixture was heated to 150 C and stirred for 5 h. It was cooled to ambient temperature and diluted with 30 mL water, extracted with ethyl acetate (20 mL×2). The combined organic layers were dried over sodium sulfate, filtered and concentrated. The crude product was purified by preparative TLC (DCM:MeOH=20:1) to give Compound 26 as a white solid (52 mg, yield 21.7%), which was further characterized by NMR and MS.

Synthetic Example 27

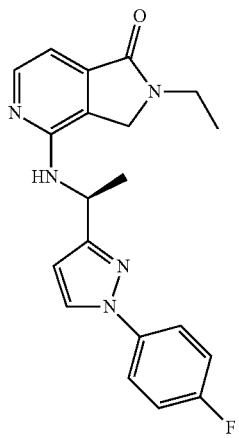 [SMILES: CCN1Cc2c(ccnc2N[C@@H](C)c2ccn(-c3ccc(F)cc3)n2)C1=O]

(S)-2-ethyl-4-((1-(1-(4-fluorophenyl)-1H-pyrazol-3-yl)ethyl)amino)-2,3-dihydro-1H-pyrrolo[3,4-c]pyridin-1-one Compound 27 of the present disclosure was prepared according to Schemes 1, 5 and 6.

Step 1

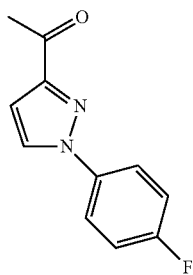

1-(1-(4-fluorophenyl)-1H-pyrazol-3-yl)ethanone

To a solution of 1-(1H-pyrazol-3-yl)ethanone (5.00 g, 45.41 mmol) in DCM (50 mL) were added (4-fluorophenyl) boronic acid (9.53 g, 68.11 mmol), Cu(OAc)$_2$ (16.50 g, 90.82 mmol) and TEA (22.97 g, 227.04 mmol). After addition, the mixture was stirred at ambient temperature for 12 h. TLC indicated that 1-(1H-pyrazol-3-yl)ethanone was consumed. Solid was removed by filtration, washed by DCM (20 mL) and filtrate was washed by water (50 mL). The separated organic layer was concentrated in vacuo and the crude product was purified by silica gel column chromatography (eluted by Petroleum ether:Ethyl acetate=5:1) to give desired product as a light yellow solid (3.1 g, yield 33.4%).

Step 2

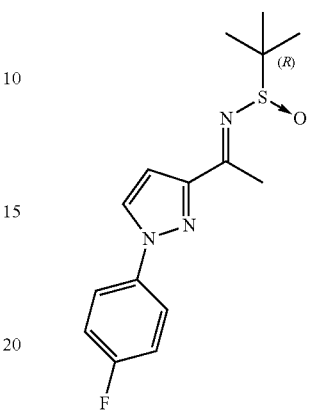

(R$_S$)—N-(1-(1-(4-fluorophenyl)-1H-pyrazol-3-yl)ethylidene)-2-methylpropane-2-sulfinamide To a solution of 1-(1-(4-fluorophenyl)-1H-pyrazol-3-yl) ethanone (1.50 g, 7.35 mmol) in THF (20 mL) were added (R)-(+)-2-methyl-2-propanesulfinamide (1.34 g, 11.02 mmol) and Ti(OEt)$_4$ (5.03 g, 22.04 mmol). The reaction mixture was heated to reflux for 16 h. TLC indicated that starting material was consumed. It was cooled to ambient temperature, and then poured into aqueous saturated NaCl solution (50 mL). The resulting solid was removed by filtration, washed by ethyl acetate (10 mL). And filtrate was extracted with ethyl acetate (40 mL). The separated organic layer was dried over sodium sulfate, filtrated and concentrated to give the crude product (1.90 g, yield 84.2%), which was used in next step without further purification.

Step 3

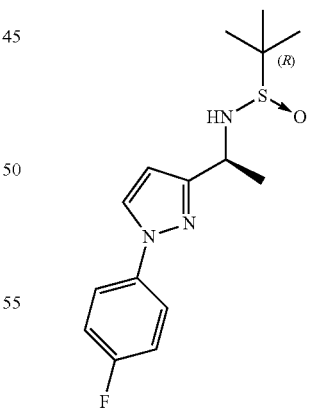

(R$_S$)—N—((S)-1-(1-(4-fluorophenyl)-1H-pyrazol-3-yl)ethyl)-2-methylpropane-2-sulfinamide A mixture of (R$_S$)—N-(1-(1-(4-fluorophenyl)-1H-pyrazol-3-yl)ethylidene)-2-methylpropane-2-sulfinamide (800 mg 2.60 mmol) and anhydrous THF (10 mL) was cooled to −50° C., L-selectride (1 M, 5.2 mL, 5.20 mmol) was dropped into the mixture at −50° C. with stirring under N₂. The mixture was stirred for 1 h and then warmed to ambient temperature. On completion the reaction was quenched with water (50 mL), extracted with ethyl acetate (60 mL). The separated organic layer was concentrated in vacuo. The crude product was purified by silica gel column chromatography (eluted by Petroleum ether:Ethyl acetate=1:15) to give desired product (360 mg, yield 44.7%) as a yellow solid.

Step 4

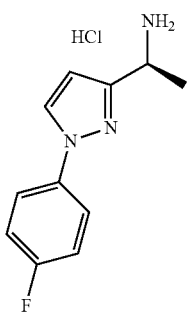

(S)-1-(1-(4-fluorophenyl)-1H-pyrazol-3-yl)ethanamine hydrochloride

To a solution of (R$_S$)—N—((S)-1-(1-(4-fluorophenyl)-1H-pyrazol-3-yl)ethyl)-2-methylpropane-2-sulfinamide (360 mg, 1.16 mmol) in MeOH (5 mL) was added HCl/MeOH (4 M, 2.9 mL, 11.60 mmol). After addition, it was stirred for 16 h at ambient temperature. MeOH was removed under vacuum. Ethyl acetate (10 mL) was added into the residue and stirred for 30 min. Ethyl acetate was removed under vacuum, then MTBE (10 mL) was added into the residue and stirred for 1 h. The product was collected by filtration and washed by MTBE (5 mL), dried in vacuo to give desired product as a off-white solid (240 mg, yield 85.3%).

Step 5

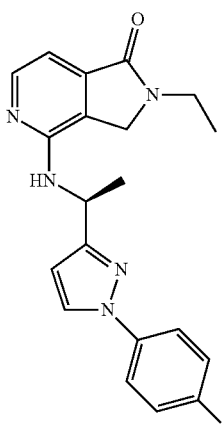

(S)-2-ethyl-4-((1-(1-(4-fluorophenyl)-1H-pyrazol-3-yl)ethyl)amino)-2,3-dihydro-1H-pyrrolo[3,4-c]pyridin-1-one To a solution of 4-chloro-2-ethyl-2,3-dihydro-1H-pyrrolo[3,4-c]pyridin-1-one (120 mg, 0.61 mmol) in ethylene glycol (10 mL) was added (S)-1-(1-(4-fluorophenyl)-1H-pyrazol-3-yl) ethanamine hydrochloride (221 mg, 0.92 mmol) and TEA (185 mg, 1.83 mmol). The reaction mixture was heated to 150 C and stirred for 5 h. It was cooled to ambient temperature and diluted with 30 mL water, extracted with ethyl acetate (20 mL×2). The combined organic layers were dried over sodium sulfate, filtered and concentrated. The crude product was purified by preparative TLC (DCM: MeOH=20:1) to give Compound 27 as a white solid (40 mg, 17.9%), which was further characterized by NMR and MS.

Synthetic Example 28

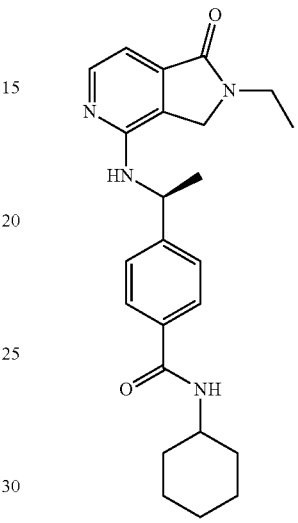

(S)—N-cyclohexyl-4-(1-((2-ethyl-1-oxo-2,3-dihydro-1H-pyrrolo[3,4-c]pyridin-4-yl)amino)ethyl) benzamide Starting with Compound 12, Compound 28 of the present disclosure was prepared according to Scheme 7. The synthesis and characterization methods were similar with Synthetic Example 13, except that the aniline was replaced by cyclohexylamine.

Synthetic Example 29

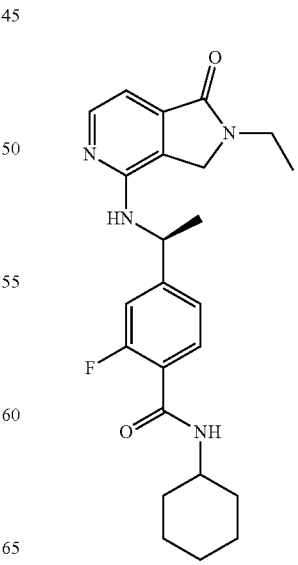

(S)—N-cyclohexyl-4-(1-((2-ethyl-1-oxo-2,3-di-hydro-1H-pyrrolo[3,4-c]pyridin-4-yl)amino)ethyl)-2-fluorobenzamide Compound 29 of the present disclosure was prepared according to Schemes 1, 6 and 7. The starting compound for preparing Compound 29 (similar to 1026 shown in Scheme 7) was synthesized as in Synthetic Example 1, except that the (S)-1-(4-bromophenyl)ethanamine was replaced by (S)-ethyl-2-fluoro-4-((1-amino)ethyl)-benzoate. Using the obtained starting compound, Compound 29 was prepared as in Synthetic Example 13, except that the aniline was replaced by cyclohexylamine, and was further characterized by NMR and MS.

Synthetic Example 30

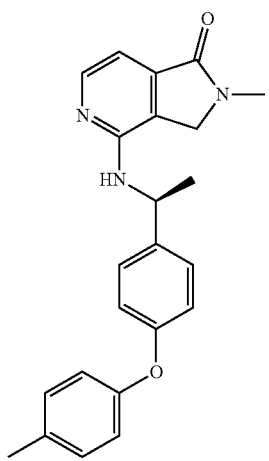

(S)-2-methyl-4-((1-(4-(p-tolyloxy)phenyl)ethyl)amino)-2,3-dihydro-1H-pyrrolo[3,4-c]pyridin-1-one Compound 30 of the present disclosure was prepared according to Schemes 1, 2 and 6. The synthetic method was similar with Synthetic Example 15, except that the m-tolylboronic acid was replaced by p-tolylboronic acid, and 4-chloro-2-ethyl-2,3-dihydro-1H-pyrrolo-[3,4-c]pyridin-1-one was replaced by 4-chloro-2-methyl-2,3-dihydro-1H-pyrrolo-[3,4-c]pyridin-1-one, which was obtained as in Synthesis Example 1 except that ethanamine hydrochloride was replaced by methylamine. Compound 30 was further characterized by NMR and MS.

Synthetic Example 31

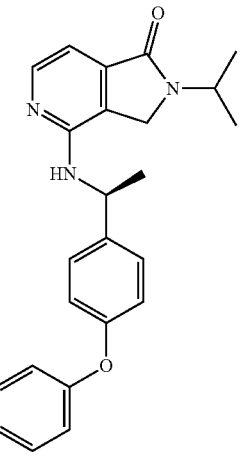

(S)-2-isopropyl-4-((1-(4-(p-tolyloxy)phenyl)ethyl)amino)-2,3-dihydro-1H-pyrrolo[3,4-c]pyridin-1-one Compound 31 of the present disclosure was prepared according to Schemes 1, 2 and 6. The synthetic method was similar with Synthetic Example 15, except that the m-tolylboronic acid was replaced by p-tolylboronic acid, and 4-chloro-2-ethyl-2,3-dihydro-1H-pyrrolo-[3,4-c]pyridin-1-one was replaced by 4-chloro-2-isopropyl-2,3-dihydro-1H-pyrrolo-[3,4-c]pyridin-1-one, which was obtained as in Synthesis Example 1 except that ethanamine hydrochloride was replaced by isopropylamine. Compound 31 was further characterized by NMR and MS.

Synthetic Example 32

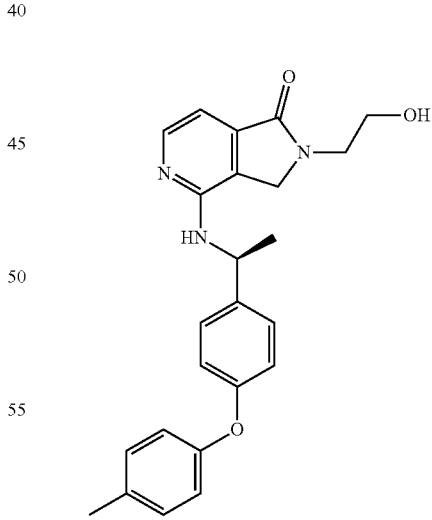

(S)-2-(2-hydroxyethyl)-4-((1-(4-(p-tolyloxy)phenyl)ethyl)amino)-2,3-dihydro-1H-pyrrolo[3, 4-c]pyridin-1-one Compound 32 of the present disclosure was prepared according to Schemes 1, 2 and 6. The synthetic method was similar with Synthetic Example 15, except that the m-tolyl-boronic acid was replaced by p-tolylboronic acid, and 4-chloro-2-ethyl-2,3-dihydro-1H-pyrrolo[3,4-c]pyridin-1-one was replaced by 4-chloro-2-(2-hydroxyethyl)-2,3-dihydro-1H-pyrrolo-[3,4-c]pyridin-1-one, which was obtained as in Synthesis Example 1 except that ethanamine hydrochloride was replaced by 2-hydroxyethanamine. Compound 32 was further characterized by NMR and MS.

Synthetic Example 33

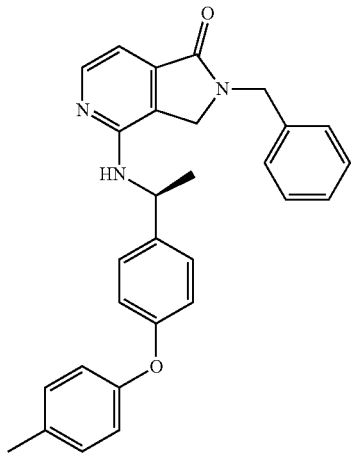 [SMILES: Cc1ccc(Oc2ccc([C@H](C)Nc3nccc4c3CN(Cc3ccccc3)C4=O)cc2)cc1]

(S)-2-benzyl-4-((1-(4-(p-tolyloxy)phenyl)ethyl)amino)-2,3-dihydro-1H-pyrrolo[3,4-c]pyridin-1-one Compound 33 of the present disclosure was prepared according to Schemes 1, 2 and 6. The synthetic method was similar with Synthetic Example 15, except that the m-tolyl-boronic acid was replaced by p-tolylboronic acid, and 4-chloro-2-ethyl-2,3-dihydro-1H-pyrrolo[3,4-c]pyridin-1-one was replaced by 4-chloro-2-benzyl-2,3-dihydro-1H-pyrrolo-[3,4-c]pyridin-1-one, which was obtained as in Synthesis Example 1 except that ethanamine hydrochloride was replaced by benzylamine. Compound 33 was further characterized by NMR and MS.

Synthetic Example 34

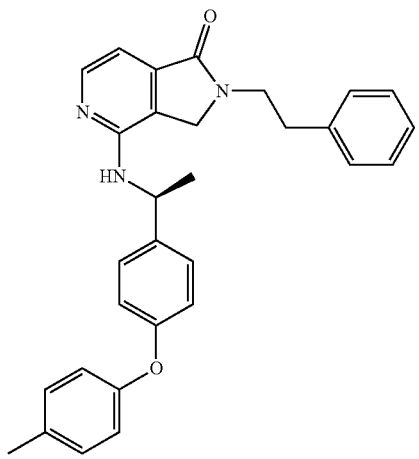 [SMILES: Cc1ccc(Oc2ccc([C@H](C)Nc3nccc4c3CN(CCc3ccccc3)C4=O)cc2)cc1]

(S)-2-phenethyl-4-((1-(4-(p-tolyloxy)phenyl)ethyl)amino)-2,3-dihydro-1H-pyrrolo[3,4-c]pyridin-1-one Compound 34 of the present disclosure was prepared according to Schemes 1, 2 and 6. The synthetic method was similar with Synthetic Example 15, except that the m-tolyl-boronic acid was replaced by p-tolylboronic acid, and 4-chloro-2-ethyl-2,3-dihydro-1H-pyrrolo[3,4-c]pyridin-1-one was replaced by 4-chloro-2-phenethyl-2,3-dihydro-1H-pyrrolo[3,4-c]-pyridin-1-one, which was obtained as in Synthesis Example 1 except that ethanamine hydrochloride was replaced by phenethylamine. Compound 34 was further characterized by NMR and MS.

Synthetic Example 35

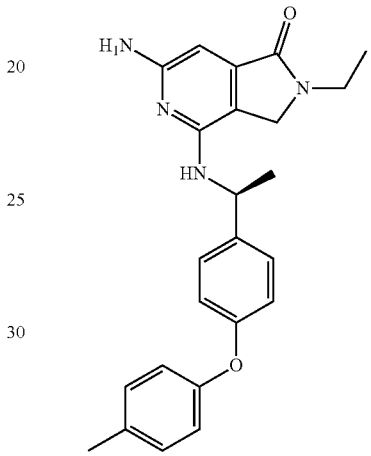

(S)-6-amino-2-ethyl-4-((1-(4-(p-tolyloxy)phenyl)ethyl)amino)-2,3-dihydro-1H-pyrrolo[3,4-c]pyridin-1-one Compound 35 of the present disclosure was prepared according to Schemes 1, 2, 6 and 9.

Step 1

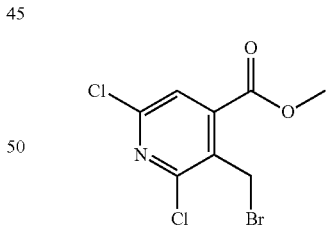

Methyl 3-(bromomethyl)-2,6-dichloroisonicotinate

To a solution of methyl 2,6-dichloro-3-methylisonicotinate (10.00 g, 45.44 mmol) in $CCl_4$ (100 mL) was added NBS (8.90 g, 49.99 mmol) and BPO (550 mg, 2.27 mmol). After addition, the reaction mixture was heated to reflux for 4 h. TLC indicated that starting material was consumed. Then, it was cooled to ambient temperature and the resulting precipitate was removed by filtration, washed by $CCl_4$ (10 mL). The filtrate was concentrated in vacuo to give the crude product as a yellow solid, which was used in next step without further purification.

Step 2

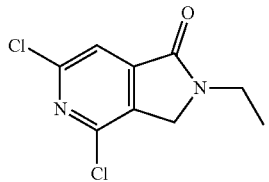

4,6-dichloro-2-ethyl-2,3-dihydro-1H-pyrrolo[3,4-c]pyridin-1-one

The above crude product was dissolved in THF (100 mL). Ethanamine hydrochloride (3.71 g, 45.44 mmol) and Cs$_2$CO$_3$ (59.23 g, 181.77 mmol) were added into the reaction mixture. It was stirred at ambient temperature for 12 h. TLC indicated that starting material was consumed. The solid was removed by filtration, washed by ethyl acetate (15 mL) and the filtrate was concentrated in vacuo. The crude product was purified by silica gel column chromatography (eluted by Petroleum ether:Ethyl acetate=2:1) to give desired product as light yellow solid (5.40 g, yield 51.4% in two steps).

Step 3

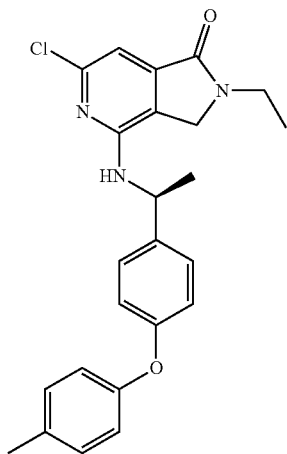 [SMILES: CCN1Cc2c(cc(Cl)nc2N[C@@H](C)c2ccc(Oc3ccc(C)cc3)cc2)C1=O]

(S)-6-chloro-2-ethyl-4-((1-(4-(p-tolyloxy)phenyl)ethyl)amino)-2,3-dihydro-1H-pyrrolo[3,4-c]pyridin-1-one To a solution of 4,6-dichloro-2-ethyl-2,3-dihydro-1H-pyrrolo[3,4-c]pyridin-1-one (4.00 g, 17.31 mmol) in ethylene glycol (40 mL) was added (S)-1-(4-(p-tolyloxy)phenyl)ethanamine (5.12 g, 22.50 mmol) and TEA (2.63 g, 25.97 mmol). The reaction mixture was heated to 150 C and stirred for 7 h. It was cooled to ambient temperature and diluted with 80 mL water, extracted with ethyl acetate (100 mL×2). The combined organic layers were dried over sodium sulfate, filtered and concentrated. The crude product was purified by silica gel column chromatography (eluted by DCM:MeOH=30:1) to give desired product (3.20 g, yield 43.8%).

Step 4

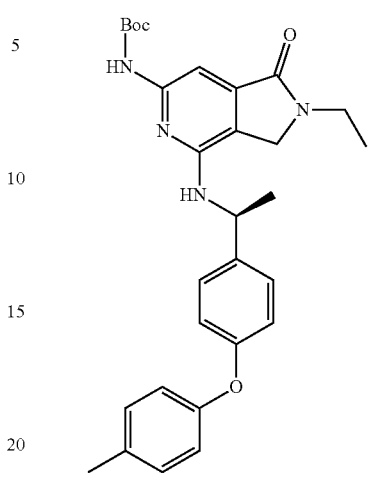

(S)-tert-butyl (2-ethyl-1-oxo-4-((1-(4-(p-tolyloxy)phenyl)ethyl)amino)-2,3-dihydro-1H-pyrrolo[3,4-c]pyridin-6-yl)carbamate To a solution of (S)-6-chloro-2-ethyl-4-((1-(4-(p-tolyloxy)phenyl)ethyl)amino)-2,3-dihydro-1H-pyrrolo[3,4-c]pyridin-1-one (2.00 g, 4.74 mmol) in Dioxane (20 mL) were added tert-butyl carbamate (1.11 g, 9.50 mmol), t-BuOK (1.42 g, 12.67 mmol), Pd(PPh$_3$)$_4$ (548 mg, 0.47 mmol) and X-phos (226 mg, 0.47 mmol). It was heated at 80 C under the atmosphere of N$_2$ for 5 h. TLC indicated that the reaction was completed. The solvent was removed by concentration in vacuo and residue was dissolved in DCM (150 mL), washed by water (100 mL×2) and brine (100 mL). The separated organic layer was concentrated and the crude product was purified by silica gel column chromatography (eluted by DCM:MeOH=30:1) to give desired product as a yellow solid (1.50 g, yield 63.0%).

Step 5

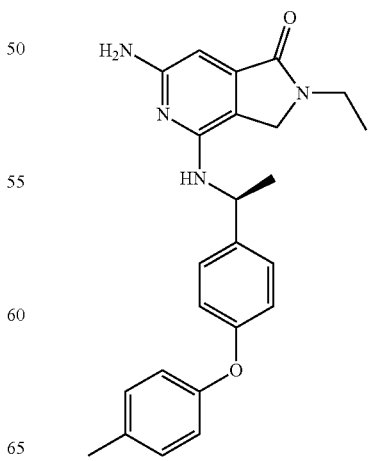

(S)-6-amino-2-ethyl-4-((1-(4-(p-tolyloxy)phenyl) ethyl)amino)-2,3-dihydro-1H-pyrrolo[3,4-c]pyridin-1-one To a solution of (S)-tert-butyl (2-ethyl-1-oxo-4-((1-(4-(p-tolyloxy)phenyl)ethyl) amino)-2,3-dihydro-1H-pyrrolo[3,4-c]pyridin-6-yl)carbamate (1.00 g, 1.99 mmol) in MeOH (15 mL) was added HCl/MeOH (4 M, 5.0 mL, 19.90 mmol). It was stirred at ambient temperature for 5 h. The solvent was concentrated in vacuo and the crude product was dissolved in DCM (50 mL), washed by sat. NaHCO$_3$ aqueous solution (30 mL) and brine (30 mL). The separated organic layer was dried over sodium sulfate, filtered and concentrated to give Compound 35 as a white solid (530 mg, yield 66.2%), which was further characterized by NMR and MS.

Synthetic Example 36

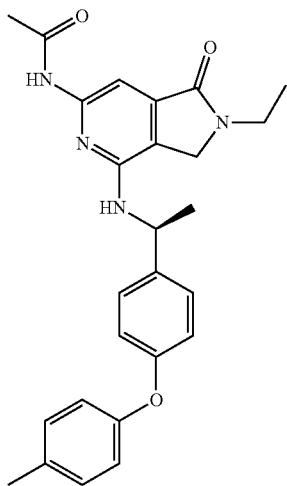 [SMILES: CCN1Cc2c(cc(NC(C)=O)nc2N[C@@H](C)c2ccc(Oc3ccc(C)cc3)cc2)C1=O]

(S)—N-(2-ethyl-1-oxo-4-((1-(4-(p-tolyloxy)phenyl) ethyl)amino)-2,3-dihydro-1H-pyrrolo[3,4-c]pyridin-6-yl)acetamide Starting with Compound 35, Compound 36 of the present disclosure was prepared according to Scheme 10.

To a solution of Compound 35 (200 mg, 0.50 mmol) in THF (10 mL) were added Ac$_2$O (76 mg, 0.75 mmol), TEA (101 mg, 0.99 mmol) and DMAP (6 mg, 0.05 mmol). After addition, it was stirred at ambient temperature for 5 h. TLC indicated that the reaction was completed. The solvent was removed by concentration in vacuo and residue was dissolved in DCM (20 mL), washed by water (10 mL×2) and brine (10 mL). The separated organic layer was concentrated and the crude product was purified by preparative TLC (DCM:MeOH=10:1) to give Compound 36 as a white solid (40 mg, yield 18%), which was further characterized by NMR and MS.

Synthetic Example 37

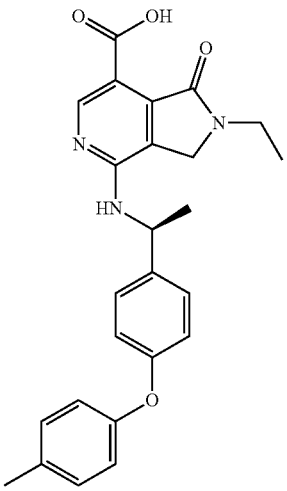 [SMILES: CCN1Cc2c(N[C@@H](C)c3ccc(Oc4ccc(C)cc4)cc3)ncc(C(=O)O)c2C1=O]

(S)-2-ethyl-1-oxo-4-((1-(4-(p-tolyloxy)phenyl)ethyl) amino)-2,3-dihydro-1H-pyrrolo[3,4-c]pyridine-7-carboxylic acid Compound 37 of the present disclosure was prepared according to Schemes 1, 2, 6 and 11.

Step 1

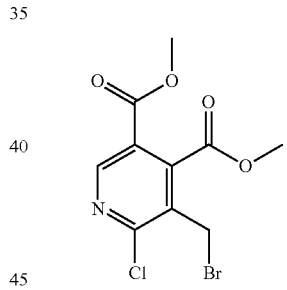

Dimethyl 5-(bromomethyl)-6-chloropyridine-3,4-dicarboxylate

To a solution of dimethyl 6-chloro-5-methylpyridine-3,4-dicarboxylate (5.00 g, 20.52 mmol) in CCl$_4$ (30 mL) was added NBS (4.02 g, 22.57 mmol) and BPO (249 mg, 1.03 mmol). After addition, the reaction mixture was heated to reflux for 3 h. TLC indicated that starting material was consumed. Then, it was cooled to ambient temperature and the resulting precipitate was removed by filtration, washed by CCl$_4$ (5 mL). The filtrate was concentrated in vacuo to give the crude product as a yellow solid, which was used in next step without further purification.

Step 2

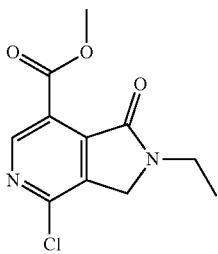 [SMILES: CCN1Cc2c(Cl)ncc(C(=O)OC)c2C1=O]

Methyl 4-chloro-2-ethyl-1-oxo-2,3-dihydro-1H-pyrrolo[3,4-c]pyridine-7-carboxylate The above crude product was dissolved in THF (150 mL). Ethanamine hydrochloride (1.67 g, 20.52 mmol) and $Cs_2CO_3$ (26.75 g, 82.09 mmol) were added into the reaction mixture. It was stirred at ambient temperature for 12 h. TLC indicated that starting material was consumed. The solid was removed by filtration, washed by ethyl acetate (10 mL) and the filtrate was concentrated in vacuo. The crude product was purified by silica gel column chromatography (eluted by Petroleum ether:Ethyl acetate=2:1) to give desired product as a light yellow solid (3.20 g, yield 61.2% in two steps).

Step 3

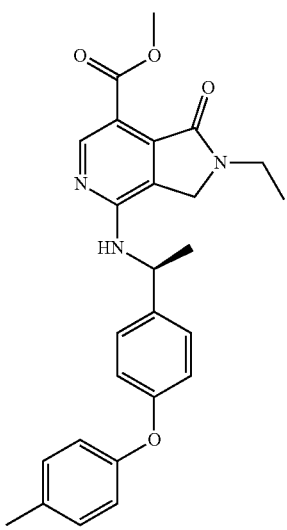 [SMILES: CCN1Cc2c(N[C@@H](C)c3ccc(Oc4ccc(C)cc4)cc3)ncc(C(=O)OC)c2C1=O]

(S)-methyl 2-ethyl-1-oxo-4-((1-(4-(p-tolyloxy)phenyl)ethyl)amino)-2,3-dihydro-1H-pyrrolo[3,4-c]pyridine-7-carboxylate To a solution of Methyl 4-chloro-2-ethyl-1-oxo-2,3-dihydro-1H-pyrrolo[3,4-c]pyridine-7-carboxylate (1.10 g, 4.32 mmol) in ethylene glycol (20 mL) was added (S)-1-(4-(p-tolyloxy)phenyl)ethanamine hydrochloride (1.71 g, 6.48 mmol) and TEA (874 mg, 8.64 mmol). The reaction mixture was heated to 150° C. and stirred for 5 h. It was cooled to ambient temperature and diluted with 50 mL water, extracted with ethyl acetate (80 mL×2). The combined organic layers were dried over sodium sulfate, filtered and concentrated. The crude product was purified by silica gel column chromatography (eluted by DCM MeOH=20:1) to give desired product as a white solid (1.20 g, yield 62.4%).

Step 4

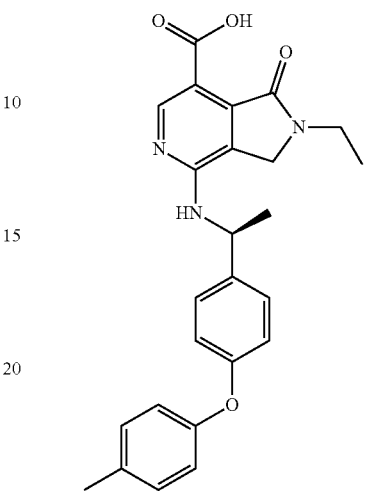

(S)-2-ethyl-1-oxo-4-((1-(4-(p-tolyloxy)phenyl)ethyl)amino)-2,3-dihydro-1H-pyrrolo[3,4-c]pyridine-7-carboxylic acid To a solution of (S)-methyl 2-ethyl-1-oxo-4-((1-(4-(p-tolyloxy)phenyl)ethyl) amino)-2,3-dihydro-1H-pyrrolo[3,4-c]pyridine-7-carboxylate (300 mg, 0.67 mmol) was dissolved in THF (15 mL) was added a solution of NaOH (54 mg, 1.35 mmol) in water (5 mL). After addition, it was stirred at ambient temperature for 5 h. TLC indicated that the reaction was completed. The organic solvent was removed by concentration in vacuo and the residue was diluted by water (10 mL), MTBE (8 mL) was added into the mixture and stirred for 10 min. Then the organic layer was removed by extraction, aqueous layer was acidified by addition of 2 N HCl aqueous solution to pH 7. The resulting precipitate was collected by filtration, washed by water (5 mL), dried in vacuo to give Compound 37 as a white solid (90 mg, yield 31.0%), which was further characterized by NMR and MS.

Biological Evaluation

Test 1: Purification of Wild-Type and Mutant IDH Proteins
Purification of IDH1 Proteins The present disclosure provides the method for purification of mutant and wild-type recombinant IDH1 protein in *E. coli*.

pSJ3 plasmids containing wild-type or mutant human IDH1 cDNA sequence are transformed into BL21 strains. A single colony is cultured in 5 ml LB medium at 37° C. overnight. The 5 ml start culture is expended in 2 L LB medium until the culture density reaches 0.5-0.6 OD600. Protein expression is induced by 0.5 mM IPTG at 20° C. overnight. The cells are collected by spinning and resuspend in TBS buffer (50 mM Tris pH7.5, 150 mM NaCl) supplemented with proteinase inhibitor PMSF. The cell lysate is prepared by sonication and is cleared by spinning. The supernatant is loaded into a column of Ni Separose 4B (purchased from GE Lifescience). The column is washed by 30 mM imidazole in TBS solution, and IDH protein is eluted by 300 mM imidazole in TBS solution. The imidazole is filtered out by Amicon 3,000 Da MWCO filter unit. Protein is stored at −80° C. in TBS solution contains 10% glycerol. The quantification of protein concentration is done by Bradford kit from Shanghai Sangon.

Purification of IDH2 Proteins

Due to its N-terminal mitochondrial targeting signal, IDH2 protein is insoluble and cannot be purified from *E. coli*. The present disclosure provides a novel method of expressing and purificating IDH2 proteins by utilizing baculovirus in insect cells. Using the same technique, the human IDH2 (R172K or R172S) mutant which is analogous to IDH1 (R132) mutant can also be expressed and purified.

Another method to purify the IDH2 proteins is to establish stable cells using human 293-F suspension cells to express wildtype and mutant IDH2, followed by affinity and ion-exchange purification.

Test 2: Metabolic Stability Assay in Liver Microsomes

The liver microsomes of mouse, rat, dog, monkey and human were purchased from Corning Inc., and were stored at −60° C. prior to use. The acetonitrile and NADPH were purchased from Honeywell International Inc. (New Jersey, U.S.) and Roche Inc. (Basel, Swiss). Midazolam was used as the positive control and was purchased from National Institutes for Food and Drug Control (Beijing, China).

Each of the test compounds or control compound Midazolam was co-incubated with 0.5 mg·mL$^{-1}$ (for test compound) or 0.2 mg·mL$^{-1}$ (for control) mouse, rat, dog, monkey or human liver microsomes in PBS (100 mM, pH 7.4) with 3 mM MgCl$_2$ in a 37° C. water bath at a pre-set initial concentration of 1 μM. Reactions were initiated by adding NADPH to a final concentration of 1 mM. The final volume of each reaction mixture was 0.2 ml, and all reactions were performed in duplicate. At each set time point (0, 5, 15, 30 and 60 min), a small aliquot (e.g., 20 μl) was transferred from the reaction system into ice-cold internal standard (IS) containing acetonitrile to quench the reaction and to precipitate the protein. After vortex and centrifuge at 3700 rpm for 10 min, the supernatant was injected into LC-MS/MS for analysis.

In vitro microsomal clearance was estimated based on determination of elimination half-life ($T_{1/2}$) of compounds disappearance from their initial concentrations. Peak area ratios of each compound (test or control) to IS was calculated. Ln (% Control) versus Incubation Time (min) curve was plotted, and the slope of a linear fitting line was calculated. Drug elimination rate constant k (min$^{-1}$), $T_{1/2}$ (min), and in vitro intrinsic clearance $CL_{int}$ (mL·min$^{-1}$·mg$^{-1}$ proteins) was calculated according to the following equations:

$$k = -\text{slope}$$

$$T_{1/2} = 0.693/k$$

$$CL_{int} = k/C_{protein}$$

where $C_{protein}$ (mg·mL$^{-1}$) is the microsomal protein concentration in the incubation system.

Test 3: Metabolic Stability Assay in Mouse Plasma

Blank male/female mouse plasma was provided by 3D BioOptima (Suzhou, China) and was freshly collected prior to use. The acetonitrile was purchased from Honeywell International Inc. (New Jersey, U.S.).

Each of the test compounds was co-incubated with mouse plasma in a 37° C. water bath at a pre-set initial concentration of 2 μM for 2 h and the final volume of each incubation mix was 0.3 mL. At each set time point (0, 15, 30, 60, 120 min), small aliquots from the plasma samples was transferred (each of 20 μL) into the mirocentrifuge tubes, then was added into 200 μL IS containing acetonitrile for protein precipitation. After vortex and centrifuge at 3700 rpm for 10 min, the supernatant was injected into LC-MS/MS for analysis. All incubations were performed in duplicate. In vitro compound stability was calculated by using the following equations:

$$\text{Stability} = \frac{C_t}{C_0} \times 100\%$$

where $C_t$ is the area ratio of the sample to the IS at 0.5, 1, 1.5 and 2 h post-incubation, and $C_0$ is the area ratio of the sample to the IS at 0 h pre-incubation.

Test 4: In Vivo Pharmacokinetics Assay

The pharmacokinetic properties of the compounds of the present disclosure were assessed in ICR mice (male, 6-8 weeks, 20.0-25.3 g) after p.o. and i.v. administration.

The ICR mice were purchased from Vital River Laboratory Technology Co., Ltd. (Beijing, China), housed in solid bottom polypropylene cages with sterilized bedding, kept in a room with 40% to 70% humidity, 20 to 25° C. room temperature, 10 to 20 air changes/hour, and on a 12-hour light/dark cycle except when interruptions are necessitated by study activities. The mice were fed with sterilized diet from Shanghai SLAC Laboratory Animal Co., Ltd. (Shanghai, China) and sterilized water. All animals were examined upon receipt and were acclimated for at least 3 days. Only the ones that appear to be healthy were selected for the study basing on overall health, body weight, or other relevant data as appropriate. Individual animal in each group was identified by ear notch.

The mice were fasted overnight prior to treatment, but having free access to drinking water all the time. Before dosing, each mouse was weighed and the actual dose volume for each mouse was calculated by using the formula below:

Dose Volume (mL) [Nominal Dose (mg·kg$^{-1}$)/Dose Concentration (mg·mL$^{-1}$)]×Animal Body Weight (kg)

The actual body weights and the actual dose volumes were recorded accordingly.

For each test group, nine mice were used, and mice in different groups were given a single p.o dose of the test compound at 10 mg·kg$^{-1}$, or a single i.v. dose of 2 mg·kg$^{-1}$ respectively. Blood samples (e.g., at least 120 μg) were collected into EDTA-K$_2$ tubes at pre-determined time points, for example, pre-dose, 5 min, 15 min, 30 min, 1 h, 2 h, 4 h, 8 h, 12 h, and 24 h post-dose. Each mouse was collected the blood sample at three discontinuous time points, and three mice were used for sampling at each time point. The collected samples were centrifuged at 5500 rpm for 10 min to obtain plasma samples, which were later measured by LC-MS/MS. Data of plasma concentration vs. time were processed by linear regression analysis. All pharmacokinetic parameters were calculated using non-compartment model of Pharsight Phoenix 6.3.

Test 5: Biochemical Assay for IDH Inhibition and Selectivity of the Compounds

The present disclosure provides a biochemical assay method for detecting the IDH inhibition and selectivity of the compounds by detecting IDH enzyme activity directly.

FIG. 1 shows reactions catalyzed by wild-type and mutant IDH1/2. Wild-type IDH enzyme could convert NADP$^+$ to NADPH when it catalyzes the α-KG producing reaction. Mutant IDH enzyme could convert NADPH to NADP$^+$ when it catalyzes the D-2-HG producing reaction. So the activity of wild-type and mutant IDH1/2 could be measured by monitoring NADPH level change: in the reaction catalyzed by wild-type IDH1/2, the newly generated NADPH is utilized instantly by coupled diaphorase-resazurin reaction to generate resorufin which is fluorescent (at Excitation 544 nm, Emission 590 nm) and thus NADPH is monitored indirectly; while in the reaction catalyzed by mutant IDH1/2, NADPH is directly monitored as it is fluorescent (at Excitation 340 nm, Emission 460 nm). By monitoring the change of NADPH level in the reaction, the enzyme activity could be determined rapidly and efficiently, $IC_{50}$ of a compound could also be assayed.

The test compounds were prepared into 50 mM stock solutions in DMSO and stored at −20° C. Each test compound stock was further diluted to obtain a 100× stock solution at a concentration of 200 μM, 100 μM, 50 μM, 25 μM, 12.5 juM, 6.25 μM and 3.125 μM, respectively, for the final use on the day of test.

Inhibition of Wild-Type IDH1:

Solution A was prepared by combining 1 M Tris-HCl pH7.5 (300 μL), 5 M NaCl (450 μL), 1 M $MgCl_2$ (150 μL), 1 M DTT (15 μL), 20 mg/mL BSA (37.5 μL), 50 mM NADP (20 μL), 80 mM isocitrate (20 μL), 100 mM resazurin (20 μL) and 0.1 unit/L diaphorase (50 μL), followed by adding deionized water to a final volume of 15 mL.

Reaction buffer was prepared by combining 1 M Tris-HCl pH7.5 (200 μL), 5 M NaCl (300 μL), 1 M $MgCl_2$ (100 μL), 1 M DTT (10 μL) and 20 mg/mL BSA (25 μL), followed by adding deionized water to a final volume of 10 mL.

Solution B was prepared by combining the reaction buffer (5 mL) and 107 μM wild-type IDH1 (0.37 μL).

148 μL Solution A was added into each sample well of a 96-well plate P1, and then 2 μL of the test compound solution at each concentration and 2 μL of DMSO (negative control/blank) were added into individual sample well respectively. 50 μL of Solution B was added into each of the sample wells having test compounds and one sample well having DMSO only, and 50 μL of reaction buffer was added into another sample well having DMSO only, respectively. P1 was put into BioTek Synergy H4 Microplate reader (BioTek Instruments Inc., Winooski, U.S.), and the program was set as follows: 37° C., shake plate 5 seconds, run kinetic mode, total detection time 20 min, detection intervals 40 seconds, detection mode fluorescence (at Excitation 544 nm, Emission 590 nm). The data were exported, the relative enzyme activity and the half-maximal inhibitory concentration ($IC_{50}$) for the test compound were calculated. Relative enzyme activity was calculated as the absolute value of the slope of the Emission 590 reads of each well plotted against time (which represents the production rate of NADPH catalyzed by wild-type IDH1). The Dose-response curve was drawn and the $IC_{50}$ was calculated via fitting. The IDH inhibition and selectivity of each test compound can be evaluated according to the effect of the compounds on the IDH enzyme activity.

Inhibition of Mutant IDHJ (R132H or R132C):

Solution A was prepared by combining 1 M Tris-HCl pH7.5 (300 μL), 5 M NaCl (450 μL), 1 M $MgCl_2$ (150 μL), 1 M DTT (15 μL), 20 mg/mL BSA (37.5 μL), 20 mM NADPH (20 μL), and 0.5 mM α-KG (40 μL), followed by adding deionized water to a final volume of 15 mL.

Reaction buffer was prepared by combining 1 M Tris-HCl pH 7.5 (200 μL), 5 M NaCl (300 μL), 1 M $MgCl_2$ (100 μL), 1 M DTT (10 μL) and 20 mg/mL BSA (25 μL), followed by adding deionized water to a final volume of 10 mL.

Solution B was prepared by combining the reaction buffer (5 mL) and 192 M IDH1-R132H (5.21 μL) or 107 μM IDH1-R132C (4.67 μL).

148 μL Solution A was added into each sample well of a 96-well plate P1, and then 2 μL of the test compound solution at each concentration and 2 μL of DMSO (negative control/blank) were added into individual sample well respectively. 50 μL of Solution B was added into each of the sample wells having test compounds and one sample well having DMSO only, and 50 μL of reaction buffer was added into another sample well having DMSO only, respectively. P1 was put into BioTek Synergy H4 Microplate reader (BioTek Instruments Inc., Winooski, U.S.), and the program was set as follows: 37° C., shake plate 5 seconds, run kinetic mode, total detection time 20 min, detection intervals 40 seconds, detection mode fluorescence (at Excitation 340 nm, Emission 460 nm). The data were exported, the relative enzyme activity and the half-maximal inhibitory concentration ($IC_{50}$) for the test compound were calculated. Relative enzyme activity was calculated as the absolute value of the slope of the Emission 460 reads of each well plotted against time (which represents the conversion rate of ca-KG to 2-HG through IDH1 modulated utilization of NADPH). The Dose-response curve was drawn and the $IC_{50}$ was calculated via fitting. The IDH inhibition and selectivity of each test compound can be evaluated according to the effect of the compounds on the IDH enzyme activity.

Test 6: Cell-Based Assay for IDH Inhibition and Selectivity of the Compounds

The present disclosure also provides a cell based method for assaying IDH inhibition and selectivity of the compounds in human fibrosacoma cell line HT1080 and cholangiocarcinoma cell line HCCC 9810, which harbor endogenous heterozygous IDH1 R132C and R132H mutation respectively and accumulate D-2-HG Tumor derived IDH mutant lost its normal activity of producing α-KG and gained a new activity of producing D-2-HG D-2-HG is a metabolite specifically elevated in IDH mutated tumor samples. Its concentration in normal tissues is negligible, and it does not have any known physiological functions in normal tissue. Because the mutant IDH1 and IDH2 gain a new catalytic activity that does not have a function in normal cells, inhibitors of mutant IDH enzyme therefore will effectively inhibit the growth of tumor cells expressing mutant IDH, but not affect the growth of normal cells. Hence, the method can be used for screening compounds which have high specificity to cells with mutant IDH and low toxicity to normal cells.

By treating HT1080 and HCCC 9810 cells with an effective IDH inhibitor, the synthesis of D-2-HG is blocked, and D-2-HG concentration is decreased by the oxidation reaction catalyzed by D-2-HG dehydrogenase. Hence, the IDH inhibition activity and selectivity of the compounds of present disclosure could be assayed by the decrease of D-2-HG in cell metabolite.

To perform a cell based IDH inhibitor assay, HT1080 and HCCC 9810 cells (or other cell lines harboring different IDH mutations) are cultured in DMEM supplemented with 10% FBS. The cells are treated with compounds of present disclosure at various different concentration. At various time points (between 4-24 hours) after the treatment, cell culture supernatants were removed and cells were washed with PBS for one or two times. Cell metabolites are extracted by adding 80% methanol (pre-chilled under −80° C.) in the cells, extract at 4° C. temperature for 60 min, centrifuged to remove any insoluble component. Metabolites (clear supernatant from the previous step) are lyophilized and reconstituted in pyridine containing 20 mg/ml O-methoxyamineHCl and are incubated at 70° C. for 40 minutes. After cooling down to room temperature, MTBSTFA (N-tert-Butyldimethylsilyl-N-methyltrifluoroacetamide, Sigma Aldrich) is added at a volume ratio of 4:7 (e.g., 20 μL MTBSTFA to 35 μL 20 mg/ml O-methoxyamineHCl solution) and derivation is performed at 70° C. for 30 minutes. The derived metabolites including D-2-HG are analyzed by Agilent 7890A-5750 GC/MS system. 1 l of the derived metabolite is injected into Agilent 7890A-5750 for D-2-HG concentration analysis. GC oven temperature is programmed from 140° C. to 260° C. at 10° C./min, from 260° C. to 310° C. at 8° C./min and hold at 310° C. for 5 min. The flow rate of carrier gas is 1 ml/min. The mass spectrometer is operated in the electron impact (EI) mode at 70 eV D-2-HG is normalized to endogenous glutamate.

The activity of IDHs in the presence of each compounds at different concentrations can be represented by relative D-2-HG concentration to negative control samples, and the $IC_{50}$ value, the inhibition and selectivity for each compound can be evaluated.

Test 7: Improved Cell-Based Assay for IDH Inhibition and Selectivity of the Compounds The present disclosure also provides an improved cell-based assay for IDH inhibition and selectivity of the compounds, which involves stably over-expressing D-2-HG dehydrogenase in HT1080 and HCCC 9810 cells.

Figure 2A:
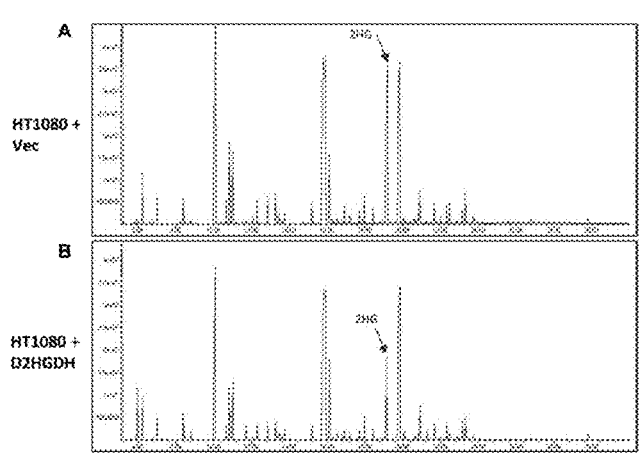
FIG. 2A shows that the intracellular level of 2-HG in parental HT1080 cells and stable HT1080 overexpressing Flag-tagged D-2-HG DH was determined by GC-MS analysis (modified from "'D-2-hydroxyglutarate is essential for maintaining oncogenic property of mutant IDH-containing cancer cells but dispensable for cell growth', Ma, S., et al., Oncotarget, (2015)").
Figure 2B:
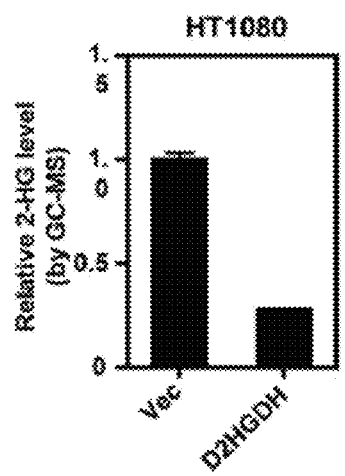
FIG. 2B shows that 2-HG peak was further confirmed by D-2-HG standard, the quantification was done using the main fragment m/z 433.

According to previous report, over expression of D-2-HG dehydrogenase decreases the half-life of D-2-HG in HT1080 cells (FIGS. 2A and 2B) ["D-2-hydroxyglutarate is essential for maintaining oncogenic property of mutant IDH-containing cancer cells but dispensable for cell growth", Ma, S., et al., Oncotarget, (2015)], making the cells more sensitive to D-2-HG synthesis blockage by mutant IDH1 inhibitors. It will greatly increase the sensitivity and accurateness of this cell based assay. In the improved cell-based assay, all other steps are performed as disclosed in Test 6.

Test 8: Inhibition of Anchorage Independent Growth of IDH Mutant Cells

It is well established that anchorage-independent cell growth is a fundamental property of cancer cells. The ability of anchorage independent growth tightly correlates with tumorigenic and metastatic potentials of tumor cells in vivo.

Previous work has shown that deletion of the mutant IDH1 in HT1080 has little effect on cell proliferation in normal culture condition, but strongly inhibits the anchorage independent growth of the HT1080 cell line, which has the IDH1H132C mutation ["D-2-hydroxyglutarate is essential for maintaining oncogenic property of mutant IDH-containing cancer cells but dispensable for cell growth", Ma, S., et al., Oncotarget, (2015)]. Deletion of the mutant IDH1 also abolishes D-2-HG production in the HT1080 cells. In present disclosure, anchorage independent growth (formation of colonies in soft agar) is also used as a convenient and valuable in vitro assay for measuring the activity of compounds in tumor inhibition.

The compounds of present disclosure are used to treat IDH-mutant cancer cell lines, such as HT1080 containing IDH1 R132C and HCCC9810 containing IDH1 R132H, and test whether the compounds would affect cell growth in soft agar. The compounds are added into the soft agar as well as in the medium above the soft agar at a concentration higher than the $IC_{50}$ value calculated from the results in Test 5 and 6 for each compound. Colony formation is visualized by microscope. At the end of the experiments, the soft agar plates are stained with crystal violet to visualize cell colonies for quantification. The demonstration of IDH1 inhibition suppressing anchorage independent growth in a soft agar assay provides a valuable, effective, and convenient assay for assaying the activity of mutant IDH inhibitors in tumor inhibition. This assay is particularly informative as inhibition of mutant IDH1 does not affect HT 1080 cell growth under normal culture condition.

Test 9: Inhibition of the IDH Mutant Tumor Growth in Patient Derived Xenograft Model Previous work has shown that inhibition of mutant IDH R132C could suppress the tumor growth of the HT1080 by xenograft experiments ["D-2-hydroxyglutarate is essential for maintaining oncogenic property of mutant IDH-containing cancer cells but dispensable for cell growth", Ma, S., et al., Oncotarget, (2015)]. Patient derived xenograft mouse (PDX) model is used herein as a convenient and valuable in vivo assay for measuring the activity of compounds in tumor inhibition. As an initial experiment, an IDH1 mutant glioma PDX model has been established from the Bt142 glioma brain stem cell line, which has IDH1 R132H mutation ["An in vivo patient-derived model of endogenous IDH1-mutant glioma", Luchman, H. A., et al., Neuro Oncol, (2012)]. This mouse model is used to test the efficacy of compounds of present disclosure in suppressing glioma with IDH1 R132H mutation. The compounds of present disclosure inhibit the growth of the tumors harboring IDH1 R132H mutation in the xenograft models.

Working Examples

Figure 3:
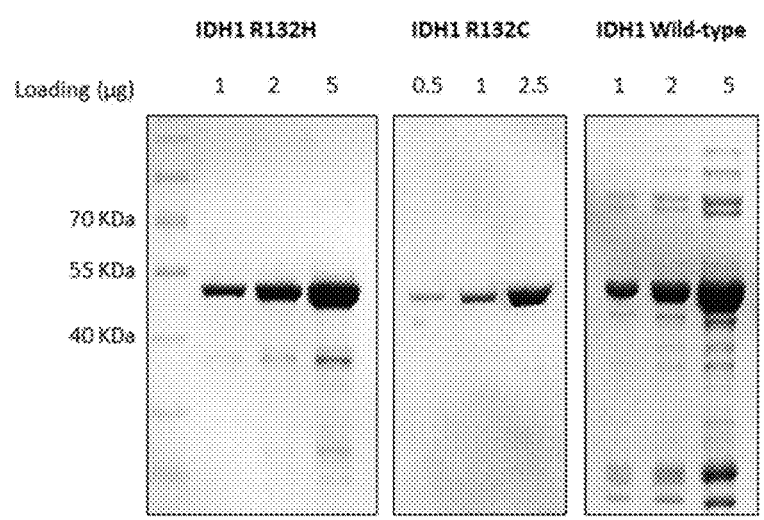
FIG. 3 shows the coomassie staining for each of IDH1-R132H, IDH1-R132C, and IDH1-WT proteins.
Figure 4A:
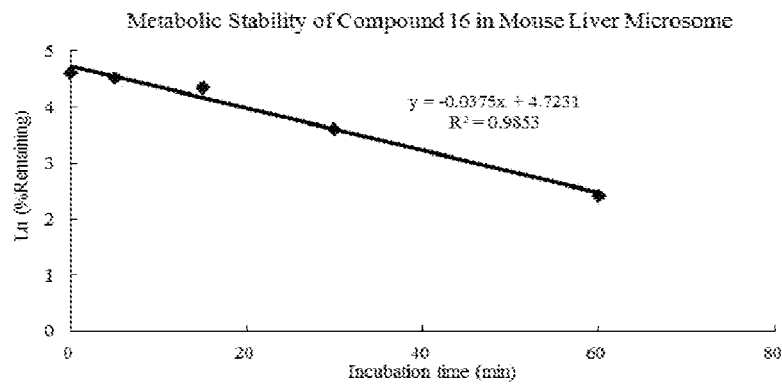
FIG. 4A shows the natural logarithm of the percentage (%) remaining of the substrate (an exemplary compound of the present disclosure) (i.e. Ln (% remaining)) of an exemplary compound of the present disclosure as a function of incubation time in liver microsome of mouse.
Figure 4B:
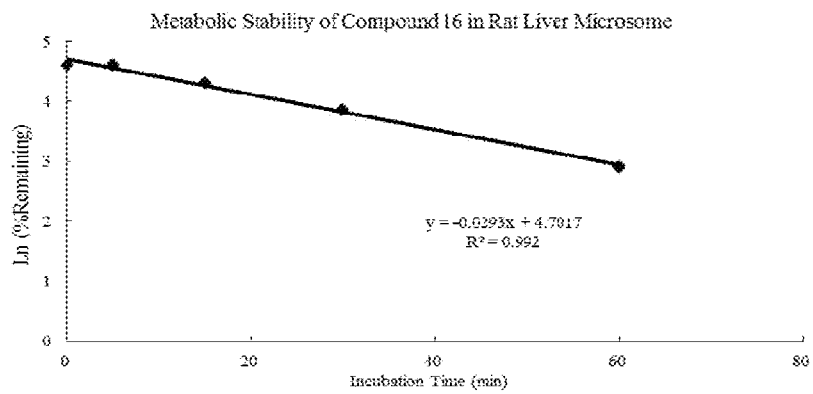
FIG. 4B shows the Ln (% remaining) of an exemplary compound of the present disclosure as a function of incubation time in liver microsome of rat.
Figure 4C:
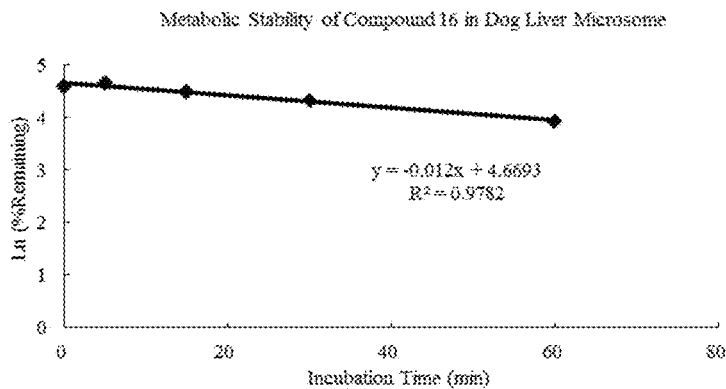
FIG. 4C shows the Ln (% remaining) of an exemplary compound of the present disclosure as a function of incubation time in liver microsome of dog.
Figure 4D:
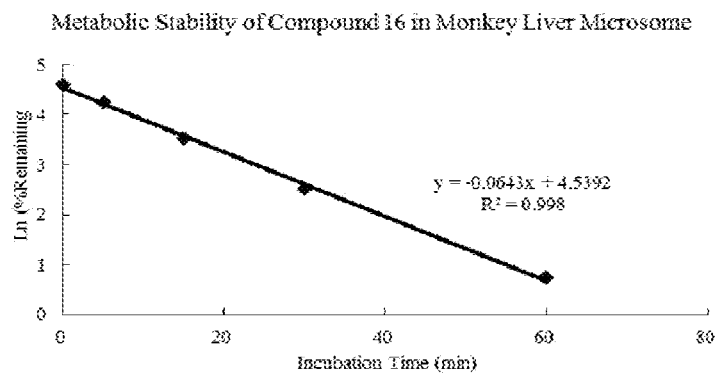
FIG. 4D shows the Ln (% remaining) of an exemplary compound of the present disclosure as a function of incubation time in liver microsome of monkey.
Figure 4E:
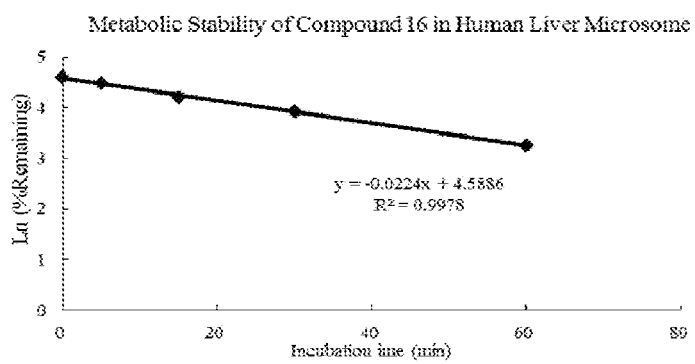
FIG. 4E shows the Ln (% remaining) of an exemplary compound of the present disclosure as a function of incubation time in liver microsome of human.

Example 1: Purification of IDH1 WT/R132H/R132C Proteins pSJ3-IDH1-R132H, pSJ3-IDH1-R132C, and pSJ3-IDH1-WT plasmids were transformed into BL21 strains respectively. IDH1 WT/R132H/R132C proteins were induced and purified in accordance with the methods disclosed in Test 1 of the Biological evaluation section. The concentration for each purified proteins was determined by Bradford assay. FIG. 3 shows the coomassie staining for each of IDH1-R132H, IDH1-R132C, and IDH1-WT proteins, which proves the successful expression and purification of the proteins.

Example 2: In Vitro Metabolic Stability Studies 2.1 Metabolic Stability in Liver Microsomes In this study, the metabolic stability of the compounds was assessed in mouse, rat, dog, monkey and human liver microsome according to the method disclosed in Test 2 of the Biological evaluation section. Midazolam was used as the positive control.

Each experiment was independently performed in duplicate (indicated as #1 and #2 respectively), and the data obtained for an exemplary Compound 16 are shown in Tables 1-5 and FIGS. 4A-4E. A summary of the metabolic stability results of Compound 16 compared with the results of the positive control is shown in Table 6. All results shown in Table 6 are mean values of the results from the two independent experiments.

TABLE 1

Metabolic stability of Compound 16 in mouse liver microsome

| Incubation time (min) | Peak area ratio #1 | Peak area ratio #2 | Mean peak area ratio | % remaining #1 | % remaining #2 | Ln (% remaining) #1 | Ln (% remaining) #2 | Mean Ln(% remaining) |
|---|---|---|---|---|---|---|---|---|
| 0 | 1.94 | 1.72 | 1.83 | 100 | 100 | 4.61 | 4.61 | 4.61 |
| 5 | 1.71 | 1.62 | 1.67 | 88.1 | 94.2 | 4.48 | 4.55 | 4.51 |
| 15 | 1.41 | 1.39 | 1.40 | 72.7 | 80.8 | 4.29 | 4.39 | 4.34 |
| 30 | 0.601 | 0.753 | 0.677 | 31.0 | 43.8 | 3.43 | 3.78 | 3.61 |
| 60 | 0.206 | 0.206 | 0.206 | 10.6 | 12.0 | 2.36 | 2.48 | 2.42 |

| | K ($min^{-1}$) | $T_{1/2}$ (min) | $CL_{int}$ ($\mu L \cdot min^{-1} \cdot mg^{-1}$) |
|---|---|---|---|
| #1 | 0.0387 | 17.9 | 77.4 |
| #2 | 0.0364 | 19.1 | 72.7 |
| Mean | 0.0375 | 18.5 | 75.1 |

TABLE 2

Metabolic stability of Compound 16 in rat liver microsome

| Incubation time (min) | Peak area ratio #1 | Peak area ratio #2 | Mean peak area ratio | % remaining #1 | % remaining #2 | Ln (% remaining) #1 | Ln (% remaining) #2 | Mean Ln(% remaining) |
|---|---|---|---|---|---|---|---|---|
| 0 | 1.80 | 1.17 | 1.49 | 100 | 100 | 4.61 | 4.61 | 4.61 |
| 5 | 1.62 | 1.30 | 1.46 | 90.0 | 111 | 4.50 | 4.71 | 4.61 |
| 15 | 1.07 | 1.08 | 1.08 | 59.4 | 92.3 | 4.09 | 4.53 | 4.31 |
| 30 | 0.645 | 0.736 | 0.691 | 35.8 | 62.9 | 3.58 | 4.14 | 3.86 |
| 60 | 0.252 | 0.282 | 0.267 | 14.0 | 24.1 | 2.64 | 3.18 | 2.91 |

| | K ($min^{-1}$) | $T_{1/2}$ (min) | $CL_{int}$ ($\mu L \cdot min^{-1} \cdot mg^{-1}$) |
|---|---|---|---|
| #1 | 0.0333 | 20.8 | 66.5 |
| #2 | 0.0253 | 27.4 | 50.7 |
| Mean | 0.0293 | 24.1 | 58.6 |

TABLE 3

Metabolic stability of Compound 16 in dog liver microsome

| Incubation time (min) | Peak area ratio #1 | Peak area ratio #2 | Mean peak area ratio | % remaining #1 | % remaining #2 | Ln (% remaining) #1 | Ln (% remaining) #2 | Mean Ln(% remaining) |
|---|---|---|---|---|---|---|---|---|
| 0 | 1.66 | 1.92 | 1.79 | 100 | 100 | 4.61 | 4.61 | 4.61 |
| 5 | 1.74 | 2.03 | 1.89 | 105 | 106 | 4.65 | 4.66 | 4.66 |
| 15 | 1.57 | 1.64 | 1.61 | 94.6 | 85.4 | 4.55 | 4.45 | 4.50 |
| 30 | 1.27 | 1.46 | 1.37 | 76.5 | 76.0 | 4.34 | 4.33 | 4.33 |
| 60 | 0.877 | 0.936 | 0.907 | 52.8 | 48.8 | 3.97 | 3.89 | 3.93 |

| | K ($min^{-1}$) | $T_{1/2}$ (min) | $CL_{int}$ ($\mu L \cdot min^{-1} \cdot mg^{-1}$) |
|---|---|---|---|
| #1 | 0.0115 | 60.3 | 23.0 |
| #2 | 0.0126 | 55.0 | 25.2 |
| Mean | 0.0120 | 57.6 | 24.1 |

TABLE 4

Metabolic stability of Compound 16 in monkey liver microsome

| Incubation time (min) | Peak area ratio #1 | Peak area ratio #2 | Mean peak area ratio | % remaining #1 | % remaining #2 | Ln (% remaining) #1 | Ln (% remaining) #2 | Mean Ln(% remaining) |
|---|---|---|---|---|---|---|---|---|
| 0 | 1.89 | 1.87 | 1.88 | 100 | 100 | 4.61 | 4.61 | 4.61 |
| 5 | 1.25 | 1.36 | 1.31 | 66.1 | 72.7 | 4.19 | 4.29 | 4.24 |
| 15 | 0.614 | 0.662 | 0.638 | 32.5 | 35.4 | 3.48 | 3.57 | 3.52 |
| 30 | 0.237 | 0.229 | 0.233 | 12.5 | 12.2 | 2.53 | 2.51 | 2.52 |
| 60 | 0.0403 | 0.0386 | 0.0395 | 2.13 | 2.06 | 0.757 | 0.725 | 0.741 |

| | K (min$^{-1}$) | $T_{1/2}$ (min) | $CL_{int}$ ($\mu L \cdot min^{-1} \cdot mg^{-1}$) |
|---|---|---|---|
| #1 | 0.0635 | 10.9 | 127 |
| #2 | 0.0651 | 10.7 | 130 |
| Mean | 0.0643 | 10.8 | 129 |

TABLE 5

Metabolic stability of Compound 16 in human liver microsome

| Incubation time (min) | Peak area ratio #1 | Peak area ratio #2 | Mean peak area ratio | % remaining #1 | % remaining #2 | Ln (% remaining) #1 | Ln (% remaining) #2 | Mean Ln(% remaining) |
|---|---|---|---|---|---|---|---|---|
| 0 | 2.01 | 2.00 | 2.01 | 100 | 100 | 4.61 | 4.61 | 4.61 |
| 5 | 1.75 | 1.81 | 1.78 | 87.1 | 90.5 | 4.47 | 4.51 | 4.49 |
| 15 | 1.32 | 1.38 | 1.35 | 65.7 | 69.0 | 4.18 | 4.23 | 4.21 |
| 30 | 1.04 | 1.01 | 1.03 | 51.7 | 50.5 | 3.95 | 3.92 | 3.93 |
| 60 | 0.527 | 0.507 | 0.517 | 26.2 | 25.4 | 3.27 | 3.23 | 3.25 |

| | K (min$^{-1}$) | $T_{1/2}$ (min) | $CL_{int}$ ($\mu L \cdot min^{-1} \cdot mg^{-1}$) |
|---|---|---|---|
| #1 | 0.0218 | 31.8 | 43.6 |
| #2 | 0.0229 | 30.3 | 45.8 |
| Mean | 0.0224 | 31.0 | 44.7 |

TABLE 6

Summary of Metabolic Stability results of Compound 16 compared with the results of positive control in liver microsome from different species

| Sample | Species | k (min$^{-1}$) | $T_{1/2}$ (min) | $CL_{int}$ ($\mu L \cdot min^{-1} \cdot mg^{-1}$) |
|---|---|---|---|---|
| Compound 16 | Mouse | 0.0375 | 18.5 | 75.1 |
| | Rat | 0.0293 | 24.1 | 58.6 |
| | Dog | 0.0120 | 57.6 | 24.1 |
| | Monkey | 0.0643 | 10.8 | 129 |
| | Human | 0.0224 | 31.0 | 44.7 |
| Positive control | Mouse | 0.0964 | 7.19 | 482 |
| | Rat | 0.174 | 3.98 | 871 |
| | Dog | 0.140 | 4.94 | 702 |
| | Monkey | 0.211 | 3.29 | 1053 |
| | Human | 0.0612 | 11.3 | 306 |

The results show that Compound 16 exhibits different metabolic stability in liver microsome of different species, with in vitro clearance from fast to slow as: monkey, mouse, rat, human and dog (i.e., monkey>mouse>rat>human>dog). Compared with the positive control Midazolam, the clearance of Compound 16 in human liver microsome is slow, indicating that Compound 16 has medium stability in human liver microsome.

2.2 Metabolic Stability in Plasma

In this study, the metabolic stability of the compounds in mouse plasma was assessed according to the method disclosed in Test 3 of the Biological evaluation section.

Figure 5:
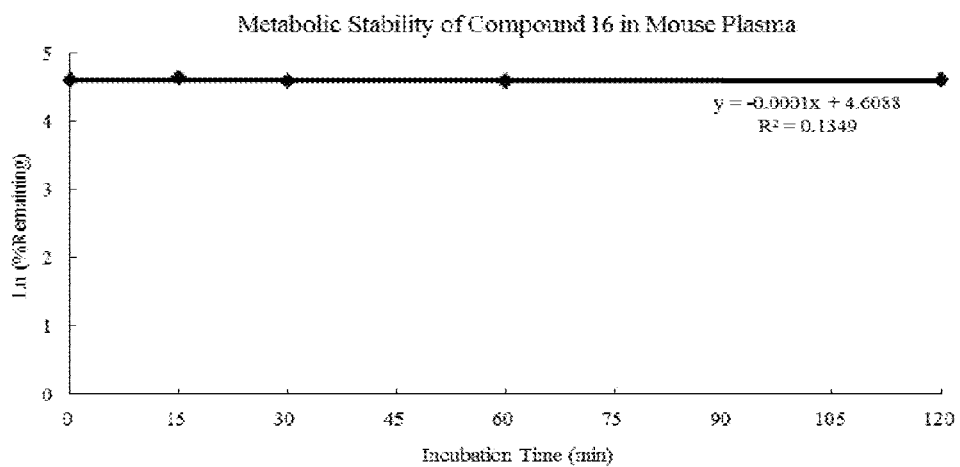
FIG. 5 shows the Ln (% remaining) of an exemplary compound of the present disclosure as a function of incubation time in mouse plasma.

Each experiment was independently performed in duplicate (indicated as #1 and #2 respectively). The results obtained for an exemplary Compound 16 are shown in Table 7 and FIG. 5.

TABLE 7

Metabolic stability of Compound 16 in mouse plasma

| Incubation time (min) | Peak area ratio #1 | Peak area ratio #2 | Mean peak area ratio | % remaining #1 | % remaining #2 | Ln (% remaining) #1 | Ln (% remaining) #2 | Mean Ln(% remaining) |
|---|---|---|---|---|---|---|---|---|
| 0 | 4.38 | 4.54 | 4.46 | 100 | 100 | 4.61 | 4.61 | 4.61 |
| 15 | 4.37 | 4.79 | 4.58 | 99.8 | 106 | 4.60 | 4.66 | 4.63 |
| 30 | 4.16 | 4.62 | 4.39 | 95.0 | 102 | 4.55 | 4.62 | 4.59 |
| 60 | 4.31 | 4.49 | 4.40 | 98.4 | 98.9 | 4.59 | 4.59 | 4.59 |
| 120 | 4.60 | 4.27 | 4.44 | 105 | 94.1 | 4.65 | 4.54 | 4.60 |

| | K ($min^{-1}$) | $T_{1/2}$ (min) |
|---|---|---|
| #1 | NA | NA |
| #2 | 0.000737 | 940 |
| Mean | 0.000737 | 940 |

The results show that the average percentage remaining of Compound 16 is above 98.5% within the 2 hrs period, indicating that Compound 16 remains stable in mouse plasma for at least 2 hrs period.

Example 3: In Vivo Pharmacokinetics Studies

The pharmacokinetics (PK) studies of the compounds were conducted in ICR mice (male, 6-8 weeks, 20.0-25.3 g, Vital River Laboratory Technology Co., Ltd.) administrated a single p.o. dose of 10 mg·$kg^{-1}$ or a single i.v. dose of 2 mg·$kg^{-1}$ according to the method disclosed in Test 4 of the Biological evaluation section.

Figure 6:
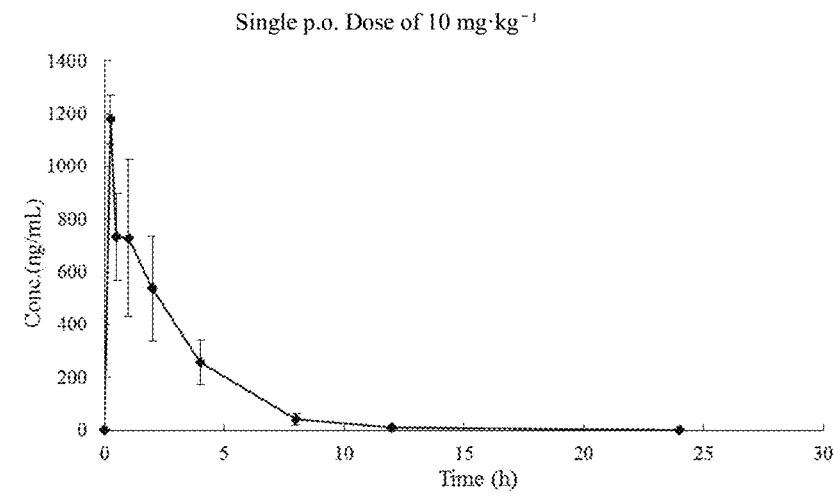
FIG. 6 shows the mean plasma concentration as a function of time after administered a single p.o. dose of 10 mg·kg$^{-1}$ of an exemplary compound of the present disclosure to ICR mouse.
Figure 7:
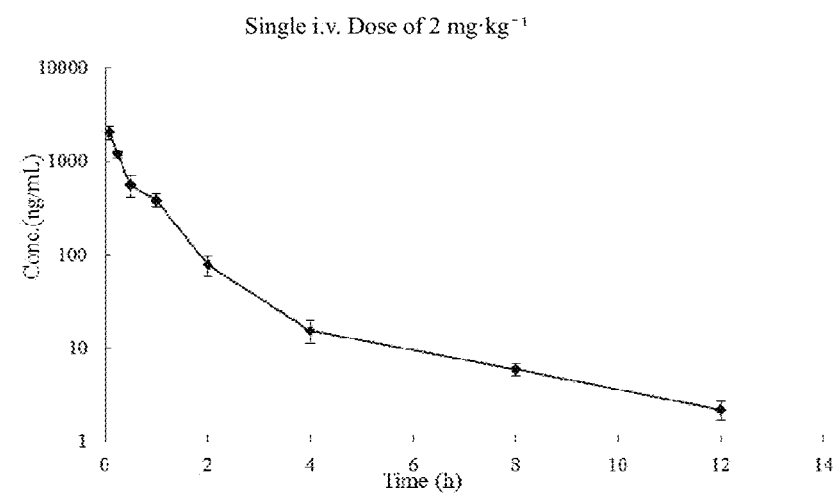
FIG. 7 shows the mean plasma concentration as a function of time after administering a single i.v. dose of 2 mg·kg$^{-1}$ of an exemplary compound of the present disclosure to ICR mouse.
Figure 8A:
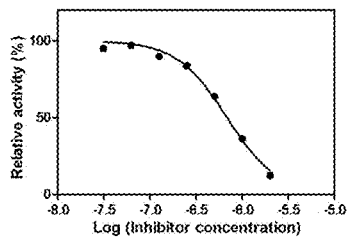
FIG. 8A-C shows the enzyme activity of IDH1 R132H plotted as a function of logarithm of the concentration of Compound 16 tested in triplet.
Figure 8B:
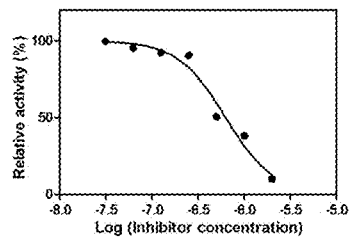
Figure 8C:
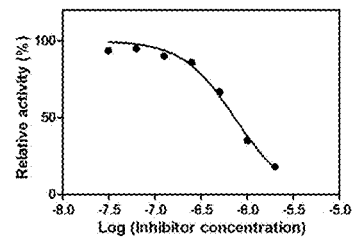
Figure 9A:
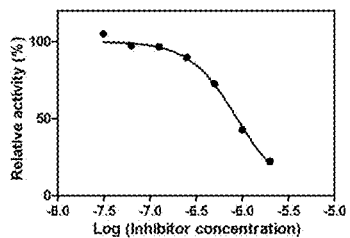
FIG. 9A-C shows the enzyme activity of IDH1 R132H plotted as a function of logarithm of the concentration of Compound 21 tested in triplet.
Figure 9B:
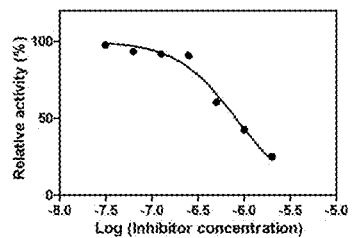
Figure 9C:
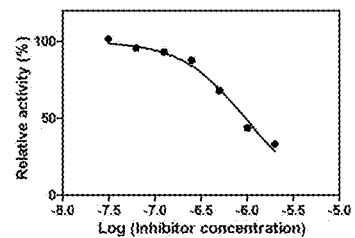
Figure 10A:
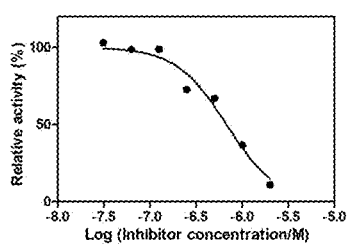
FIG. 10A-C shows the enzyme activity of IDH1 R132H plotted as a function of logarithm of the concentration of Compound 22 tested in triplet.
Figure 10B:
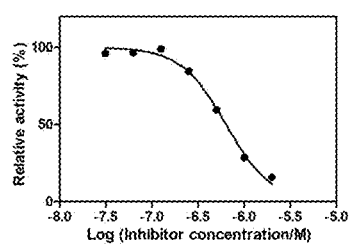
Figure 10C:
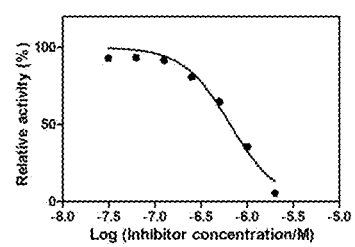
Figure 11A:
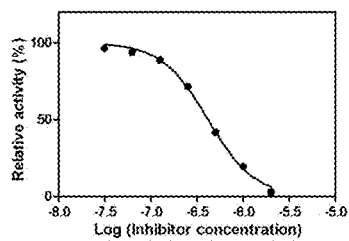
FIG. 11A-C shows the enzyme activity of IDH1 R132H plotted as a function of logarithm of the concentration of Compound 23 tested in triplet.
Figure 11B:
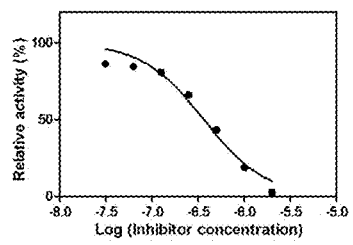
Figure 11C:
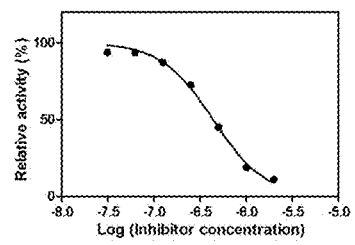
Figure 12A:
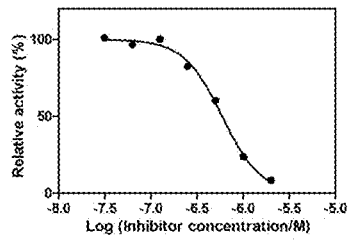
FIG. 12A-C shows the enzyme activity of IDH1 R132H plotted as a function of logarithm of the concentration of Compound 24 tested in triplet.
Figure 12B:
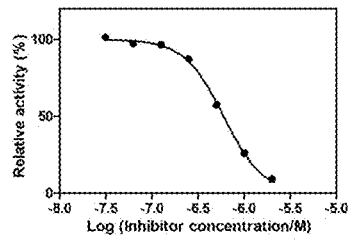
Figure 12C:
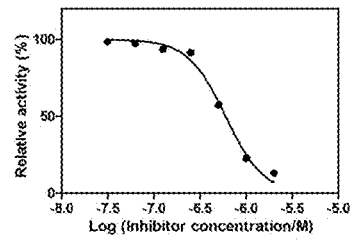
Figure 13A:
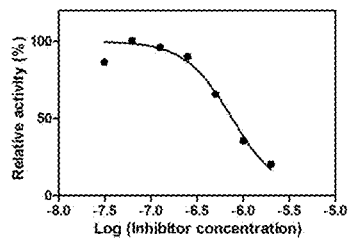
FIG. 13A-C shows the enzyme activity of IDH1 R132H plotted as a function of logarithm of the concentration of Compound 31 tested in triplet.
Figure 13B:
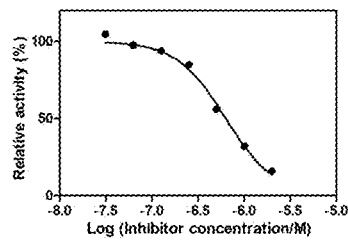
Figure 13C:
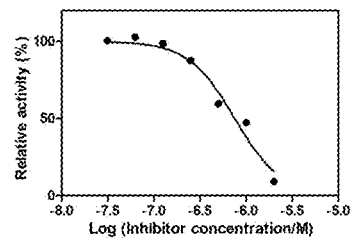
Figure 14A:
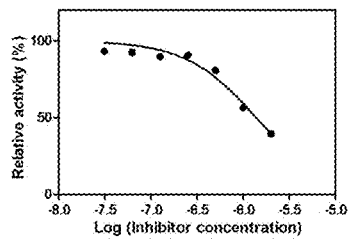
FIG. 14A-C shows the enzyme activity of IDH1 R132C plotted as a function of logarithm of the concentration of Compound 16 tested in triplet.
Figure 14B:
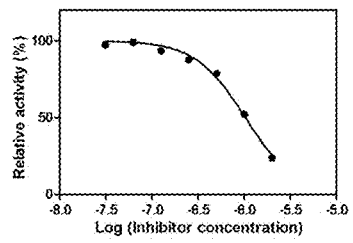
Figure 14C:
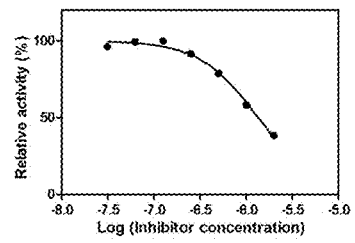
Figure 15A:
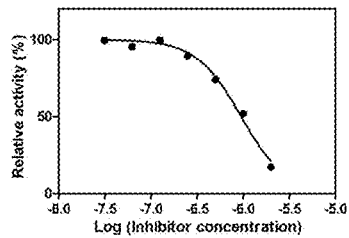
FIG. 15A-C shows the enzyme activity of IDH1 R132C plotted as a function of logarithm of the concentration of Compound 21 tested in triplet.
Figure 15B:
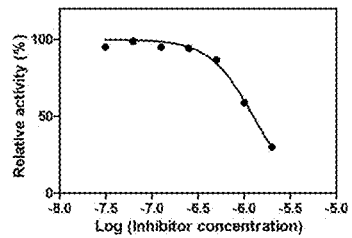
Figure 15C:
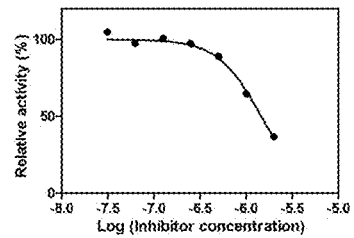
Figure 16A:
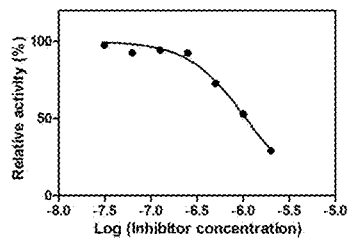
FIG. 16A-C shows the enzyme activity of IDH1 R132C plotted as a function of logarithm of the concentration of Compound 22 tested in triplet.
Figure 16B:
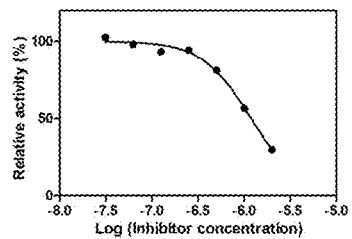
Figure 16C:
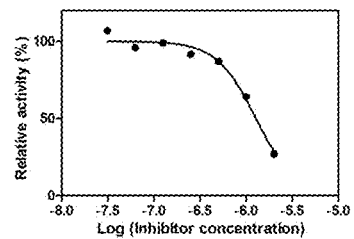
Figure 17A:
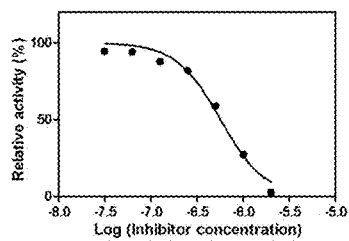
FIG. 17A-C shows the enzyme activity of IDH1 R132C plotted as a function of logarithm of the concentration of Compound 23 tested in triplet.
Figure 17B:
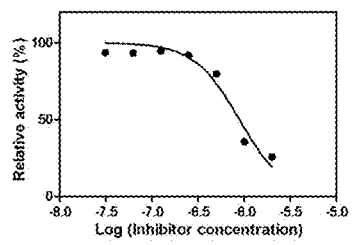
Figure 17C:
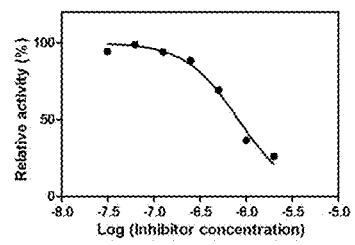
Figure 18A:
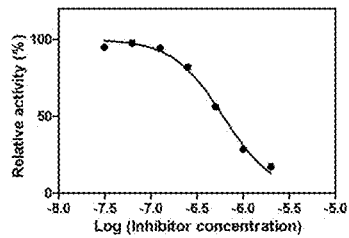
FIG. 18A-C shows the enzyme activity of IDH1 R132C plotted as a function of logarithm of the concentration of Compound 24 tested in triplet.
Figure 18B:
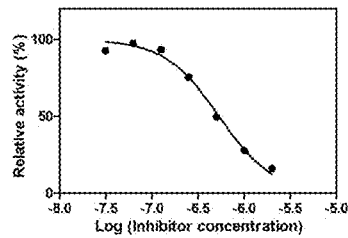
Figure 18C:
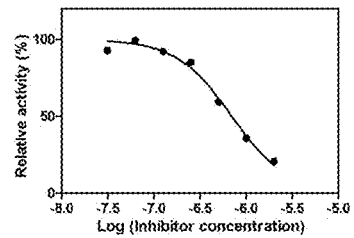
Figure 19A:
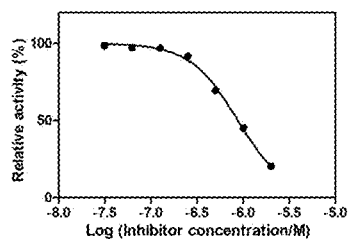
FIG. 19A-C shows the enzyme activity of IDH1 R132C plotted as a function of logarithm of the concentration of Compound 31 tested in triplet.
Figure 19B:
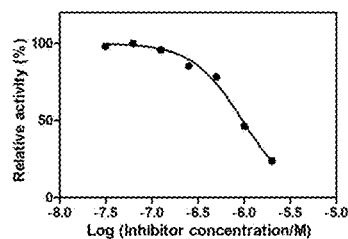
Figure 19C:
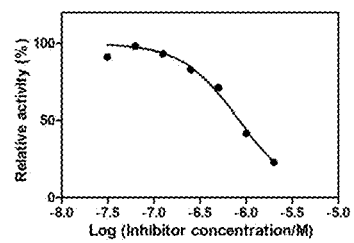

Each experiment was independently performed in triplicate. The plasma concentration of an exemplary Compound 23 after a p.o. administration of 10 mg·$kg^{-1}$ in ICR mouse is plotted as function of time in FIG. 6. The plasma concentration of the exemplary Compound 23 after an i.v. injection of 2 mg·$kg^{-1}$ in ICR mouse is plotted as function of time in FIG. 7. Each data represents the mean plasma concentration of the three experiments with standard error of mean (SEM) as error bars.

The PK parameters of Compound 23 are shown in Table 8A and 8B for p.o. and i.v. administrations, respectively.

TABLE 8A

The PK parameters of Compound 23 for p.o. administration in ICR mouse

| PK Parameters | p.o. dose of 10 mg · $kg^{-1}$ |
|---|---|
| $C_{max}$ (ng · $mL^{-1}$) | 1178 |
| $T_{max}$ (h) | 0.25 |
| $K_{el}$ ($h^{-1}$) | 0.385 |
| $T_{1/2}$ (h) | 1.8 |
| $AUC_{0-t}$ (ng · h · $mL^{-1}$) | 2886 |
| $AUC_{0-inf}$ (ng · h · $mL^{1}$) | 2917 |
| $AUMC_{0-t}$ (ng · $h^2$ · $mL^{-1}$) | 7099 |
| $AUMC_{0-inf}$ (ng · $h^2$ · $mL^{-1}$) | 7550 |
| $MRT_{PO}$ (h) | 2.6 |
| F (%) | 44 |

TABLE 8B

The PK parameters of Compound 23 for i.v. administration in ICR mouse

| PK Parameters | i.v. dose of 2 mg · $kg^{-1}$ |
|---|---|
| $K_{el}$ ($h^{-1}$) | 0.244 |
| $T_{1/2}$ (h) | 2.8 |
| $AUC_{0-t}$ (ng · h · $mL^{-1}$) | 1302 |
| $AUC_{0-inf}$ (ng · h · $mL^{-1}$) | 1311 |
| $AUMC_{0-t}$ (ng · $h^2$ · $mL^{-1}$) | 1138 |
| $AUMC_{0-inf}$ (ng · $h^2$ · $mL^{-1}$) | 1283 |
| $MRT_{IV}$ (h) | 0.98 |
| CL (mL · $kg^{-1}$ · $min^{-1}$) | 25.4 |
| $Vd_{ss}$ (L · $kg^{-1}$) | 1.49 |

Example 4: Compounds Inhibit the Activity of IDH1 R132H and IDH1 R132C

The IDH inhibition activity of the compounds were assessed according to Test 5 of the Biological evaluation section. The test for mutant IDH1 R132H/R132C inhibition of each compound was carried out in triplet. For IDH1 R132H, the enzyme activity of exemplary Compounds 16, 21, 22, 23, 24 and 31 is plotted as a function of logarithm of the concentration of the compound in FIGS. 8A-8C, 9A-9C, 10A-10C, 11A-11C, 12A-12C and 13A-13C, respectively. The $IC_{50}$ values of Compounds 16, 21, 22, 23, 24 and 31 to IDH1 R132H are less than 1.0 µM. For IDH1 R132C, the enzyme activity of exemplary Compounds 16, 21, 22, 23, 24 and 31 is plotted as function of logarithm of the concentration of the compound in FIGS. 14A-14C, 15A-15C, 16A-16C, 17A-17C, 18A-18C and 19A-19C, respectively. The $IC_{50}$ values of Compounds 16, 21, 22, 23, 24 and 31 to IDH1 R132C are less than 1.5 µM. The $IC_{50}$ values of the compounds to IDH1 R132C are shown in Table 9.

TABLE 9

$IC_{50}$ value of the compounds to IDH1 R132C

| Compound No. | IDH1 R132C $IC_{50}$ |
|---|---|
| 1 | 10-15 µM |
| 2 | 10-15 µM |
| 3 | 10-15 µM |
| 4 | 10-15 µM |
| 5 | 10-15 µM |
| 6 | 10-15 µM |

TABLE 9-continued

IC$_{50}$ value of the compounds to IDH1 R132C

| Compound No. | IDH1 R132C IC$_{50}$ |
|---|---|
| 7 | 10-15 μM |
| 8 | 10-15 μM |
| 9 | 10-15 μM |
| 10 | 10-15 μM |
| 11 | 10-15 μM |
| 12 | 10-15 μM |
| 13 | 10-15 μM |
| 14 | 10-15 μM |
| 15 | ≤1.5 μM |
| 16 | ≤1.5 μM |
| 17 | ≤1.5 μM |
| 18 | ≤1.5 μM |
| 19 | ≤1.5 μM |
| 20 | 1.5-10 μM |
| 21 | ≤1.5 μM |
| 22 | ≤1.5 μM |
| 23 | ≤1.5 μM |
| 24 | ≤1.5 μM |
| 31 | ≤1.5 μM |

The test for wild-type IDH1 inhibition of the compounds was also performed. It shows that the compounds showed no inhibiting effect to wild-type IDH1 at the concentrations tested (0.03125 μM to 2 μM).

Traditional chemotherapy normally have general nonspecific and toxic effect to the patients. The compounds tested in this example showed higher specificity in targeting mutant IDH rather than wild-type IDH. Such higher specificity allows usage of the compounds at a relatively low dosage to avoid side effects caused by inhibition to the endogenous wild type enzyme. Therefore, targeting mutant IDH gives flexibility in drug design and processing.

Example 5: Compounds Inhibit the D-2-HG Producing Activity of IDH1 R132C

Figure 20:
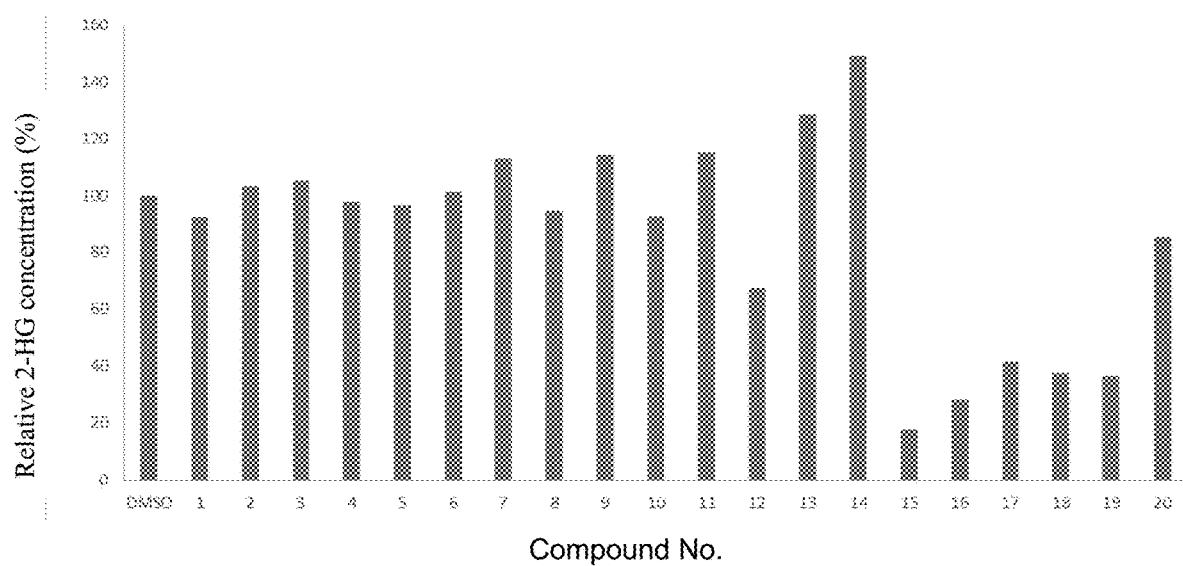
FIG. 20 shows D-2-HG concentration after the treatment with 10 μM each of the compounds 1-20 and negative control (DMSO).

HT1080 cells were cultured in 35 mm plate and treated with 10 μM of each of Compounds 1-37 for 12 h, and the D-2-HG concentration was analysed in accordance to the method disclosed in Test 6 of the Biological evaluation section. The D-2-HG concentration after the treatment of some of the compounds were shown in FIG. 20.

The D-2-HG inhibition activity of compounds was also assessed in the improved cell-based assay according to the method disclosed in Test 7 of the Biological evaluation section. HT1080 cells over-expressing D-2-HG dehydrogenase were cultured in 35 mm plate and treated with each of Compounds 1-37 at a concentration of 0.5 μM, 1 μM, 2.5 μM and 5 μM for 12 h, respectively, and the D-2-HG concentration was analysed. The inhibition ratio of D-2-HG in HT1080 cell by the exemplary Compounds 16, 21-24 and 31 at different concentrations were shown in Table 10.

TABLE 10

Inhibition ratio of D-2-HG in HT1080 cell by Compounds 16, 21-24 and 31 at different concentrations

| Compound No. | Inhibition ratio of D-2-HG in HT1080 cell (%) | | | |
|---|---|---|---|---|
| | 0.5 μM | 1 μM | 2.5 μM | 5 μM |
| 16 | 51 | 60.2 | 67 | 82.2 |
| 21 | 20.2 | 18.7 | 43.1 | 76.1 |
| 22 | 36.3 | 53.3 | 72.3 | 87.8 |
| 23 | 12.5 | 30.7 | 68.3 | 76.7 |
| 24 | 45.5 | 54.6 | 72.1 | 92.1 |
| 31 | 36.9 | 57.8 | 68.7 | 89.1 |

The results shows that the compounds effectively inhibited the D-2-HG producing activity of IDH1 R132C, and the inhibition activity of the compounds increases as the concentration of the compounds increases. At a concentration of 5 μM, all the exemplary compounds showed more than 70% inhibition activity.

Example 6: Compounds Inhibit Anchorage Independent Growth of HT1080 Cells

HT1080 cells are cultured in 35 mm plate and harvested at exponential growth phase, and used in soft agar in accordance to the description in Test 8 of the biological evaluation section. Compounds of present disclosure inhibit the anchorage-independent growth of IDH-mutant cancer cells.

Example 7: Compounds Inhibit IDH Mutant Tumor Growth in PDX Model

Animal tests are performed in accordance to the description in Test 9 of the biological evaluation section. Compounds of present disclosure inhibit the growth of the tumors harboring IDH1 R132H mutation in PDX models.

REFERENCES

1. Parsons, D. W., et al., *An integrated genomic analysis of human glioblastoma multiforme*. Science, 2008. 321 (5897): p. 1807-12.
2. Balss, J., et al., *Analysis of the IDH1 codon 132 mutation in brain tumors*. Acta Neuropathol, 2008. 116(6): p. 597-602.
3. Bleeker, F. E., et al., *IDH1 mutations at residue p.R132 (IDH (R132)) occur frequently in high-grade gliomas but not in other solid tumors*. Hum Mutat, 2009. 30(1): p. 7-11.
4. Hartmann, C., et al., *Type and frequency of IDH1 and IDH2 mutations are related to astrocytic and oligodendroglial differentiation and age: a study of 1,010 diffuse gliomas*. Acta Neuropathol, 2009. 118(4): p. 469-74.
5. Watanabe, T., et al., *IDH1 mutations are early events in the development of astrocytomas and oligodendrogliomas*. Am J Pathol, 2009. 174(4): p. 1149-53.
6. Mardis, E. R., et al., *Recurring mutations found by sequencing an acute myeloid leukemia genome*. N Engl J Med, 2009. 361(11): p. 1058-66.
7. Thol, F., et al., *Prognostic impact of IDH2 mutations in cytogenetically normal acute myeloid leukemia*. Blood, 2010. 116(4): p. 614-6.
8. Abbas, S., et al., *Acquired mutations in the genes encoding IDH1 and IDH2 both are recurrent aberrations in acute myeloid leukemia: prevalence and prognostic value*. Blood, 2010. 116(12): p. 2122-6.
9. Green, C. L., et al., *The prognostic significance of IDH1 mutations in younger adult patients with acute myeloid leukemia is dependent on FLT3/ITD status*. Blood, 2010. 116(15): p. 2779-82.

10. Schnittger, S., et al., *IDH1 mutations are detected in 6.6% of 1414 AML patients and are associated with intermediate risk karyotype and unfavorable prognosis in adults younger than 60 years and unmutated NPM1 status.* Blood, 2010. 116(25): p. 5486-96.
11. Marcucci, G, et al., *IDH1 and IDH2 gene mutations identify novel molecular subsets within de novo cytogenetically normal acute myeloid leukemia: a Cancer and Leukemia Group B study.* J Clin Oncol, 2010. 28(14): p. 2348-55.
12. Paschka, P., et al., *IDH1 and IDH2 mutations are frequent genetic alterations in acute myeloid leukemia and confer adverse prognosis in cytogenetically normal acute myeloid leukemia with NPM1 mutation without FLT3 internal tandem duplication.* J Clin Oncol, 2010. 28(22): p. 3636-43.
13. Ho, P. A., et al., *Molecular alterations of the IDH1 gene in AML: a Children's Oncology Group and Southwest Oncology Group study.* Leukemia, 2010. 24(5): p. 909-13.
14. Amary, M. F., et al., *IDH1 and IDH2 mutations are frequent events in central chondrosarcoma and central and periosteal chondromas but not in other mesenchymal tumours.* J Pathol, 2011. 224(3): p. 334-43.
15. Amary, M. F., et al., *Ollier disease and Maffucci syndrome are caused by somatic mosaic mutations of IDH1 and IDH2.* Nat Genet, 2011. 43(12): p. 1262-5.
16. Borger, D. R., et al., *Frequent mutation of isocitrate dehydrogenase (IDH)1 and IDH2 in cholangiocarcinoma identified through broad-based tumor genotyping.* Oncologist, 2012. 17(1): p. 72-9.
17. Wang, P., et al., *Mutations in isocitrate dehydrogenase 1 and 2 occur frequently in intrahepatic cholangiocarcinomas and share hypermethylation targets with glioblastomas.* Oncogene, 2012.
18. Sjoblom, T., et al., *The consensus coding sequences of human breast and colorectal cancers.* Science, 2006. 314(5797): p. 268-74.
19. Dang, L., S. Jin, and S. M. Su, *IDH mutations in glioma and acute myeloid leukemia.* Trends Mol Med, 2010. 16(9): p. 387-97.
20. Suzuki, H., et al., *Mutational landscape and clonal architecture in grade II and III gliomas.* Nat Genet, 2015. 47(5): p. 458-68.
21. Brat, D. J., et al., *Comprehensive, Integrative Genomic Analysis of Diffuse Lower-Grade Gliomas.* N Engl J Med, 2015. 372(26): p. 2481-98.
22. *Genomic and epigenomic landscapes of adult de novo acute myeloid leukemia.* N Engl J Med, 2013. 368(22): p. 2059-74.
23. Zhao, S., et al., *Glioma-derived mutations in IDH1 dominantly inhibit IDH1 catalytic activity and induce HIF-1alpha.* Science, 2009. 324(5924): p. 261-5.
24. Dang, L., et al., *Cancer-associated IDH1 mutations produce 2-hydroxyglutarate.* Nature, 2009. 462(7274): p. 739-44.
25. Xu, W., et al., *Oncometabolite 2-Hydroxyglutarate Is a Competitive Inhibitor of [alpha]-Ketoglutarate-Dependent Dioxygenases.* Cancer Cell, 2011. 19(1): p. 17-30.
26. Wang, P., et al., *Oncometabolite D-2-Hydroxyglutarate Inhibits ALKBH DNA Repair Enzymes and Sensitizes IDH Mutant Cells to Alkylating Agents.* Cell Rep, 2015. 13(11): p. 2353-61.
27. Ma, S., et al., *D-2-hydroxyglutarate is essential for maintaining oncogenic property of mutant IDH-containing cancer cells but dispensable for cell growth.* Oncotarget, 2015. 6(11): p. 8606-20.
28. Luchman, H. A., et al., *An in vivo patient-derived model of endogenous IDH1-mutant glioma.* Neuro Oncol, 2012. 14(2): p. 184-91.

What is claimed is:
1. A compound of Formula I:

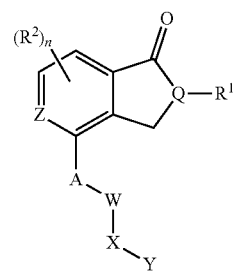

Formula (I)

or a pharmaceutically acceptable salt or ester thereof, wherein,

Z is N;

Q is C or N;

A is O, S, or $NR^a$;

W is linear or branched $C_{1-6}$ alkylene;

X is $C_{6-12}$ aryl, $C_{6-12}$ heteroaryl, 3-10 membered saturated or unsaturated cycloalkyl, 3-10 membered saturated or unsaturated heterocycloalkyl;

Y is halo, cyano, $C_{1-12}$ alkyl, $C_{6-12}$ aryl, $C_{1-12}$ alkoxyl, $C_{6-12}$ aryloxyl, 3-10 membered saturated or unsaturated cycloalkyl, 3-10 membered saturated or unsaturated heterocycloalkyl, cycloalkylalkyl, heterocycloalkylalkyl, —C(O)$OR^b$, —C(O)$NR^cR^d$, which can be optionally mono- or independently multi-substituted by one or more of halogen, hydroxyl, cyano, $C_{1-12}$ alkyl, $C_{2-12}$ alkenyl, $C_{2-12}$ alkynyl, $C_{5-10}$ aryl, $C_{1-12}$ alkoxy, 3-10 membered saturated or unsaturated cycloalkyl, 3-10 membered heterocycloalkyl, or 3-10 membered heteroaryl, $C_{5-10}$ aryloxyl;

$R^1$ is unsubstituted $C_{1-12}$ alkyl, 3-10 membered saturated or unsaturated cycloalkyl, aralkyl, alkoxyalkyl, hydroxyalkyl, alkoxyaralkyl, or —$NR^eR^f$;

$R^2$ is hydrogen, —$NR^gR^h$, —C(O)$OR^b$, or —C(O)$NR^cR^d$;

$R^a$, $R^b$, $R^c$, $R^d$, $R^e$, $R^f$, $R^g$ and $R^h$ are independently selected from hydrogen, $C_{1-12}$ alkyl, 3-10 membered saturated or unsaturated cycloalkyl, $C_{6-12}$ aryl, which can be optionally mono- or independently multi-substituted by halogen, hydroxyl, cyano, $C_{1-12}$ alkyl, $C_{2-12}$ alkenyl, $C_{2-12}$ alkynyl, $C_{5-10}$ aryl, $C_{1-12}$ alkoxy, 3-10 membered saturated or unsaturated cycloalkyl, 3-10 membered heterocycloalkyl, or 3-10 membered heteroaryl, $C_{5-10}$ aryloxyl;

optionally $R^c$ and $R^d$ are taken together with the nitrogen atom to which they are bound to form a 4- to 8-membered heterocyclyl optionally comprising one or more additional heteroatoms selected from N, S, and O, optionally $R^g$ and $R^h$ are taken together with the nitrogen atom to which they are bound to form a 4- to 8-membered heterocyclyl optionally comprising one or more additional heteroatoms selected from N, S, and O;

n is 0, 1 or 2.

2. The compound of claim 1, wherein the compound has the chemical structure shown in Formula (Ia):

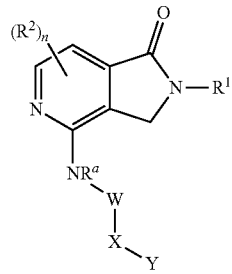

Formula (Ia)

or a pharmaceutically acceptable salt or ester thereof, wherein,

W is linear or branched $C_{1-6}$ alkylene;

X is $C_{6-12}$ aryl, $C_{6-12}$ heteroaryl, 3-10 membered saturated or unsaturated cycloalkyl, 3-10 membered saturated or unsaturated heterocycloalkyl;

Y is halo, cyano, $C_{1-12}$ alkyl, $C_{6-12}$ aryl, $C_{1-12}$ alkoxyl, $C_{6-12}$ aryloxyl, 3-10 membered saturated or unsaturated cycloalkyl, 3-10 membered saturated or unsaturated heterocycloalkyl, cycloalkylalkyl, heterocycloalkylalkyl, —C(O)OR$^b$, —C(O)NR$^c$R$^d$, which can be optionally mono- or independently multi-substituted by one or more of halogen, hydroxyl, cyano, $C_{1-12}$ alkyl, $C_{2-12}$ alkenyl, $C_{2-12}$ alkynyl, $C_{5-10}$ aryl, $C_{1-12}$ alkoxy, 3-10 membered saturated or unsaturated cycloalkyl, 3-10 membered heterocycloalkyl, or 3-10 membered heteroaryl, $C_{5-10}$ aryloxyl;

R$^1$ is unsubstituted $C_{1-12}$ alkyl, 3-10 membered saturated or unsaturated cycloalkyl, aralkyl, alkoxyalkyl, hydroxyalkyl, alkoxyaralkyl, or —NR$^e$R$^f$;

R$^2$ is hydrogen, —NR$^g$R$^h$, —C(O)OR$^b$, or —C(O)NR$^c$R$^d$;

R$^a$, R$^b$, R$^c$, R$^d$, R$^e$, R$^f$, R$^g$ and R$^h$ are independently selected from hydrogen, $C_{1-12}$ alkyl, 3-10 membered saturated or unsaturated cycloalkyl, $C_{6-12}$ aryl, which can be optionally mono- or independently multi-substituted by halogen, hydroxyl, cyano, $C_{1-12}$ alkyl, $C_{2-12}$ alkenyl, $C_{5-10}$ aryl, $C_{2-12}$ alkynyl, 3-10 membered saturated or unsaturated cycloalkyl, 3-10 membered heterocycloalkyl, or 3-10 membered heteroaryl, $C_{5-10}$ aryloxyl;

optionally R$^c$ and R$^d$ are taken together with the nitrogen atom to which they are bound to form a 4- to 8-membered heterocyclyl optionally comprising one or more additional heteroatoms selected from N, S, and O, optionally R$^g$ and R$^h$ are taken together with the nitrogen atom to which they are bound to form a 4- to 8-membered heterocyclyl optionally comprising one or more additional heteroatoms selected from N, S, and O;

n is 0, 1 or 2.

3. The compound of claim 1, wherein A is NR$^a$ and R$^a$ is hydrogen.

4. The compound of claim 1, wherein W is branched $C_{1-3}$ alkylene.

5. The compound of claim 1, wherein X is $C_{6-12}$ aryl or $C_{6-12}$ heteroaryl.

6. The compound of claim 5, wherein X is phenyl, pyridinyl or pyrazolyl.

7. The compound of claim 1, wherein Y is selected from the group consisting of:

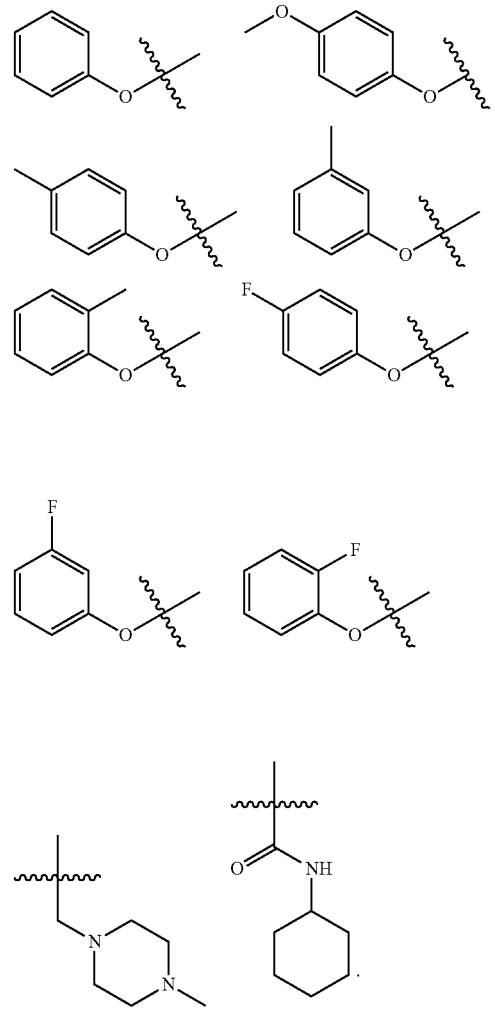

8. The compound of claim 1, wherein the compound has a (R)-configuration, a (S)-configuration or a mixture thereof.

9. The compound of claim 1, selected from the group consisting of

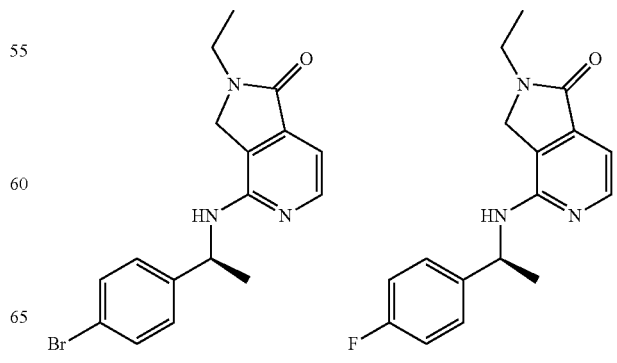

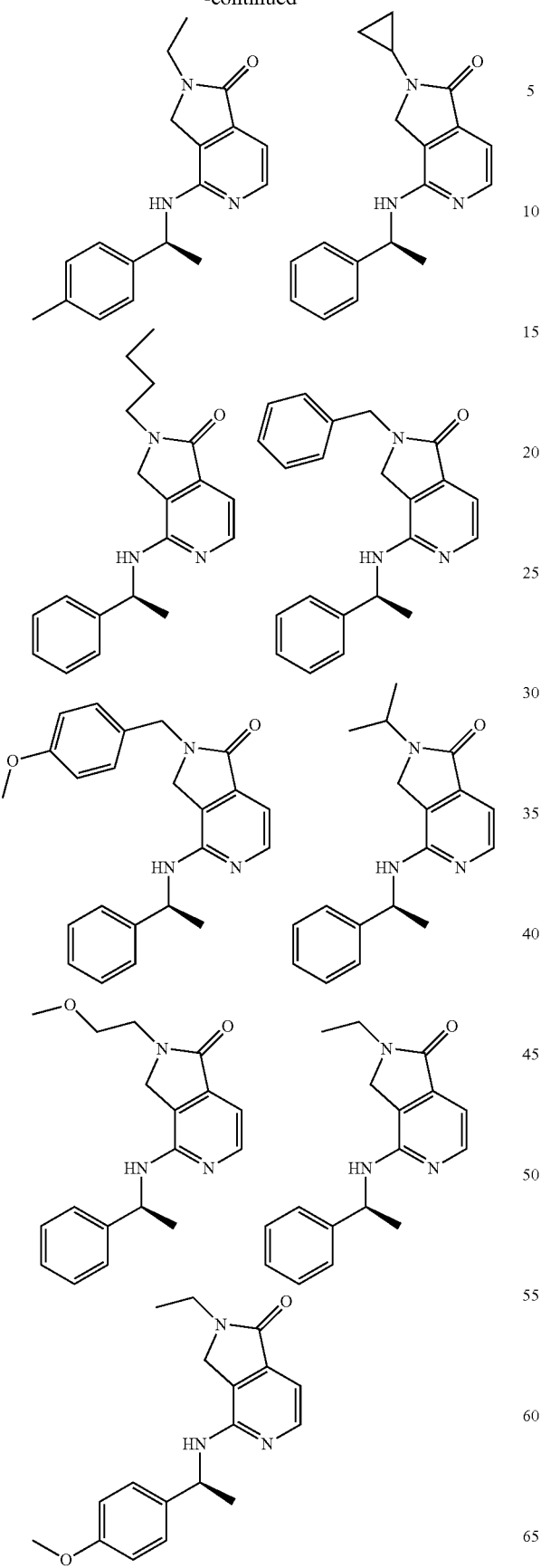
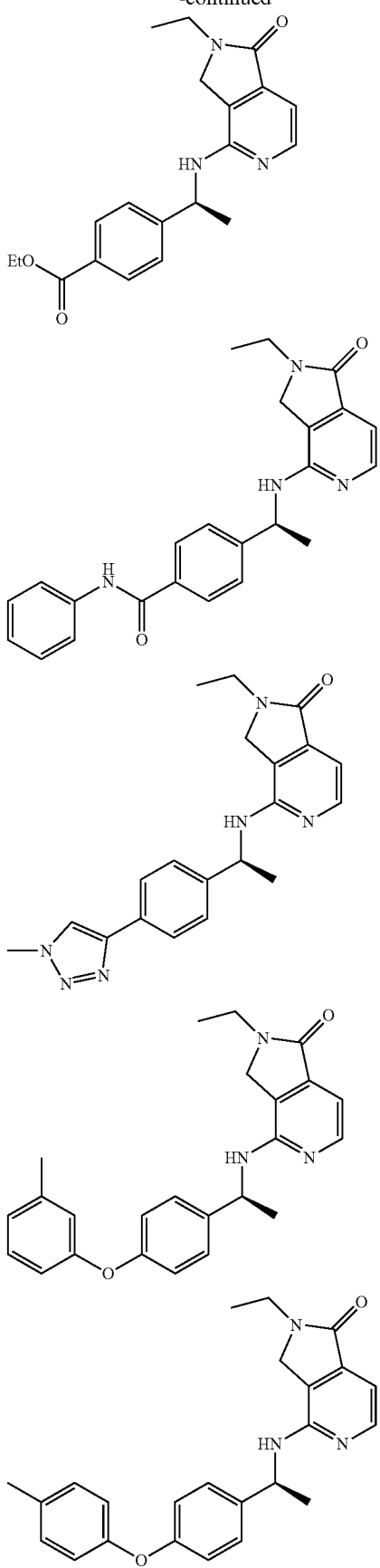

-continued
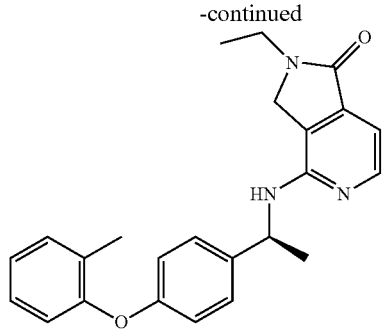
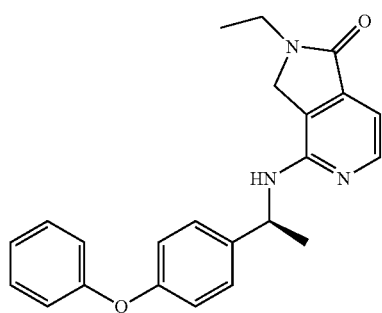
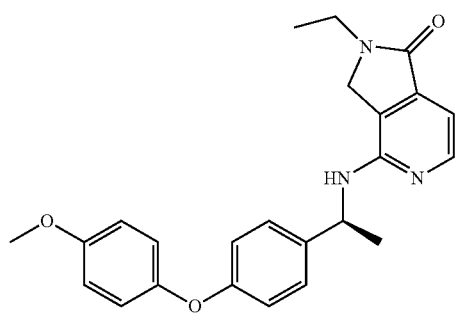
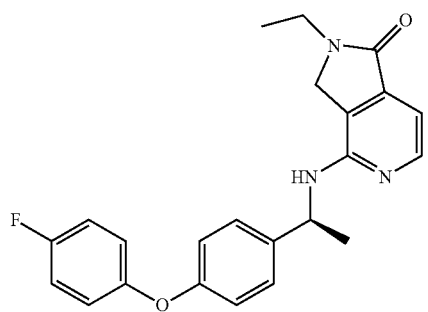
-continued
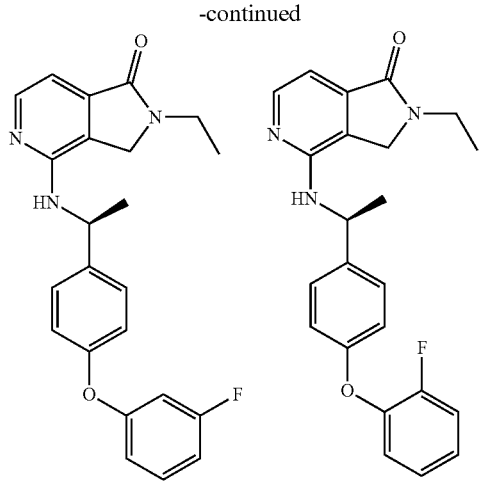
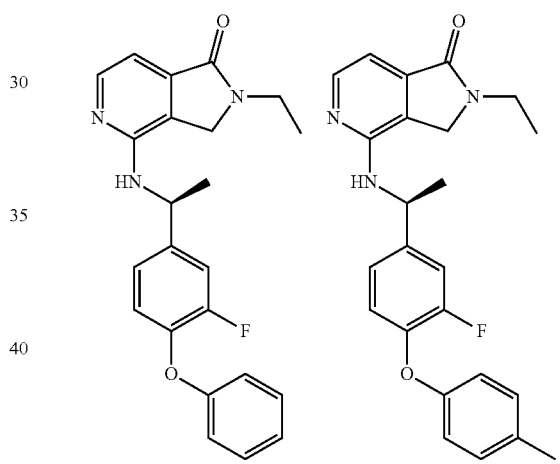
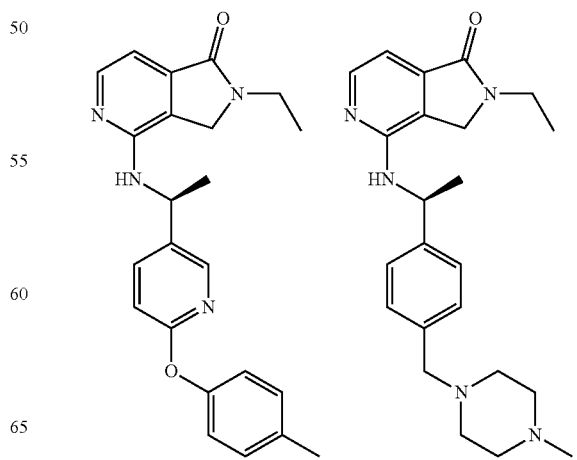

101
-continued
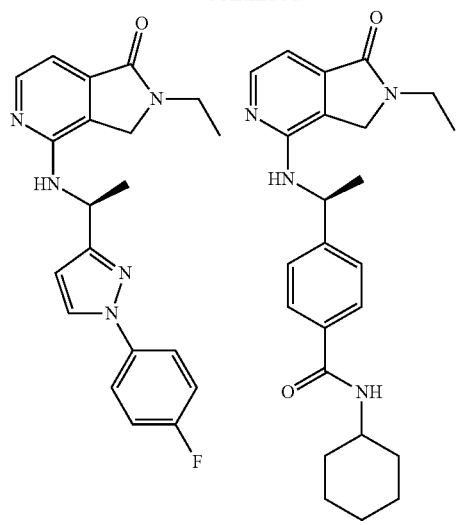
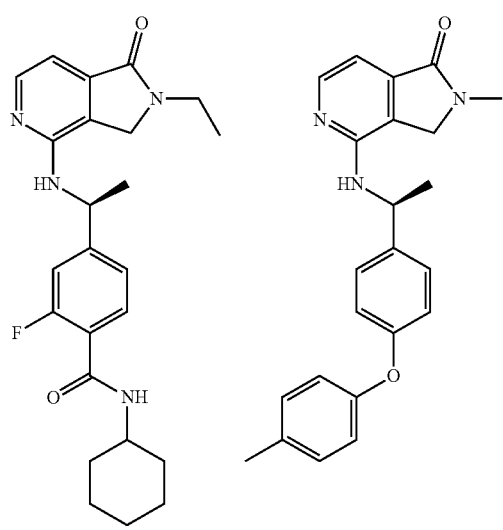
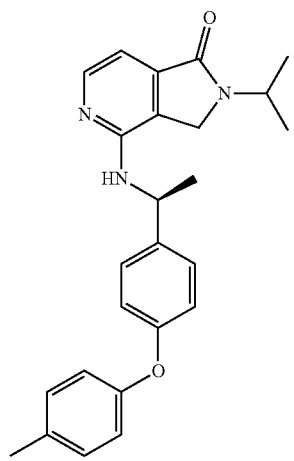
102
-continued
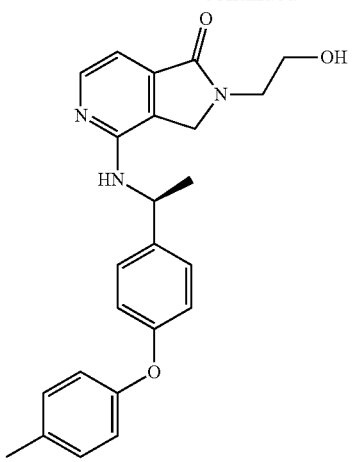
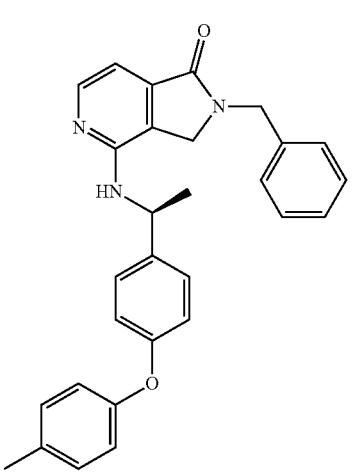
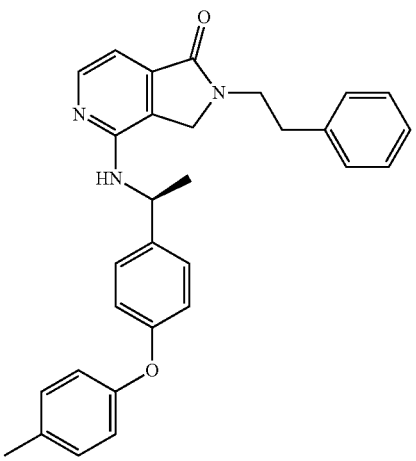

-continued

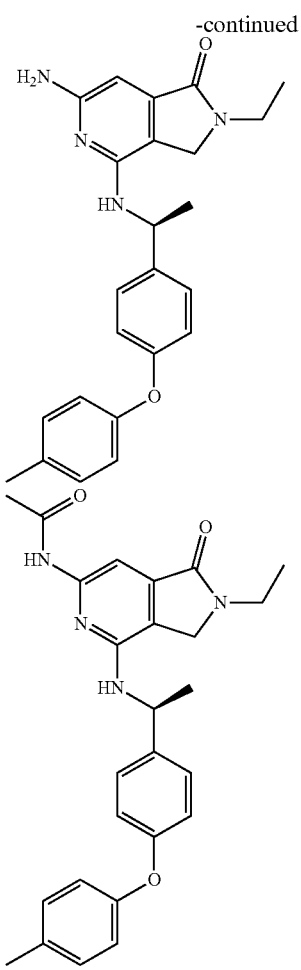

-continued

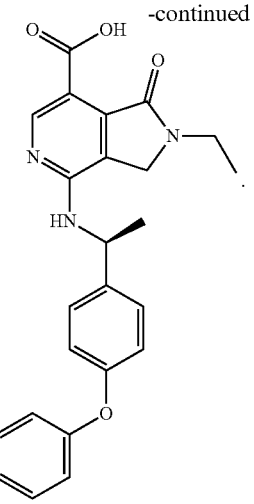

10. A pharmaceutical composition comprising one or more compounds, or pharmaceutically acceptable salts thereof according to claim 1 as a first active ingredient, and a pharmaceutically acceptable carrier.

11. A method of treating a cancer associated with the accumulation of D-2-HG in a subject in need thereof, comprising administering to a subject an effective amount of one or more compounds, or pharmaceutically acceptable salts thereof of claim 1.

12. A method of inhibiting conversion of α-KG to D-2-HG with one or more compounds, or pharmaceutically acceptable salts thereof of claim 1.

13. A method of inhibiting mutant IDH, wild-type IDH or both with one or more compounds, or pharmaceutically acceptable salts thereof of claim 1.

* * * * *